US007198935B1

(12) United States Patent
Bartosch et al.

(10) Patent No.: US 7,198,935 B1

(45) Date of Patent: Apr. 3, 2007

(54) INFECTIOUS PESTIVIRUS PSEUDO-PARTICLES CONTAINING FUNCTIONAL ERNS, E1, E2 ENVELOPE PROTEINS

(75) Inventors: Birke Bartosch, Chuzelles (FR); Francois-Loic Cosset, Lyons (FR)

(73) Assignee: Institut National de la Sante et de la Recherche Medicale (INSERM), Paris (FR)

(*) Notice: Subject to any disclaimer, the term of this patent is extended or adjusted under 35 U.S.C. 154(b) by 0 days.

(21) Appl. No.: 10/791,283

(22) Filed: Mar. 3, 2004

(30) Foreign Application Priority Data

Mar. 3, 2003 (EP) .................................. 03290506

(51) Int. Cl.
*C12N 7/00* (2006.01)

(52) U.S. Cl. ...................... 435/235.1; 435/6; 435/69.1; 424/204.1

(58) Field of Classification Search .................... 435/6, 435/69.1, 235.1; 424/204.1
See application file for complete search history.

(56) References Cited

FOREIGN PATENT DOCUMENTS

| | | |
|---|---|---|
| EP | 1 170 367 | 1/2002 |
| WO | WO 00/55335 | 9/2000 |

OTHER PUBLICATIONS

Lai et al. Journal of Virology, Jul. 2000, 74(14):6339-6347.*

* cited by examiner

*Primary Examiner*—Stacy B. Chen
(74) *Attorney, Agent, or Firm*—B. Aaron Schulman; Stites & Harbison PLLC

(57) ABSTRACT

The invention relates to the generation and the use of pestivirus pseudo-particles containing native functional E1, E2 envelope glycoproteins assembled onto retroviral core particles. These particles are highly infectious and constitute a valid model of pestivirus virion.

4 Claims, No Drawings

SEQUENCE LISTING

```
<160> NUMBER OF SEQ ID NOS: 26

<210> SEQ ID NO 1
<211> LENGTH: 12573
<212> TYPE: DNA
<213> ORGANISM: Bovine viral diarrhea virus
<220> FEATURE:
<221> NAME/KEY: CDS
<222> LOCATION: (890)..(1195)
<223> OTHER INFORMATION: C protein
<220> FEATURE:
<221> NAME/KEY: CDS
<222> LOCATION: (1196)..(1876)
<223> OTHER INFORMATION: E-rns protein
<220> FEATURE:
<221> NAME/KEY: CDS
<222> LOCATION: (1877)..(2461)
<223> OTHER INFORMATION: E1 protein
<220> FEATURE:
<221> NAME/KEY: CDS
<222> LOCATION: (2462)..(3583)
<223> OTHER INFORMATION: E2 protein
<220> FEATURE:
<221> NAME/KEY: CDS
<222> LOCATION: (3584)..(3793)
<223> OTHER INFORMATION: p7 protein

<400> SEQUENCE: 1

gtatacgaga attagaaaag gcactcgtat acgtattggg caattaaaaa taataattag     60

gcctagggaa caaatccctc tcagcgaagg ccgaaaagag gctagccatg cccttagtag    120

gactagcata atgagggggg tagcaacagt ggtgagttcg ttggatggct taagccctga    180

gtacagggta gtcgtcagtg gttcgacgcc ttggaataaa ggtctcgaga tgccacgtgg    240

acgagggcat gcccaaagca catcttaacc tgagcggggg tcgcccaggt aaaagcagtt    300

ttaaccgact gttacgaata cagcctgata gggtgctgca gaggcccact gtattgctac    360
```

-continued

```
taaaaatctc tgctgtacat ggcacatgga gttgatcaca aatgaacttt tatacaaaac    420

atacaaacaa aaacccgtcg gggtggagga acctgtttat gatcaggcag gtgatccctt    480

atttggtgaa aggggagcag tccaccctca atcgacgcta aagctcccac acaagagagg    540

ggaacgcgat gttccaacca acttggcatc cttaccaaaa agaggtgact gcaggtcggg    600

taatagcaga ggacctgtga gcgggatcta cctgaagcca gggccactat tttaccagga    660

ctataaaggt cccgtctatc acagggcccc gctggagctc tttgaggagg gatccatgtg    720

tgaaacgact aaacggatag ggagagtaac tggaagtgac ggaaagctgt accacattta    780

tgtgtgtata gatggatgta taataataaa aagtgccacg agaagttacc aaagggtgtt    840

caggtgggtc cataataggc ttgactgccc tctatgggtc acaacttgc tca gac acg    898
                                                      Ser Asp Thr
                                                      1

aaa gaa gag gga gca aca aaa aag aaa aca cag aaa ccc gac aga cta      946
Lys Glu Glu Gly Ala Thr Lys Lys Lys Thr Gln Lys Pro Asp Arg Leu
    5                  10                  15

gaa agg ggg aaa atg aaa ata gtg ccc aaa gaa tct gaa aaa gac agc      994
Glu Arg Gly Lys Met Lys Ile Val Pro Lys Glu Ser Glu Lys Asp Ser
20                  25                  30                  35

aaa act aaa cct ccg gat gct aca ata gtg gtg gaa gga gtc aaa tac     1042
Lys Thr Lys Pro Pro Asp Ala Thr Ile Val Val Glu Gly Val Lys Tyr
                40                  45                  50

cag gtg agg aag aag gga aaa acc aag agt aaa aac act cag gac ggc     1090
Gln Val Arg Lys Lys Gly Lys Thr Lys Ser Lys Asn Thr Gln Asp Gly
            55                  60                  65

ttg tac cat aac aaa aac aaa cct cag gaa tca cgc aag aaa ctg gaa     1138
Leu Tyr His Asn Lys Asn Lys Pro Gln Glu Ser Arg Lys Lys Leu Glu
        70                  75                  80

aaa gca ttg ttg gcg tgg gca ata ata gct ata gtt ttg ttt caa gtt     1186
Lys Ala Leu Leu Ala Trp Ala Ile Ile Ala Ile Val Leu Phe Gln Val
    85                  90                  95

aca atg gga gaa aac ata aca cag tgg aac cta caa gat aat ggg acg     1234
Thr Met Gly Glu Asn Ile Thr Gln Trp Asn Leu Gln Asp Asn Gly Thr
100                 105                 110                 115

gaa ggg ata caa cgg gca atg ttc caa agg ggt gtg aat aga agt tta     1282
Glu Gly Ile Gln Arg Ala Met Phe Gln Arg Gly Val Asn Arg Ser Leu
                120                 125                 130

cat gga atc tgg cca gag aaa atc tgt act ggc gtc cct tcc cat cta     1330
His Gly Ile Trp Pro Glu Lys Ile Cys Thr Gly Val Pro Ser His Leu
            135                 140                 145

gcc acc gat ata gaa cta aaa aca att cat ggt atg atg gat gca agt     1378
Ala Thr Asp Ile Glu Leu Lys Thr Ile His Gly Met Met Asp Ala Ser
        150                 155                 160

gag aag acc aac tac acg tgt tgc aga ctt caa cgc cat gag tgg aac     1426
Glu Lys Thr Asn Tyr Thr Cys Cys Arg Leu Gln Arg His Glu Trp Asn
    165                 170                 175

aag cat ggt tgg tgc aac tgg tac aat att gaa ccc tgg att cta gtc     1474
Lys His Gly Trp Cys Asn Trp Tyr Asn Ile Glu Pro Trp Ile Leu Val
180                 185                 190                 195

atg aat aga acc caa gcc aat ctc act gag gga caa cca cca agg gag     1522
Met Asn Arg Thr Gln Ala Asn Leu Thr Glu Gly Gln Pro Pro Arg Glu
                200                 205                 210

tgc gca gtc act tgt agg tat gat agg gct agt gac tta aac gtg gta     1570
Cys Ala Val Thr Cys Arg Tyr Asp Arg Ala Ser Asp Leu Asn Val Val
            215                 220                 225

aca caa gct aga gat agc ccc aca ccc tta aca ggt tgc aag aaa gga     1618
Thr Gln Ala Arg Asp Ser Pro Thr Pro Leu Thr Gly Cys Lys Lys Gly
        230                 235                 240
```

-continued

```
aag aac ttc tcc ttt gca ggc ata ttg atg cgg ggc ccc tgc aac ttt     1666
Lys Asn Phe Ser Phe Ala Gly Ile Leu Met Arg Gly Pro Cys Asn Phe
    245                 250                 255

gaa ata gct gca agt gat gta tta ttc aaa gaa cat gaa cgc att agt     1714
Glu Ile Ala Ala Ser Asp Val Leu Phe Lys Glu His Glu Arg Ile Ser
260                 265                 270                 275

atg ttc cag gat acc act ctt tac ctt gtt gac ggg ttg acc aac tcc     1762
Met Phe Gln Asp Thr Thr Leu Tyr Leu Val Asp Gly Leu Thr Asn Ser
                280                 285                 290

tta gaa ggt gcc aga caa gga acc gct aaa ctg aca acc tgg tta ggc     1810
Leu Glu Gly Ala Arg Gln Gly Thr Ala Lys Leu Thr Thr Trp Leu Gly
            295                 300                 305

aag cag ctc ggg ata cta gga aaa aag ttg gaa aac aag agt aag acg     1858
Lys Gln Leu Gly Ile Leu Gly Lys Lys Leu Glu Asn Lys Ser Lys Thr
        310                 315                 320

tgg ttt gga gca tac gct gct tcc cct tac tgt gat gtc gat cgc aaa     1906
Trp Phe Gly Ala Tyr Ala Ala Ser Pro Tyr Cys Asp Val Asp Arg Lys
    325                 330                 335

att ggc tac ata tgg tat aca aaa aat tgc acc cct gcc tgc tta ccc     1954
Ile Gly Tyr Ile Trp Tyr Thr Lys Asn Cys Thr Pro Ala Cys Leu Pro
340                 345                 350                 355

aag aac aca aaa att gtc ggc cct ggg aaa ttt ggc acc aat gca gag     2002
Lys Asn Thr Lys Ile Val Gly Pro Gly Lys Phe Gly Thr Asn Ala Glu
                360                 365                 370

gac ggc aag ata tta cat gag atg ggg ggt cac ttg tcg gag gta cta     2050
Asp Gly Lys Ile Leu His Glu Met Gly Gly His Leu Ser Glu Val Leu
            375                 380                 385

cta ctt tct tta gtg gtg ctg tcc gac ttc gca ccg gaa aca gct agt     2098
Leu Leu Ser Leu Val Val Leu Ser Asp Phe Ala Pro Glu Thr Ala Ser
        390                 395                 400

gta atg tac cta atc cta cat ttt tcc atc cca caa agt cac gtt gat     2146
Val Met Tyr Leu Ile Leu His Phe Ser Ile Pro Gln Ser His Val Asp
    405                 410                 415

gta atg gat tgt gat aag acc cag ttg aac ctc aca gtg gag ctg aca     2194
Val Met Asp Cys Asp Lys Thr Gln Leu Asn Leu Thr Val Glu Leu Thr
420                 425                 430                 435

aca gct gaa gta ata cca ggg tcg gtc tgg aat cta ggc aaa tat gta     2242
Thr Ala Glu Val Ile Pro Gly Ser Val Trp Asn Leu Gly Lys Tyr Val
                440                 445                 450

tgt ata aga cca aat tgg tgg cct tat gag aca act gta gtg ttg gca     2290
Cys Ile Arg Pro Asn Trp Trp Pro Tyr Glu Thr Thr Val Val Leu Ala
            455                 460                 465

ttt gaa gag gtg agc cag gtg gtg aag tta gtg ttg agg gca ctc aga     2338
Phe Glu Glu Val Ser Gln Val Val Lys Leu Val Leu Arg Ala Leu Arg
        470                 475                 480

gat tta aca cgc att tgg aac gct gca aca act act gct ttt tta gta     2386
Asp Leu Thr Arg Ile Trp Asn Ala Ala Thr Thr Thr Ala Phe Leu Val
    485                 490                 495

tgc ctt gtt aag ata gtc agg ggc cag atg gta cag ggc att ctg tgg     2434
Cys Leu Val Lys Ile Val Arg Gly Gln Met Val Gln Gly Ile Leu Trp
500                 505                 510                 515

cta cta ttg ata aca ggg gta caa ggg cac ttg gat tgc aaa cct gaa     2482
Leu Leu Leu Ile Thr Gly Val Gln Gly His Leu Asp Cys Lys Pro Glu
                520                 525                 530

ttc tcg tat gcc ata gca aag gac gaa aga att ggt caa ctg ggg gct     2530
Phe Ser Tyr Ala Ile Ala Lys Asp Glu Arg Ile Gly Gln Leu Gly Ala
            535                 540                 545

gaa ggc ctt acc acc act tgg aag gaa tac tca cct gga atg aag ctg     2578
Glu Gly Leu Thr Thr Thr Trp Lys Glu Tyr Ser Pro Gly Met Lys Leu
```

-continued

```
        550                 555                 560

gaa gac aca atg gtc att gct tgg tgc gaa gat ggg aag tta atg tac     2626
Glu Asp Thr Met Val Ile Ala Trp Cys Glu Asp Gly Lys Leu Met Tyr
    565                 570                 575

ctc caa aga tgc acg aga gaa acc aga tat ctc gca atc ttg cat aca     2674
Leu Gln Arg Cys Thr Arg Glu Thr Arg Tyr Leu Ala Ile Leu His Thr
580                 585                 590                 595

aga gcc ttg ccg acc agt gtg gta ttc aaa aaa ctc ttt gat ggg cga     2722
Arg Ala Leu Pro Thr Ser Val Val Phe Lys Lys Leu Phe Asp Gly Arg
                600                 605                 610

aag caa gag gat gta gtc gaa atg aac gac aac ttt gaa ttt gga ctc     2770
Lys Gln Glu Asp Val Val Glu Met Asn Asp Asn Phe Glu Phe Gly Leu
            615                 620                 625

tgc cca tgt gat gcc aaa ccc ata gta aga ggg aag ttc aat aca acg     2818
Cys Pro Cys Asp Ala Lys Pro Ile Val Arg Gly Lys Phe Asn Thr Thr
        630                 635                 640

ctg ctg aac gga ccg gcc ttc cag atg gta tgc ccc ata gga tgg aca     2866
Leu Leu Asn Gly Pro Ala Phe Gln Met Val Cys Pro Ile Gly Trp Thr
    645                 650                 655

ggg act gta agc tgt acg tca ttc aat atg gac acc tta gcc aca act     2914
Gly Thr Val Ser Cys Thr Ser Phe Asn Met Asp Thr Leu Ala Thr Thr
660                 665                 670                 675

gtg gta cgg aca tat aga agg tct aaa cca ttc cct cat agg caa ggc     2962
Val Val Arg Thr Tyr Arg Arg Ser Lys Pro Phe Pro His Arg Gln Gly
                680                 685                 690

tgt atc acc caa aag aat ctg ggg gag gat ctc cat aac tgc atc ctt     3010
Cys Ile Thr Gln Lys Asn Leu Gly Glu Asp Leu His Asn Cys Ile Leu
            695                 700                 705

gga gga aat tgg act tgt gtg cct gga gac caa cta cta tac aaa ggg     3058
Gly Gly Asn Trp Thr Cys Val Pro Gly Asp Gln Leu Leu Tyr Lys Gly
        710                 715                 720

ggc tct att gaa tct tgc aag tgg tgt ggc tat caa ttt aaa gag agt     3106
Gly Ser Ile Glu Ser Cys Lys Trp Cys Gly Tyr Gln Phe Lys Glu Ser
    725                 730                 735

gag gga cta cca cac tac ccc att ggc aag tgt aaa ttg gag aac gag     3154
Glu Gly Leu Pro His Tyr Pro Ile Gly Lys Cys Lys Leu Glu Asn Glu
740                 745                 750                 755

act ggt tac agg cta gta gac agt acc tct tgc aat aga gaa ggt gtg     3202
Thr Gly Tyr Arg Leu Val Asp Ser Thr Ser Cys Asn Arg Glu Gly Val
                760                 765                 770

gcc ata gta cca caa ggg aca tta aag tgc aag ata gga aaa aca act     3250
Ala Ile Val Pro Gln Gly Thr Leu Lys Cys Lys Ile Gly Lys Thr Thr
            775                 780                 785

gta cag gtc ata gct atg gat acc aaa ctc gga cct atg cct tgc aga     3298
Val Gln Val Ile Ala Met Asp Thr Lys Leu Gly Pro Met Pro Cys Arg
        790                 795                 800

cca tat gaa atc ata tca agt gag ggg cct gta gaa aag aca gcg tgt     3346
Pro Tyr Glu Ile Ile Ser Ser Glu Gly Pro Val Glu Lys Thr Ala Cys
    805                 810                 815

act ttc aac tac act aag aca tta aaa aat aag tat ttt gag ccc aga     3394
Thr Phe Asn Tyr Thr Lys Thr Leu Lys Asn Lys Tyr Phe Glu Pro Arg
820                 825                 830                 835

gac agc tac ttt cag caa tac atg cta aaa gga gag tat caa tac tgg     3442
Asp Ser Tyr Phe Gln Gln Tyr Met Leu Lys Gly Glu Tyr Gln Tyr Trp
                840                 845                 850

ttt gac ctg gag gtg act gac cat cac cgg gat tac ttc gct gag tcc     3490
Phe Asp Leu Glu Val Thr Asp His His Arg Asp Tyr Phe Ala Glu Ser
            855                 860                 865

ata tta gtg gtg gta gta gcc ctc ttg ggt ggc aga tat gta ctt tgg     3538
```

-continued

```
Ile Leu Val Val Val Val Ala Leu Leu Gly Gly Arg Tyr Val Leu Trp
        870                 875                 880

tta ctg gtt aca tac atg gtc tta tca gaa cag aag gcc tta ggg att     3586
Leu Leu Val Thr Tyr Met Val Leu Ser Glu Gln Lys Ala Leu Gly Ile
    885                 890                 895

cag tat gga tca ggg gaa gtg gtg atg atg ggc aac ttg cta acc cat     3634
Gln Tyr Gly Ser Gly Glu Val Val Met Met Gly Asn Leu Leu Thr His
900                 905                 910                 915

aac aat att gaa gtg gtg aca tac ttc ttg ctg ctg tac cta ctg ctg     3682
Asn Asn Ile Glu Val Val Thr Tyr Phe Leu Leu Leu Tyr Leu Leu Leu
                920                 925                 930

agg gag gag agc gta aag aag tgg gtc tta ctc tta tac cac atc tta     3730
Arg Glu Glu Ser Val Lys Lys Trp Val Leu Leu Leu Tyr His Ile Leu
            935                 940                 945

gtg gta cac cca atc aaa tct gta att gtg atc cta ctg atg att ggg     3778
Val Val His Pro Ile Lys Ser Val Ile Val Ile Leu Leu Met Ile Gly
        950                 955                 960

gat gtg gta aag gcc gattcagggg gccaagagta cttggggaaa atagacctct     3833
Asp Val Val Lys Ala
    965

gttttacaac agtagtacta atcgtcatag gtttaatcat agctaggcgt gacccaacta   3893

tagtgccact ggtaacaata atggcagcac tgagggtcac tgaactgacc caccagcctg   3953

gagttgacat cgctgtggcg gtcatgacta taaccctact gatggttagc tatgtgacag   4013

attattttag atataaaaaa tggttacagt gcattctcag cctggtatct gcggtgttct   4073

tgataagaag cctaatatac ctaggtagaa tcgagatgcc agaggtaact atcccaaact   4133

ggagaccact aactttaata ctattatatt tgatctcaac aacaattgta acgaggtgga   4193

aggttgacgt ggctggccta ttgttgcaat gtgtgcctat cttattgctg gtcacaacct   4253

tgtgggccga cttcttaacc ctaatactga tcctgcctac ctatgaattg gttaaattat   4313

actatctgaa aactgttagg actgatacag aaagaagttg gctagggggg atagactata   4373

caagagttga ctccatctac gacgttgatg agagtggaga gggcgtatat ctttttccat   4433

caaggcagaa agcacagggg aatttttcta tactcttgcc ccttatcaaa gcaacactga   4493

taagttgcgt cagcagtaaa tggcagctaa tatacatgag ttacttaact ttggacttta   4553

tgtactacat gcacaggaaa gttatagaag agatctcagg aggtaccaac ataatatcca   4613

ggttagtggc agcactcata gagctgaact ggtccatgga agaagaggag agcaaaggct   4673

taaagaagtt ttatctattg tctggaaggt tgagaaacct aataataaaa cataaggtaa   4733

ggaatgagac cgtggcttct tggtacgggg aggaggaagt ctacggtatg ccaaagatca   4793

tgactataat caaggccagt acactgagta agagcaggca ctgcataata tgcactgtat   4853

gtgagggccg agagtggaaa ggtggcacct gcccaaaatg tggacgccat gggaagccga   4913

taacgtgtgg gatgtcgcta gcagattttg aagaaagaca ctataaaaga atctttataa   4973

gggaaggcaa ctttgagggt atgtgcagcc gatgccaggg aaagcatagg aggtttgaaa   5033

tggaccggga acctaagagt gccagatact gtgctgagtg taataggctg catcctgctg   5093

aggaaggtga cttttgggca gagtcgagca tgttgggcct caaaatcacc tactttgcgc   5153

tgatggatgg aaaggtgtat gatatcacag agtgggctgg atgccagcgt gtgggaatct   5213

ccccagatac ccacagagtc ccttgtcaca tctcatttgg ttcacggatg cctttcaggc   5273

aggaatacaa tggctttgta caatataccg ctaggggggca actatttctg agaaacttgc   5333

ccgtactggc aactaaagta aaaatgctca tggtaggcaa ccttggagaa gaaattggta   5393
```

-continued

```
atctggaaca tcttgggtgg atcctaaggg ggcctgccgt gtgtaagaag atcacagagc   5453
acgaaaaatg ccacattaat atactggata aactaaccgc atttttcggg atcatgccaa   5513
gggggactac acccagagcc ccggtgaggt tccctacgag cttactaaaa gtgaggaggg   5573
gtctggagac tgcctgggct tacacacacc aaggcgggat aagttcagtc gaccatgtaa   5633
ccgccggaaa agatctactg gtctgtgaca gcatgggacg aactagagtg gtttgccaaa   5693
gcaacaacag gttgaccgat gagacagagt atggcgtcaa gactgactca gggtgcccag   5753
acggtgccag atgttatgtg ttaaatccag aggccgttaa catatcagga tccaaagggg   5813
cagtcgttca cctccaaaag acaggtggag aattcacgtg tgtcaccgca tcaggcacac   5873
cggctttctt cgacctaaaa aacttgaaag gatggtcagg cttgcctata tttgaagcct   5933
ccagcgggag ggtggttggc agagtcaaag tagggaagaa tgaagagtct aaacctacaa   5993
aaataatgag tggaatccag accgtctcaa aaaacagagc agacctgacc gagatggtca   6053
agaagataac cagcatgaac aggggagact tcaagcagat tactttggca acaggggcag   6113
gcaaaaccac agaactccca aaagcagtta tagaggagat aggaagacac aagagagtat   6173
tagttcttat accattaagg gcagcggcag agtcagtcta ccagtatatg agattgaaac   6233
acccaagcat ctcttttaac ctaaggatag gggacatgaa agagggggac atggcaaccg   6293
ggataaccta tgcatcatac gggtacttct gccaaatgcc tcaaccaaag ctcagagctg   6353
ctatggtaga atactcatac atattcttag atgaatacca ttgtgccact cctgaacaac   6413
tggcaattat cgggaagatc cacagatttt cagagagtat aagggttgtc gccatgactg   6473
ccacgccagc agggtcggtg accacaacag gtcaaaagca cccaatagag gaattcatag   6533
cccccgaggt aatgaaaggg gaggatcttg gtagtcagtt ccttgatata gcagggttaa   6593
aaataccagt ggatgagatg aaaggcaata tgttggtttt tgtaccaacg agaaacatgg   6653
cagtagaggt agcaaagaag ctaaaagcta agggctataa ctctggatac tattacagtg   6713
gagaggatcc agccaatctg agagttgtga catcacaatc cccctatgta atcgtggcta   6773
caaatgctat tgaatcagga gtgacactac cagatttgga cacggttata gacacggggt   6833
tgaaatgtga aaagagggtg agggtatcat caaagatacc cttcatcgta acaggcctta   6893
agaggatggc cgtgactgtg ggtgagcagg cgcagcgtag ggcagagta ggtagagtga   6953
aacccgggag gtattatagg agccaggaaa cagcaacagg gtcaaaggac taccactatg   7013
acctcttgca ggcacaaaga tacgggattg aggatggaat caacgtgacg aaatccttta   7073
gggagatgaa ttacgattgg agcctatacg aggaggacag cctactaata acccagctgg   7133
aaatactaaa taatctactc atctcagaag acttgccagc cgctgttaag aacataatgg   7193
ccaggactga tcacccagag ccaatccaac ttgcatacaa cagctatgaa gtccaggtcc   7253
cggtcctatt cccaaaaata aggaatggag aagtcacaga cacctacgaa aattactcgt   7313
ttctaaatgc cagaaagtta ggggaggatg tgcccgtgta tatctacgct actgaagatg   7373
aggatctggc agttgacctc ttagggctag actggcctga tcctgggaac cagcaggtag   7433
tggagactgg taaagcactg aagcaagtga ccgggttgtc ctcggctgaa aatgccctac   7493
tagtggcttt atttgggtat gtgggttacc aggctctctc aaagaggcat gtcccaatga   7553
taacagacat atataccatc gaggaccaga gactagaaga caccacccac ctccagtatg   7613
cacccaacgc cataaaaacc gatgggacag agactgaact gaaagaactg gcgtcgggtg   7673
acgtggaaaa aatcatggga gccatttcag attatgcagc tgggggactg gagtttgtta   7733
aatcccaagc agaaaagata aaaacagctc ctttgtttaa agaaaacgca gaagccgcaa   7793
```

-continued

```
aagggtatgt ccaaaaattc attgactcat taattgaaaa taaagaagaa ataatcagat    7853
atggtttgtg ggaacacac acagcactat acaaaagcat agctgcaaga ctggggcatg     7913
aaacagcgtt tgccacacta gtgttaaagt ggctagcttt tggaggggaa tcagtgtcag    7973
accacgtcaa gcaggcggca gttgatttag tggtctatta tgtgatgaat aagccttcct    8033
tcccaggtga ctccgagaca cagcaagaag ggaggcgatt cgtcgcaagc ctgttcatct    8093
ccgcactggc aacctacaca tacaaaactt ggaattacca caatctctct aaagtggtgg    8153
aaccagccct ggcttacctc ccctatgcta ccagcgcatt aaaaatgttc accccaacgc    8213
ggctggagag cgtggtgata ctgagcacca cgatatataa aacatacctc tctataagga    8273
aggggaagag tgatggattg ctgggtacgg ggataagtgc agccatggaa atcctgtcac    8333
aaaacccagt atcggtaggt atatctgtga tgttgggggt aggggcaatc gctgcgcaca    8393
acgctattga gtccagtgaa cagaaaagga ccctacttat gaaggtgttt gtaaagaact    8453
tcttggatca ggctgcaaca gatgagctgg taaaagaaaa cccagaaaaa attataatgg    8513
ccttatttga agcagtccag acaattggta accccctgag actaatatac cacctgtatg    8573
gggtttacta caaaggttgg gaggccaagg aactatctga gaggacagca ggcagaaact    8633
tattcacatt gataatgttt gaagccttcg agttattagg gatggactca caagggaaaa    8693
taaggaacct gtccggaaat tacattttgg atttgatata cggcctacac aagcaaatca    8753
acagagggct gaagaaaatg gtactggggt gggcccctgc accctttagt tgtgactgga    8813
cccctagtga cgagaggatc agattgccaa cagacaacta tttgaggtga gaaaccaggt    8873
gcccatgtgg ctatgagatg aaagctttca aaaatgtagg tggcaaactt accaaagtgg    8933
aggagagcgg gcctttccta tgtagaaaca gacctggtag gggaccagtc aactacagag    8993
tcaccaagta ttacgatgac aacctcagag agataaaacc agtagcaaag ttggaaggac    9053
aggtagagca ctactacaaa ggggtcacag caaaaattga ctacagtaaa ggaaaaatgc    9113
tcttggccac tgacaagtgg gaggtggaac atggtgtcat aaccaggtta gctaagagat    9173
atactggggt cgggttcaat ggtgcatact taggtgacga gcccaatcac cgtgctctag    9233
tggagaggga ctgtgcaact ataaccaaaa acacagtaca gtttctaaaa atgaagaagg    9293
ggtgtgcgtt cacctatgac ctgaccatct ccaatctgac caggctcatc gaactagtac    9353
acaggaacaa tcttgaagag aaggaaatac ccaccgctac ggtcaccaca tggctagctt    9413
acaccttcgt gaatgaagac gtagggacta taaaaccagt actaggagag agagtaatcc    9473
ccgaccctgt agttgatatc aatttacaac cagaggtgca agtggacacg tcagaggttg    9533
ggatcacaat aattggaagg gaaaccctga tgacaacggg agtgacacct gtcttggaaa    9593
aagtagagcc tgacgccagc gacaaccaaa actcggtgaa gatcgggttg gatgagggta    9653
attacccagg gcctggaata cagacacata cactaacaga agaaatacac aacagggatg    9713
cgaggccctt catcatgatc ctgggctcaa ggaattccat atcaaatagg gcaaagactg    9773
ctagaaatat aaatctgtac acaggaaatg accccaggga aatacgagac ttgatggctg    9833
cagggcgcat gttagtagta gcactgaggg atgtcgaccc tgagctgtct gaaatggtcg    9893
atttcaaggg gactttttta gatagggagg ccctggaggc tctaagtctc gggcaaccta    9953
aaccgaagca ggttaccaag gaagctgtta ggaatttgat agaacagaaa aaagatgtgg   10013
agatccctaa ctggtttgca tcagatgacc cagtatttct ggaagtggcc ttaaaaaatg   10073
ataagtacta cttagtagga gatgttggag agctaaaaga tcaagctaaa gcacttgggg   10133
```

-continued

```
ccacggatca gacaagaatt ataaaggagg taggctcaag gacgtatgcc atgaagctat  10193
ctagctggtt cctcaaggca tcaaacaaac agatgagttt aactccactg tttgaggaat  10253
tgttgctacg gtgcccacct gcaactaaga gcaataaggg gcacatggca tcagcttacc  10313
aattggcaca gggtaactgg gagcccctcg gttgcggggt gcacctaggt acaataccag  10373
ccagaagggt gaagatacac ccatatgaag cttacctgaa gttgaaagat ttcatagaag  10433
aagaagagaa gaaacctagg gttaaggata cagtaataag agagcacaac aaatggatac  10493
ttaaaaaaat aaggtttcaa ggaaacctca acaccaagaa aatgctcaac ccagggaaac  10553
tatctgaaca gttggacagg gaggggcgca agaggaacat ctacaaccac cagattggta  10613
ctataatgtc aagtgcaggc ataaggctgg agaaattgcc aatagtgagg gcccaaaccg  10673
acaccaaaac ctttcatgag gcaataagag ataagataga caagagtgaa aaccggcaaa  10733
atccagaatt gcacaacaaa ttgttggaga ttttccacac gatagcccaa cccaccctga  10793
aacacaccta cggtgaggtg acgtgggagc aacttgaggc gggggtaaat agaaaggggg  10853
cagcaggctt cctggagaag aagaacatcg gagaagtatt ggattcagaa aagcacctgg  10913
tagaacaatt ggtcagggat ctgaaggccg ggagaaagat aaaatattat gaaactgcaa  10973
taccaaaaaa tgagaagaga gatgtcagtg atgactggca ggcaggggac ctggtggttg  11033
agaagaggcc aagagttatc caataccctg aagccaagac aaggctagcc atcactaagg  11093
tcatgtataa ctgggtgaaa cagcagcccg ttgtgattcc aggatatgaa ggaaagaccc  11153
ccttgttcaa catctttgat aaagtgagaa aggaatggga ctcgttcaat gagccagtgg  11213
ccgtaagttt tgacaccaaa gcctgggaca ctcaagtgac tagtaaggat ctgcaactta  11273
ttggagaaat ccagaaatat tactataaga aggagtggca caagttcatt gacaccatca  11333
ccgaccacat gacagaagta ccagttataa cagcagatgg tgaagtatat ataagaaatg  11393
ggcagagagg gagcggccag ccagacacaa gtgctggcaa cagcatgtta aatgtcctga  11453
caatgatgta cggcttctgc gaaagcacag gggtaccgta caagagtttc aacagggtgg  11513
caaggatcca cgtctgtggg gatgatggct tcttaataac tgaaaaaggg ttagggctga  11573
aatttgctaa caaagggatg cagattcttc atgaagcagg caaacctcag aagataacgg  11633
aaggggaaaa gatgaaagtt gcctatagat ttgaggatat agagttctgt tctcataccc  11693
cagtccctgt taggtggtcc gacaacacca gtagtcacat ggccgggaga gacaccgctg  11753
tgatactatc aaagatggca acaagattgg attcaagtgg agagaggggt accacagcat  11813
atgaaaaagc ggtagccttc agtttcttgc tgatgtattc ctggaacccg cttgttagga  11873
ggatttgcct gttggtcctt tcgcaacagc cagagacaga cccatcaaaa catgccactt  11933
attattacaa aggtgatcca atagggggcct ataaagatgt aataggtcgg aatctaagtg  11993
aactgaagag aacaggcttt gagaaattgg caaatctaaa cctaagcctg tccacgttgg  12053
gggtctggac taagcacaca agcaaaagaa taattcagga ctgtgttgcc attgggaaag  12113
aagagggcaa ctggctagtt aagcccgaca ggctgatatc cagcaaaact ggccacttat  12173
acatacctga taaaggcttt acattacaag gaaagcatta tgagcaactg cagctaagaa  12233
cagagacaaa cccggtcatg gggggttggga ctgagagata caagttaggt cccatagtca  12293
atctgctgct gagaaggttg aaaattctgc tcatgacggc cgtcggcgtc agcagctgag  12353
acaaaatgta tatattgtaa ataaattaat ccatgtacat agtgtatata aatatagttg  12413
ggaccgtcca cctcaagaag acgacacgcc caacacgcac agctaaacag tagtcaagat  12473
tatctacctc aagataacac tacatttaat gcacacagca ctttagctgt atgaggatac  12533
```

-continued

```
gcccgacgtc tatagttgga ctagggaaga cctctaacag                12573


<210> SEQ ID NO 2
<211> LENGTH: 102
<212> TYPE: PRT
<213> ORGANISM: Bovine viral diarrhea virus

<400> SEQUENCE: 2

Ser Asp Thr Lys Glu Glu Gly Ala Thr Lys Lys Lys Thr Gln Lys Pro
1               5                   10                  15

Asp Arg Leu Glu Arg Gly Lys Met Lys Ile Val Pro Lys Glu Ser Glu
            20                  25                  30

Lys Asp Ser Lys Thr Lys Pro Pro Asp Ala Thr Ile Val Val Glu Gly
        35                  40                  45

Val Lys Tyr Gln Val Arg Lys Lys Gly Lys Thr Lys Ser Lys Asn Thr
    50                  55                  60

Gln Asp Gly Leu Tyr His Asn Lys Asn Lys Pro Gln Glu Ser Arg Lys
65                  70                  75                  80

Lys Leu Glu Lys Ala Leu Leu Ala Trp Ala Ile Ile Ala Ile Val Leu
                85                  90                  95

Phe Gln Val Thr Met Gly
            100


<210> SEQ ID NO 3
<211> LENGTH: 227
<212> TYPE: PRT
<213> ORGANISM: Bovine viral diarrhea virus

<400> SEQUENCE: 3

Glu Asn Ile Thr Gln Trp Asn Leu Gln Asp Asn Gly Thr Glu Gly Ile
1               5                   10                  15

Gln Arg Ala Met Phe Gln Arg Gly Val Asn Arg Ser Leu His Gly Ile
            20                  25                  30

Trp Pro Glu Lys Ile Cys Thr Gly Val Pro Ser His Leu Ala Thr Asp
        35                  40                  45

Ile Glu Leu Lys Thr Ile His Gly Met Met Asp Ala Ser Glu Lys Thr
    50                  55                  60

Asn Tyr Thr Cys Cys Arg Leu Gln Arg His Glu Trp Asn Lys His Gly
65                  70                  75                  80

Trp Cys Asn Trp Tyr Asn Ile Glu Pro Trp Ile Leu Val Met Asn Arg
                85                  90                  95

Thr Gln Ala Asn Leu Thr Glu Gly Gln Pro Pro Arg Glu Cys Ala Val
            100                 105                 110

Thr Cys Arg Tyr Asp Arg Ala Ser Asp Leu Asn Val Val Thr Gln Ala
        115                 120                 125

Arg Asp Ser Pro Thr Pro Leu Thr Gly Cys Lys Lys Gly Lys Asn Phe
    130                 135                 140

Ser Phe Ala Gly Ile Leu Met Arg Gly Pro Cys Asn Phe Glu Ile Ala
145                 150                 155                 160

Ala Ser Asp Val Leu Phe Lys Glu His Glu Arg Ile Ser Met Phe Gln
                165                 170                 175

Asp Thr Thr Leu Tyr Leu Val Asp Gly Leu Thr Asn Ser Leu Glu Gly
            180                 185                 190

Ala Arg Gln Gly Thr Ala Lys Leu Thr Thr Trp Leu Gly Lys Gln Leu
        195                 200                 205
```

-continued

```
Gly Ile Leu Gly Lys Lys Leu Glu Asn Lys Ser Lys Thr Trp Phe Gly
    210                 215                 220

Ala Tyr Ala
225


<210> SEQ ID NO 4
<211> LENGTH: 195
<212> TYPE: PRT
<213> ORGANISM: Bovine viral diarrhea virus

<400> SEQUENCE: 4

Ala Ser Pro Tyr Cys Asp Val Asp Arg Lys Ile Gly Tyr Ile Trp Tyr
1               5                   10                  15

Thr Lys Asn Cys Thr Pro Ala Cys Leu Pro Lys Asn Thr Lys Ile Val
            20                  25                  30

Gly Pro Gly Lys Phe Gly Thr Asn Ala Glu Asp Gly Lys Ile Leu His
        35                  40                  45

Glu Met Gly Gly His Leu Ser Glu Val Leu Leu Leu Ser Leu Val Val
    50                  55                  60

Leu Ser Asp Phe Ala Pro Glu Thr Ala Ser Val Met Tyr Leu Ile Leu
65                  70                  75                  80

His Phe Ser Ile Pro Gln Ser His Val Asp Val Met Asp Cys Asp Lys
                85                  90                  95

Thr Gln Leu Asn Leu Thr Val Glu Leu Thr Thr Ala Glu Val Ile Pro
            100                 105                 110

Gly Ser Val Trp Asn Leu Gly Lys Tyr Val Cys Ile Arg Pro Asn Trp
        115                 120                 125

Trp Pro Tyr Glu Thr Thr Val Val Leu Ala Phe Glu Glu Val Ser Gln
    130                 135                 140

Val Val Lys Leu Val Leu Arg Ala Leu Arg Asp Leu Thr Arg Ile Trp
145                 150                 155                 160

Asn Ala Ala Thr Thr Thr Ala Phe Leu Val Cys Leu Val Lys Ile Val
                165                 170                 175

Arg Gly Gln Met Val Gln Gly Ile Leu Trp Leu Leu Leu Ile Thr Gly
            180                 185                 190

Val Gln Gly
        195


<210> SEQ ID NO 5
<211> LENGTH: 374
<212> TYPE: PRT
<213> ORGANISM: Bovine viral diarrhea virus

<400> SEQUENCE: 5

His Leu Asp Cys Lys Pro Glu Phe Ser Tyr Ala Ile Ala Lys Asp Glu
1               5                   10                  15

Arg Ile Gly Gln Leu Gly Ala Glu Gly Leu Thr Thr Thr Trp Lys Glu
            20                  25                  30

Tyr Ser Pro Gly Met Lys Leu Glu Asp Thr Met Val Ile Ala Trp Cys
        35                  40                  45

Glu Asp Gly Lys Leu Met Tyr Leu Gln Arg Cys Thr Arg Glu Thr Arg
    50                  55                  60

Tyr Leu Ala Ile Leu His Thr Arg Ala Leu Pro Thr Ser Val Val Phe
65                  70                  75                  80

Lys Lys Leu Phe Asp Gly Arg Lys Gln Glu Asp Val Val Glu Met Asn
                85                  90                  95
```

-continued

```
Asp Asn Phe Glu Phe Gly Leu Cys Pro Cys Asp Ala Lys Pro Ile Val
            100                 105                 110

Arg Gly Lys Phe Asn Thr Thr Leu Leu Asn Gly Pro Ala Phe Gln Met
        115                 120                 125

Val Cys Pro Ile Gly Trp Thr Gly Thr Val Ser Cys Thr Ser Phe Asn
    130                 135                 140

Met Asp Thr Leu Ala Thr Thr Val Val Arg Thr Tyr Arg Arg Ser Lys
145                 150                 155                 160

Pro Phe Pro His Arg Gln Gly Cys Ile Thr Gln Lys Asn Leu Gly Glu
                165                 170                 175

Asp Leu His Asn Cys Ile Leu Gly Gly Asn Trp Thr Cys Val Pro Gly
            180                 185                 190

Asp Gln Leu Leu Tyr Lys Gly Gly Ser Ile Glu Ser Cys Lys Trp Cys
        195                 200                 205

Gly Tyr Gln Phe Lys Glu Ser Glu Gly Leu Pro His Tyr Pro Ile Gly
    210                 215                 220

Lys Cys Lys Leu Glu Asn Glu Thr Gly Tyr Arg Leu Val Asp Ser Thr
225                 230                 235                 240

Ser Cys Asn Arg Glu Gly Val Ala Ile Val Pro Gln Gly Thr Leu Lys
                245                 250                 255

Cys Lys Ile Gly Lys Thr Thr Val Gln Val Ile Ala Met Asp Thr Lys
            260                 265                 270

Leu Gly Pro Met Pro Cys Arg Pro Tyr Glu Ile Ile Ser Ser Glu Gly
        275                 280                 285

Pro Val Glu Lys Thr Ala Cys Thr Phe Asn Tyr Thr Lys Thr Leu Lys
    290                 295                 300

Asn Lys Tyr Phe Glu Pro Arg Asp Ser Tyr Phe Gln Gln Tyr Met Leu
305                 310                 315                 320

Lys Gly Glu Tyr Gln Tyr Trp Phe Asp Leu Glu Val Thr Asp His His
                325                 330                 335

Arg Asp Tyr Phe Ala Glu Ser Ile Leu Val Val Val Val Ala Leu Leu
            340                 345                 350

Gly Gly Arg Tyr Val Leu Trp Leu Leu Val Thr Tyr Met Val Leu Ser
        355                 360                 365

Glu Gln Lys Ala Leu Gly
    370
```

<210> SEQ ID NO 6
<211> LENGTH: 70
<212> TYPE: PRT
<213> ORGANISM: Bovine viral diarrhea virus

<400> SEQUENCE: 6

```
Ile Gln Tyr Gly Ser Gly Glu Val Val Met Met Gly Asn Leu Leu Thr
1               5                   10                  15

His Asn Asn Ile Glu Val Val Thr Tyr Phe Leu Leu Leu Tyr Leu Leu
            20                  25                  30

Leu Arg Glu Glu Ser Val Lys Lys Trp Val Leu Leu Leu Tyr His Ile
        35                  40                  45

Leu Val Val His Pro Ile Lys Ser Val Ile Val Ile Leu Leu Met Ile
    50                  55                  60

Gly Asp Val Val Lys Ala
65                  70
```

<210> SEQ ID NO 7

-continued

```
<211> LENGTH: 12301
<212> TYPE: DNA
<213> ORGANISM: Swine fever virus
<220> FEATURE:
<221> NAME/KEY: CDS
<222> LOCATION: (878)..(1174)
<223> OTHER INFORMATION: core protein
<220> FEATURE:
<221> NAME/KEY: CDS
<222> LOCATION: (1175)..(1855)
<223> OTHER INFORMATION: E-rns protein
<220> FEATURE:
<221> NAME/KEY: CDS
<222> LOCATION: (1856)..(2440)
<223> OTHER INFORMATION: E1 protein
<220> FEATURE:
<221> NAME/KEY: CDS
<222> LOCATION: (2441)..(3559)
<223> OTHER INFORMATION: E2 protein
<220> FEATURE:
<221> NAME/KEY: CDS
<222> LOCATION: (3560)..(3769)
<223> OTHER INFORMATION: p7 protein

<400> SEQUENCE: 7

gtatacgagg ttagttcatt ctcgtatgca tgattggaca aatcaaaatt tcaatttggt     60

tcagggcctc cctccagcga cggccgaact gggctagcca tgcccacagt aggactagca    120

aacggaggga ctagccgtag tggcgagctc cctgggtggt ctaagtcctg agtacaggac    180

agtcgtcagt agttcgacgt gagcagaagc ccacctcgag atgctatgtg gacgagggca    240

tgcccaagac acaccttaac cctagcgggg gtcgctaggg tgaaatcaca ccacgtgatg    300

ggagtacgac ctgatagggc gctgcagagg cccactatta ggctagtata aaaatctctg    360

ctgtacatgg cacatggagt tgaatcattt tgaactttta tacaaaacaa acaaacaaaa    420

accaatggga gtggaggaac cggtatacga tgccacgggg aggccattgt ttggagaccc    480

gagtgaggta cacccacaat caacactgaa gctaccacat gataggggga gaggtaacat    540

caaaacaaca ctgaagaacc tacctaggaa aggcgactgc aggagtggca accatctagg    600

cccggttagt gggatatatg taaagcccgg ccctgtcttt tatcaggact acatgggccc    660

ggtctaccat agagcccctc tagagttttt taacgaagcg cagttttgcg aggtgaccaa    720

aaggataggt agggtgacag gtagtgacgg aaagctttac catatatatg tgtgcatcga    780

tggttgcata ctgctgaagc tagccaagag ggacgagcca agaaccctga agtggattag    840

aaatttcacc gactgtccat tgtgggttac cagttgc tct gat gat ggc gca agt     895
                                         Ser Asp Asp Gly Ala Ser
                                         1               5

gga agt aaa gag aag aag cca gat agg atc aac aaa ggc aaa tta aaa      943
Gly Ser Lys Glu Lys Lys Pro Asp Arg Ile Asn Lys Gly Lys Leu Lys
            10                  15                  20

ata gcc cca aaa gag cat gag aag gac agc aga act aag cca cct gac      991
Ile Ala Pro Lys Glu His Glu Lys Asp Ser Arg Thr Lys Pro Pro Asp
        25                  30                  35

gct acg att gta gtg gaa gga gta aaa tac cag gtt aaa aag aag ggt     1039
Ala Thr Ile Val Val Glu Gly Val Lys Tyr Gln Val Lys Lys Lys Gly
    40                  45                  50

aaa gtt aaa gga aag agt acc caa gac ggc ctg tac cac aac aag aat     1087
Lys Val Lys Gly Lys Ser Thr Gln Asp Gly Leu Tyr His Asn Lys Asn
55                  60                  65                  70

aaa cca cca gaa tct agg aag aaa tta gaa aaa gcc cta ttg gca tgg     1135
Lys Pro Pro Glu Ser Arg Lys Lys Leu Glu Lys Ala Leu Leu Ala Trp
                75                  80                  85

gcg gta ata gca att atg ttg tac caa cca gtt gaa gcc gaa aat ata     1183
```

-continued

```
Ala Val Ile Ala Ile Met Leu Tyr Gln Pro Val Glu Ala Glu Asn Ile
            90                  95                  100

act caa tgg aac ctg agt gac aac ggc act aat ggt atc cag cat gct      1231
Thr Gln Trp Asn Leu Ser Asp Asn Gly Thr Asn Gly Ile Gln His Ala
        105                 110                 115

atg tac ctt aga ggg gtt agc agg agc ttg cat ggg atc tgg ccg gaa      1279
Met Tyr Leu Arg Gly Val Ser Arg Ser Leu His Gly Ile Trp Pro Glu
    120                 125                 130

aaa ata tgc aaa gga gtc ccc acc tac ctg gcc aca gac acg gaa ctg      1327
Lys Ile Cys Lys Gly Val Pro Thr Tyr Leu Ala Thr Asp Thr Glu Leu
135                 140                 145                 150

aaa gaa ata cag gga atg atg gat gcc agc gag ggg aca aac tat acg      1375
Lys Glu Ile Gln Gly Met Met Asp Ala Ser Glu Gly Thr Asn Tyr Thr
                155                 160                 165

tgc tgt aag tta cag aga cat gaa tgg aac aaa cat gga tgg tgt aac      1423
Cys Cys Lys Leu Gln Arg His Glu Trp Asn Lys His Gly Trp Cys Asn
            170                 175                 180

tgg tac aat ata gac ccc tgg ata cag ttg atg aat aga acc caa gca      1471
Trp Tyr Asn Ile Asp Pro Trp Ile Gln Leu Met Asn Arg Thr Gln Ala
        185                 190                 195

aac ttg gca gaa ggc cct ccg gcc aag gag tgc gct gtg act tgc agg      1519
Asn Leu Ala Glu Gly Pro Pro Ala Lys Glu Cys Ala Val Thr Cys Arg
    200                 205                 210

tac gat aaa gat gct gac atc aac gtg gtc acc cag gcc aga aac agg      1567
Tyr Asp Lys Asp Ala Asp Ile Asn Val Val Thr Gln Ala Arg Asn Arg
215                 220                 225                 230

cca aca acc ctg acc ggt tgc aag aaa gga aaa aat ttt tct ttt gcg      1615
Pro Thr Thr Leu Thr Gly Cys Lys Lys Gly Lys Asn Phe Ser Phe Ala
                235                 240                 245

ggt aca gtt ata gag ggc cca tgt aat ttc aat gtt tcc gtg gag gat      1663
Gly Thr Val Ile Glu Gly Pro Cys Asn Phe Asn Val Ser Val Glu Asp
            250                 255                 260

atc ttg tat ggg gat cat gag tgc ggc agt ttg ctt cag gac acg gct      1711
Ile Leu Tyr Gly Asp His Glu Cys Gly Ser Leu Leu Gln Asp Thr Ala
        265                 270                 275

ctg tac cta gtg gat gga atg acc aac act ata gag aat gcc aga cag      1759
Leu Tyr Leu Val Asp Gly Met Thr Asn Thr Ile Glu Asn Ala Arg Gln
    280                 285                 290

gga gca gcg agg gta aca tct tgg ctc ggg agg caa ctc agc act gcc      1807
Gly Ala Ala Arg Val Thr Ser Trp Leu Gly Arg Gln Leu Ser Thr Ala
295                 300                 305                 310

ggg aag agg ttg gag ggt aga agc aaa acc tgg ttt ggt gcc tat gcc      1855
Gly Lys Arg Leu Glu Gly Arg Ser Lys Thr Trp Phe Gly Ala Tyr Ala
                315                 320                 325

cta tcg cct tac tgt aat gta aca agc aaa ata ggg tac ata tgg tac      1903
Leu Ser Pro Tyr Cys Asn Val Thr Ser Lys Ile Gly Tyr Ile Trp Tyr
            330                 335                 340

act aac aac tgc acc ccg gct tgc ctc ccc aaa aat aca aag ata ata      1951
Thr Asn Asn Cys Thr Pro Ala Cys Leu Pro Lys Asn Thr Lys Ile Ile
        345                 350                 355

ggc ccc gga aaa ttt gac act aac gcg gaa gac gga aag att ctc cat      1999
Gly Pro Gly Lys Phe Asp Thr Asn Ala Glu Asp Gly Lys Ile Leu His
    360                 365                 370

gag atg ggg ggt cac cta tca gaa ttt ctg ctg ctc tct ctg gtt gtt      2047
Glu Met Gly Gly His Leu Ser Glu Phe Leu Leu Leu Ser Leu Val Val
375                 380                 385                 390

ctg tct gac ttc gcc cct gaa aca gcc agc gcg tta tac ctc att ttg      2095
Leu Ser Asp Phe Ala Pro Glu Thr Ala Ser Ala Leu Tyr Leu Ile Leu
                395                 400                 405
```

-continued

```
cac tac atg att cct caa tcc cat gaa gaa cct gaa ggc tgc gac aca      2143
His Tyr Met Ile Pro Gln Ser His Glu Glu Pro Glu Gly Cys Asp Thr
            410                 415                 420

aac cag ctg aat cta aca gtg gaa ctc agg act gaa gac gta ata ccg      2191
Asn Gln Leu Asn Leu Thr Val Glu Leu Arg Thr Glu Asp Val Ile Pro
        425                 430                 435

tca tca gtc tgg aat gtt ggc aaa tat gtg tgt gtt aga cca gac tgg      2239
Ser Ser Val Trp Asn Val Gly Lys Tyr Val Cys Val Arg Pro Asp Trp
    440                 445                 450

tgg cca tat gaa acc aag gtg gct ttg tta ttt gaa gag gca gga cag      2287
Trp Pro Tyr Glu Thr Lys Val Ala Leu Leu Phe Glu Glu Ala Gly Gln
455                 460                 465                 470

gtc gta aaa tta gcc tta cga gcg ctg agg gat tta acc agg gtc tgg      2335
Val Val Lys Leu Ala Leu Arg Ala Leu Arg Asp Leu Thr Arg Val Trp
                475                 480                 485

aat agc gca tca acc acg gca ttc ctc atc tgc ttg ata aaa gta tta      2383
Asn Ser Ala Ser Thr Thr Ala Phe Leu Ile Cys Leu Ile Lys Val Leu
            490                 495                 500

aga gga cag atc gtg caa ggt gtg ata tgg ctg cta cta gta act ggg      2431
Arg Gly Gln Ile Val Gln Gly Val Ile Trp Leu Leu Leu Val Thr Gly
        505                 510                 515

gca caa ggc cgg cta gcc tgc aag gaa gat tac agg tac gca ata tca      2479
Ala Gln Gly Arg Leu Ala Cys Lys Glu Asp Tyr Arg Tyr Ala Ile Ser
    520                 525                 530

tcg acc aat gag ata ggg cta ctc ggg gcc gaa ggt ctc acc acc acc      2527
Ser Thr Asn Glu Ile Gly Leu Leu Gly Ala Glu Gly Leu Thr Thr Thr
535                 540                 545                 550

tgg aaa gaa tac aac cac gat ttg caa ctg aat gac ggg acc gtt aag      2575
Trp Lys Glu Tyr Asn His Asp Leu Gln Leu Asn Asp Gly Thr Val Lys
                555                 560                 565

gcc att tgc gtg gca ggt tcc ttt aaa gtc ata gca ctt aat gtg gtc      2623
Ala Ile Cys Val Ala Gly Ser Phe Lys Val Ile Ala Leu Asn Val Val
            570                 575                 580

agt agg agg tat ttg gca tca ttg cat aag gag gct tca ctc act tcc      2671
Ser Arg Arg Tyr Leu Ala Ser Leu His Lys Glu Ala Ser Leu Thr Ser
        585                 590                 595

gtg aca ttt gag ctc ctg ttc gac ggg acc aac cca tca act gag gaa      2719
Val Thr Phe Glu Leu Leu Phe Asp Gly Thr Asn Pro Ser Thr Glu Glu
    600                 605                 610

atg gga gat gac ttc ggg ttc ggg ctg tgc ccg ttc gat acg agt cct      2767
Met Gly Asp Asp Phe Gly Phe Gly Leu Cys Pro Phe Asp Thr Ser Pro
615                 620                 625                 630

gtt gtc aag gga aag tac aat aca acc ttg ttg aac ggt agt gct ttc      2815
Val Val Lys Gly Lys Tyr Asn Thr Thr Leu Leu Asn Gly Ser Ala Phe
                635                 640                 645

tat ctt gtc tgc cca ata ggg tgg acg ggt gtc ata gag tgc aca gca      2863
Tyr Leu Val Cys Pro Ile Gly Trp Thr Gly Val Ile Glu Cys Thr Ala
            650                 655                 660

gtg agc cca aca act ctg aga aca gaa gtg gta aag acc ttc agg aga      2911
Val Ser Pro Thr Thr Leu Arg Thr Glu Val Val Lys Thr Phe Arg Arg
        665                 670                 675

gac aag ccc ttt ccg cac aga atg gat tgt gcg acc acc aca gtg gaa      2959
Asp Lys Pro Phe Pro His Arg Met Asp Cys Ala Thr Thr Thr Val Glu
    680                 685                 690

aat gga gat tta ttc tac tgt aag ttg ggg ggc aac tgg aca tgt gtg      3007
Asn Gly Asp Leu Phe Tyr Cys Lys Leu Gly Gly Asn Trp Thr Cys Val
695                 700                 705                 710

aaa ggt gaa cca gtg gtc tac acg ggg ggg cta gta aaa caa tgc aga      3055
Lys Gly Glu Pro Val Val Tyr Thr Gly Gly Leu Val Lys Gln Cys Arg
                715                 720                 725
```

-continued

```
tgg tgt ggc ttc gac ttc aat gag ccc gac gga ctc ccg cac tac ccc     3103
Trp Cys Gly Phe Asp Phe Asn Glu Pro Asp Gly Leu Pro His Tyr Pro
            730                 735                 740

ata ggt aag tgc atc ttg gta aat gag aca ggt tac aga ata gta gat     3151
Ile Gly Lys Cys Ile Leu Val Asn Glu Thr Gly Tyr Arg Ile Val Asp
        745                 750                 755

tca acg gac tgt aac aga gat ggc gtt gta atc agc aca gat ggg agt     3199
Ser Thr Asp Cys Asn Arg Asp Gly Val Val Ile Ser Thr Asp Gly Ser
    760                 765                 770

cat gag tgc ttg atc ggt aac aca act gtc aag gtg cat gca tca gat     3247
His Glu Cys Leu Ile Gly Asn Thr Thr Val Lys Val His Ala Ser Asp
775                 780                 785                 790

gaa aga ctg ggc cct atg cca tgc aga ccc aaa gag att gtc tct agt     3295
Glu Arg Leu Gly Pro Met Pro Cys Arg Pro Lys Glu Ile Val Ser Ser
                795                 800                 805

gca gga cct gta agg aaa act tcc tgt aca ttc aac tac gca aaa act     3343
Ala Gly Pro Val Arg Lys Thr Ser Cys Thr Phe Asn Tyr Ala Lys Thr
            810                 815                 820

ttg aag aac aag tac tat gag ccc agg gac agc tac ttc cag caa tat     3391
Leu Lys Asn Lys Tyr Tyr Glu Pro Arg Asp Ser Tyr Phe Gln Gln Tyr
        825                 830                 835

atg ctt aag ggc gag tat cag tac tgg ttt gac ctg gac gtg act gac     3439
Met Leu Lys Gly Glu Tyr Gln Tyr Trp Phe Asp Leu Asp Val Thr Asp
    840                 845                 850

cgc cac tca gat tac ttc gca gaa ttt gtc gtc ttg gta gtg gta gca     3487
Arg His Ser Asp Tyr Phe Ala Glu Phe Val Val Leu Val Val Val Ala
855                 860                 865                 870

ctg tta gga gga aga tat gtc ctg tgg cta ata gtg acc tac ata gtt     3535
Leu Leu Gly Gly Arg Tyr Val Leu Trp Leu Ile Val Thr Tyr Ile Val
                875                 880                 885

cta aca gaa caa ctc gcc gct ggt tta cca ttg ggc cag ggt gag gta     3583
Leu Thr Glu Gln Leu Ala Ala Gly Leu Pro Leu Gly Gln Gly Glu Val
            890                 895                 900

gtg ttg ata ggg aac tta att acc cac aca gac att gag gtc gta gta     3631
Val Leu Ile Gly Asn Leu Ile Thr His Thr Asp Ile Glu Val Val Val
        905                 910                 915

tat ttc tta cta ctc tat ttg gtc atg agg gat gag cct ata aag aaa     3679
Tyr Phe Leu Leu Leu Tyr Leu Val Met Arg Asp Glu Pro Ile Lys Lys
    920                 925                 930

tgg ata ctg ctg ctg ttc cat gct atg act aac aat cca gtc aag acc     3727
Trp Ile Leu Leu Leu Phe His Ala Met Thr Asn Asn Pro Val Lys Thr
935                 940                 945                 950

ata aca gtg gca ttg ctt atg gtt agt ggg gtt gcc aag ggt             3769
Ile Thr Val Ala Leu Leu Met Val Ser Gly Val Ala Lys Gly
                955                 960

ggaaagatag acggcggttg gcagcggctg ccagagacca gctttgacat ccaactcgcg   3829

ctgacagtta tagtagtcgc tgtgatgtta ctggcaaaga gagatccaac tactgtcccc   3889

ttggttataa cagtggcaac cctgagaacg gctaagatga ctaatggact tagcacggat   3949

atagccatag ctacagtgtc aacagcgttg ctaacctgga cctacattag tgactattat   4009

agatacaaga cttggctaca gtaccttatt agcacagtga caggtatctt cttaataagg   4069

gtactgaagg gaataggtga gttggattta cacactccaa ccttgccatc ttacagaccc   4129

ctcttcttca ttctcgtgta cctcatttcc actgcagtgg taacaagatg gaatctggac   4189

atagccggat tgctgttgca gtgtgtccca acccttttga tggtttttac gatgtgggca   4249

gacattctca ccctgatcct catactgccc acttacgagc taacaaaact atattacctc   4309
```

-continued

```
aaggaagtga agactggggc agaaaagggc tggttatgga agaccaactt caagagggta   4369
aacgacatat acgaagttga ccaatctggt gaaggggttt accttttccc gtcaaaacaa   4429
aagacaagtt caataacagg taccatgttg ccattgatca aagccatact catcagctgc   4489
atcagtaata agtggcagtt catatatcta ttgtacttga tatttgaagt gtcttactac   4549
ctccacaaga agatcataga tgaaatagca ggagggacca acttcatctc aagacttgta   4609
gccgctttga tcgaagccaa ttgggccttt gacaacgaag aagttagggg tttaaagaag   4669
ttcttcctgt tgtctagtag ggttaaagaa ctgatcatca aacacaaagt gaggaatgaa   4729
gtaatggtcc actggtttgg tgacgaagag gtttatggga tgccaaagtt ggttggctta   4789
gtcaaggcag caacattgag taaaaataaa cattgtattt tgtgcaccgt ctgtgaagac   4849
agagagtgga gaggagaaac ctgcccaaaa tgcgggcgtt ttgggccacc aatgacctgt   4909
ggtatgaccc tagccgactt tgaagaaaaa cattataaga ggatcttttt tagagaggat   4969
caatcagaag ggccggttag agaggagtac gcagggtatc tgcaatatag agccagaggg   5029
caattattcc tgaggaatct cccggtgcta gcaacaaaag tcaagatgct cctggtcgga   5089
aatcttggga cggaggtggg agacttggaa caccttggct gggtccttag gggcctgcc   5149
gtttgcaaga aggttaccga acatgagaaa tgcaccacat ccataatgga caaattgact   5209
gctttttttcg gtgttatgcc aaggggcacc acacctagag cccctgtgag attcccccacc   5269
tctctcttaa agataagaag gggggttggaa actggctggg cgtacacaca ccaaggtggc   5329
attagttcag tggaccatgt cacttgtggg aaagacttgc tggtatgtga cactatgggc   5389
cggacaaggg tcgtttgcca atcaaataat aagatgacag atgagtctga gtatggagtt   5449
aaaactgact ccggatgccc ggaaggagct aggtgttatg tgttcaaccc agaggcagtt   5509
aacatatcag ggactaaagg agccatggtc cacttacaaa aaactggagg agaattcacc   5569
tgtgtgacag catcaggaac tccggccttc tttgatctca agaacctcaa aggctggtca   5629
gggctaccga tatttgaggc atcaagtgga agggtagtcg gcagggtcaa ggtcgggaag   5689
aatgaggact ctaaaccaac caagcttatg agtggaatac aaacagtctc caaaagtacc   5749
acagacttga cagaaatggt aaagaaaata acgaccatga acaggggaga attcagacaa   5809
ataacccttg ctacaggtgc cggaaaaacc acggaactcc ctaggtcagt catagaagag   5869
atagggaggc ataagagagt cttggtcttg atccctctga gggcggcagc agagtcagta   5929
taccaatata tgagacaaaa acatccaagc atcgcattta acctgaggat aggggagatg   5989
aaggaagggg acatggccac agggataacc tatgcttcat acggttactt ctgtcagatg   6049
ccacaaccta agttgcgagc cgcgatggtt gagtactcct tcatatttct tgacgagtac   6109
cactgtgcca ccccagaaca attggccatc atgggaaaga tccacagatt ttcagagaac   6169
ctgcgggtag tagccatgac cgcaacacca gcaggcacag taacaaccac agggcagaaa   6229
caccctatag aagaattcat agccccagaa gtgatgaaag gggaagactt aggctcagag   6289
tacttggaca ttgctggact aaagatacca gtagaggaga tgaagagcaa catgctggtt   6349
tttgtgccca ctaggaacat ggcggtggag acagcaaaga aattgaaagc taagggttac   6409
aactcaggct actattatag tggagaggat ccatctaacc tgagggtggt aacgtcgcag   6469
tccccgtacg tggtggtggc aaccaacgcg atagaatcag gtgttactct cccggacttg   6529
gatgtggttg tcgatacagg gcttaagtgt gaaaagagaa tacggctgtc acctaagatg   6589
cccttcatag tgacgggcct gaagagaatg gctgtcacga ttggggaaca agcccagaga   6649
agggggagag ttgggagagt aaagcctggg agatactaca ggagtcaaga aactcccgtt   6709
```

-continued

```
ggttctaaag attaccatta tgatctactg caagcacaga ggtacggtat tgaagatggg   6769
ataaacatca ccaaatcctt tagagagatg aactatgatt ggagccttta tgaggaggac   6829
agtctgatga ttacacaatt ggaaatcctc aataatttgt tgatatcaga agaactaccg   6889
atggcagtaa aaaatataat ggccaggact gaccacccag aaccaattca gctggcgtac   6949
aacagctacg aaacacaagt gccagtgcta ttcccaaaaa taaagaatgg agaggtgact   7009
gatagttacg ataactatac cttcctcaac gcaagaaaat tgggggatga tgtacccccct   7069
tacgtgtatg ccacagagga tgaggactta gcggtagagc tactgggctt agactggcca   7129
gaccctggaa accaaggaac cgtagaggct ggcagagcac taaaacaagt agttggtcta   7189
tcaacagctg agaatgccct gttagtagcc ttattcggct atgtaggata tcaggcactt   7249
tcaaagaggc atataccagt agtcacagat atatattcaa ttgaagatca caggttggaa   7309
gacaccacac acctacagta cgccccaaat gctatcaaga cggaggggaa ggagacagaa   7369
ttgaaggagc tagcccaggg ggatgtgcag agatgtgtgg aagctatgac caattatgca   7429
agagagggta tccaattcat gaagtctcag gcactgaagg tgaaagaaac ccccacttac   7489
aaagagacaa tgaacactgt gactgactat gtaaagaaat tcatggaggc gctggcagac   7549
agtaaagaag acatcttaag atatgggttg tgggggacgc acacagcctt atataagagc   7609
atcagtgcca ggcttgggag tgagactgcg ttcgctaccc tggtcgtgaa gtggctggca   7669
tttgggggg aatcaatagc agaccatgtc aaacaagcgg ccacagactt ggtcgtctac   7729
tatatcatca acagacctca gttcccagga gacacagaga cacaacagga aggaaggaaa   7789
tttgtggcca gcctactggt ctcagctcta gctacttaca catacaaaag ctggaattac   7849
aataatctgt ccaagatagt tgaaccggct ttggccactc tgccctatgc cgccacagct   7909
ctcaaactat tcgcccccac tcgattggag agcgttgtca tattgagtac cgcaatctac   7969
aagacctacc tatcaatcag gcgcggaaaa agcgatggtt tgctaggcac aggggttagt   8029
gcggctatgg agatcatgtc acaaaatcca gtatccgtgg gcatagcagt catgctaggg   8089
gtaggggccg tggcagccca caatgcaatc gaggccagtg agcagaagag aacactactc   8149
atgaaagttt ttgtaaagaa cttcttggac caagcagcca ctgatgaatt agtcaaggag   8209
agtcctgaga aaataataat ggctttgttt gaagcagtgc agacagtcgg taaccctctt   8269
agactagtat accaccttta tggagttttc tataaggggt gggaggcaaa agagttggcc   8329
caaaggacag ccggtaggaa ccttttcact ttgataatgt tcgaggctgt ggaactactg   8389
ggagtagata gtgaaggaaa gatccgccag ctatcaagta attacatact agagctcctg   8449
tataagttcc gtgacagtat caagtctagc gtgagggaga tggcaatcag ctgggcccct   8509
gcccctttca gctgtgattg gacaccgacg gatgacagaa tagggctccc ccaagacaat   8569
ttcctccaag tggagacgaa atgcccctgt ggttacaaga tgaaggcagt taagaattgt   8629
gctggagagc tgagactctt ggaggaggaa ggctcatttc tctgcagaaa taaattcggg   8689
agaggttcac ggaactacag ggtgacaaaa tactatgatg acaatctatc agaaataaag   8749
ccagtgataa gaatggaagg gcatgtggaa ctctactaca agggagccac catcaaactg   8809
gacttcaaca acagtaaaac aatactggca accgataaat gggagattga tcactccact   8869
ctggtcaggg tgctcaagag gcacacaggg gctggatatc atggggcata cctgggcgag   8929
aaaccgaact acaaacatct gatagagagg gactgtgcaa ccatcaccaa agataaggtt   8989
tgttttctca aaatgaagag agggtgtgca tttacttatg acttatccct tcacaacctt   9049
```

-continued

```
acccgactga ttgaattggt acacaagaat aacttggaag acaaagagat tcctgctgtt   9109
acggttacaa cctggctggc ttacacgttt gtaaatgaag atatagggac cataaaacca   9169
gccttcgggg agaaagtaac accggagatg caggaggaaa taaccttgca gcctgctgta   9229
gtggtggata caactgacgt gaccgtgact gtggtagggg aagcccctac tatgactaca   9289
ggggagactc cgacagcgtt caccagctca ggttcagacc cgaaaggcca acaagtttta   9349
aaactggggg taggtgaagg ccaataccc  gggactaatc cacagagggc aagcctgcac   9409
gaagccatac aaggtgcaga tgagagaccc tcggtgctga tattagggtc tgataaagcc   9469
acctctaata gagtgaaaac tgcaaagaat gtaaaggtat acagaggcag ggacccacta   9529
gaagtgagag atatgatgag gaggggaaag atcctggtca tagccctgtc tagggttgat   9589
aatgctctat tgaaatttgt tgactacaaa ggcacctttc taactagaga gaccctagag   9649
gcattaagtt tgggtaggcc taaaaagaaa aacataacca aggcagaagc gcagtggttg   9709
ctgtgcctcg aagaccaaat ggaagagcta cccgattggt tcgcagccgg ggaacccatt   9769
tttctagagg ctaacattaa acatgacagg taccatctgg tgggggatat agctaatatc   9829
aaggaaaaag ccaaacagtt gggagctaca gactccacaa agatatctaa ggaggttggt   9889
gcaaaagtgt attctatgaa actgagtaat tgggtgatgc aagaagaaaa taaacagggc   9949
aacctgaccc ccttgtttga agagctcctg caacagtgtc cacccggagg ccagaacaaa  10009
actgcacata tggtctctgc ttaccaacta gctcaaggga actggatgcc aaccagctgc  10069
catgttttta tggggaccat atctgccagg aggaccaaga cccatccata tgaagcatac  10129
gtcaagttaa gggagttggt agaggaacac aagatgaaaa cattgtgtcc tggatcaagc  10189
ctgggtaagc acaacgaatg gataattggt aaaatcaaat accagggaaa cctgaggacc  10249
aaacacatgt tgaaccccgg caaggtggca gagcaactgt gcagagaggg acacagacac  10309
aatgtgtata acaagacaat aggctcagta atgacagcta ctggtatcag gttggagaag  10369
ttgcccgtgg ttagggccca gacagacaca accaacttcc accaagcaat aagggataag  10429
atagacaagg aagagaacct acaaaccccg ggtttacata agaaactaat ggaagttttc  10489
aatgcattga aacgacccga gttagagtcc tcctacgatg ccgtggaatg ggaggaactg  10549
gagagaggaa taaacaggaa gggtgctgct ggtttctttg aacgcaaaaa tatagggggaa  10609
atattggatt cagagaaaaa caaagtcgaa gagattattg acaatctgaa aaaaggcaga  10669
aacatcaaat actatgaaac cgcgatccca aagaatgaga agagggacgt caatgatgac  10729
tggactgctg gtgacttcgt ggaagagaag aaacccagag tcatacaata ccctgaagca  10789
aaaacaaggc tggccatcac caaggtgatg tataagtggg tgaagcagaa gccagtagtt  10849
atacccgggt atgaagggaa gacacctcta ttccaaattt ttgacaaagt aaagaaggaa  10909
tgggatcaat tccaaaatcc agtggcagtg agttttgaca ctaaggcgtg ggacacccag  10969
gtaaccacaa aagatttgga gttgataaag gacatacaaa agtactattt caagaagaaa  11029
tggcataaat ttattgacac cctgaccatg cacatgtcag aagtacccgt aatcagtgct  11089
gatggggaag tatacataag gaaagggcaa agaggcagtg gacaacctga cacaagcgca  11149
ggcaatagca tgctaaatgt gttaacaatg atttacgcct tctgcgaggc cacgggagta  11209
ccctacaaga gcttcgacag ggtggcaaaa attcatgtgt gtggggatga tggtttcctg  11269
atcacagaaa gagctctcgg tgagaaattc gcgagtaagg gagtccagat cctatatgaa  11329
gctgggaagc cccagaagat cactgaaggg gacaagatga aagtggccta ccaatttgat  11389
gatattgagt tttgctccca tacaccaata caagtaaggt ggtcagataa cacttctagt  11449
```

-continued

```
tacatgccgg ggagaaatac aaccacaatc ctggctaaaa tggccacaag gttagattcc  11509

agtggtgaga ggggtaccat agcatatgag aaagcagtag cattcagctt cctgctgatg  11569

tactcctgga acccactaat cagaaggatc tgcttactgg tgctatcaac tgaactgcaa  11629

gtgaaaccag ggaagtcaac cacttactac tatgaagggg acccgatatc tgcctacaag  11689

gaagtcatcg gccacaatct ttttgatctt aagagaacaa gcttcgagaa gctggccaag  11749

ttaaatctca gcatgtcagt actcggagcc tggactagac acaccagtaa aagactacta  11809

caagactgtg tcaatgtggg tgttaaagag ggcaactggc tagttaatgc agatagacta  11869

gtaagtagca agactggaaa taggtacata cccggagagg gccacaccct gcaagggaga  11929

cattatgaag aactggtgtt ggcaagaaaa cagatcaaca actttcaagg gaccgacagg  11989

tacaatctag gcccaatagt caatatggtg ttaaggaggc tgagagtcat gatgatgacc  12049

ctgataggga gaggggtatg agcgcgggta acccgggatc tggacccgcc agtagaaccc  12109

tgttgtagat aacactaatt tttttttatt tatttagata ttactattta tttatttatt  12169

tatttattga atgagtaaga actggtacaa actacctcaa gttaccacac tacactcatt  12229

tttaacagca ctttagctgg aaggaaaatt cctgacgtcc acagttggac taaggtaatt  12289

tcctaacggc cc                                                      12301
```

```
<210> SEQ ID NO 8
<211> LENGTH: 99
<212> TYPE: PRT
<213> ORGANISM: Swine fever virus

<400> SEQUENCE: 8

Ser Asp Asp Gly Ala Ser Gly Ser Lys Glu Lys Lys Pro Asp Arg Ile
1               5                   10                  15

Asn Lys Gly Lys Leu Lys Ile Ala Pro Lys Glu His Glu Lys Asp Ser
            20                  25                  30

Arg Thr Lys Pro Pro Asp Ala Thr Ile Val Val Glu Gly Val Lys Tyr
        35                  40                  45

Gln Val Lys Lys Lys Gly Lys Val Lys Gly Lys Ser Thr Gln Asp Gly
    50                  55                  60

Leu Tyr His Asn Lys Asn Lys Pro Pro Glu Ser Arg Lys Lys Leu Glu
65                  70                  75                  80

Lys Ala Leu Leu Ala Trp Ala Val Ile Ala Ile Met Leu Tyr Gln Pro
                85                  90                  95

Val Glu Ala


<210> SEQ ID NO 9
<211> LENGTH: 227
<212> TYPE: PRT
<213> ORGANISM: Swine fever virus

<400> SEQUENCE: 9

Glu Asn Ile Thr Gln Trp Asn Leu Ser Asp Asn Gly Thr Asn Gly Ile
1               5                   10                  15

Gln His Ala Met Tyr Leu Arg Gly Val Ser Arg Ser Leu His Gly Ile
            20                  25                  30

Trp Pro Glu Lys Ile Cys Lys Gly Val Pro Thr Tyr Leu Ala Thr Asp
        35                  40                  45

Thr Glu Leu Lys Glu Ile Gln Gly Met Met Asp Ala Ser Glu Gly Thr
    50                  55                  60
```

-continued

Asn Tyr Thr Cys Cys Lys Leu Gln Arg His Glu Trp Asn Lys His Gly
65 70 75 80

Trp Cys Asn Trp Tyr Asn Ile Asp Pro Trp Ile Gln Leu Met Asn Arg
85 90 95

Thr Gln Ala Asn Leu Ala Glu Gly Pro Pro Ala Lys Glu Cys Ala Val
100 105 110

Thr Cys Arg Tyr Asp Lys Asp Ala Asp Ile Asn Val Val Thr Gln Ala
115 120 125

Arg Asn Arg Pro Thr Thr Leu Thr Gly Cys Lys Lys Gly Lys Asn Phe
130 135 140

Ser Phe Ala Gly Thr Val Ile Glu Gly Pro Cys Asn Phe Asn Val Ser
145 150 155 160

Val Glu Asp Ile Leu Tyr Gly Asp His Glu Cys Gly Ser Leu Leu Gln
165 170 175

Asp Thr Ala Leu Tyr Leu Val Asp Gly Met Thr Asn Thr Ile Glu Asn
180 185 190

Ala Arg Gln Gly Ala Ala Arg Val Thr Ser Trp Leu Gly Arg Gln Leu
195 200 205

Ser Thr Ala Gly Lys Arg Leu Glu Gly Arg Ser Lys Thr Trp Phe Gly
210 215 220

Ala Tyr Ala
225

<210> SEQ ID NO 10
<211> LENGTH: 195
<212> TYPE: PRT
<213> ORGANISM: Swine fever virus

<400> SEQUENCE: 10

Leu Ser Pro Tyr Cys Asn Val Thr Ser Lys Ile Gly Tyr Ile Trp Tyr
1 5 10 15

Thr Asn Asn Cys Thr Pro Ala Cys Leu Pro Lys Asn Thr Lys Ile Ile
20 25 30

Gly Pro Gly Lys Phe Asp Thr Asn Ala Glu Asp Gly Lys Ile Leu His
35 40 45

Glu Met Gly Gly His Leu Ser Glu Phe Leu Leu Leu Ser Leu Val Val
50 55 60

Leu Ser Asp Phe Ala Pro Glu Thr Ala Ser Ala Leu Tyr Leu Ile Leu
65 70 75 80

His Tyr Met Ile Pro Gln Ser His Glu Glu Pro Glu Gly Cys Asp Thr
85 90 95

Asn Gln Leu Asn Leu Thr Val Glu Leu Arg Thr Glu Asp Val Ile Pro
100 105 110

Ser Ser Val Trp Asn Val Gly Lys Tyr Val Cys Val Arg Pro Asp Trp
115 120 125

Trp Pro Tyr Glu Thr Lys Val Ala Leu Leu Phe Glu Glu Ala Gly Gln
130 135 140

Val Val Lys Leu Ala Leu Arg Ala Leu Arg Asp Leu Thr Arg Val Trp
145 150 155 160

Asn Ser Ala Ser Thr Thr Ala Phe Leu Ile Cys Leu Ile Lys Val Leu
165 170 175

Arg Gly Gln Ile Val Gln Gly Val Ile Trp Leu Leu Leu Val Thr Gly
180 185 190

Ala Gln Gly
195

<210> SEQ ID NO 11
<211> LENGTH: 373
<212> TYPE: PRT
<213> ORGANISM: Swine fever virus

<400> SEQUENCE: 11

```
Arg Leu Ala Cys Lys Glu Asp Tyr Arg Tyr Ala Ile Ser Ser Thr Asn
1               5                   10                  15

Glu Ile Gly Leu Leu Gly Ala Glu Gly Leu Thr Thr Thr Trp Lys Glu
            20                  25                  30

Tyr Asn His Asp Leu Gln Leu Asn Asp Gly Thr Val Lys Ala Ile Cys
        35                  40                  45

Val Ala Gly Ser Phe Lys Val Ile Ala Leu Asn Val Val Ser Arg Arg
    50                  55                  60

Tyr Leu Ala Ser Leu His Lys Glu Ala Ser Leu Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Gly Phe Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
        115                 120                 125

Cys Pro Ile Gly Trp Thr Gly Val Ile Glu Cys Thr Ala Val Ser Pro
    130                 135                 140

Thr Thr Leu Arg Thr Glu Val Val Lys Thr Phe Arg Arg Asp Lys Pro
145                 150                 155                 160

Phe Pro His Arg Met Asp Cys Ala Thr Thr Thr Val Glu Asn Gly Asp
                165                 170                 175

Leu Phe Tyr Cys Lys Leu Gly Gly Asn Trp Thr Cys Val Lys Gly Glu
            180                 185                 190

Pro Val Val Tyr Thr Gly Gly Leu Val Lys Gln Cys Arg Trp Cys Gly
        195                 200                 205

Phe Asp Phe Asn Glu Pro Asp Gly Leu Pro His Tyr Pro Ile Gly Lys
    210                 215                 220

Cys Ile Leu Val Asn Glu Thr Gly Tyr Arg Ile Val Asp Ser Thr Asp
225                 230                 235                 240

Cys Asn Arg Asp Gly Val Val Ile Ser Thr Asp Gly Ser His Glu Cys
                245                 250                 255

Leu Ile Gly Asn Thr Thr Val Lys Val His Ala Ser Asp Glu Arg Leu
            260                 265                 270

Gly Pro Met Pro Cys Arg Pro Lys Glu Ile Val Ser Ser Ala Gly Pro
        275                 280                 285

Val Arg Lys Thr Ser Cys Thr Phe Asn Tyr Ala Lys Thr Leu Lys Asn
    290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp Arg His Ser
                325                 330                 335

Asp Tyr Phe Ala Glu Phe Val Val Leu Val Val Val Ala Leu Leu Gly
            340                 345                 350

Gly Arg Tyr Val Leu Trp Leu Ile Val Thr Tyr Ile Val Leu Thr Glu
        355                 360                 365

Gln Leu Ala Ala Gly
```

-continued

370

<210> SEQ ID NO 12
<211> LENGTH: 70
<212> TYPE: PRT
<213> ORGANISM: Swine fever virus

<400> SEQUENCE: 12

```
Leu Pro Leu Gly Gln Gly Glu Val Val Leu Ile Gly Asn Leu Ile Thr
1               5                   10                  15

His Thr Asp Ile Glu Val Val Val Tyr Phe Leu Leu Leu Tyr Leu Val
            20                  25                  30

Met Arg Asp Glu Pro Ile Lys Lys Trp Ile Leu Leu Leu Phe His Ala
        35                  40                  45

Met Thr Asn Asn Pro Val Lys Thr Ile Thr Val Ala Leu Leu Met Val
    50                  55                  60

Ser Gly Val Ala Lys Gly
65                  70
```

<210> SEQ ID NO 13
<211> LENGTH: 12333
<212> TYPE: DNA
<213> ORGANISM: Border disease virus
<220> FEATURE:
<221> NAME/KEY: CDS
<222> LOCATION: (877)..(1176)
<223> OTHER INFORMATION: core protein
<220> FEATURE:
<221> NAME/KEY: CDS
<222> LOCATION: (1177)..(1857)
<223> OTHER INFORMATION: E-rns protein
<220> FEATURE:
<221> NAME/KEY: CDS
<222> LOCATION: (1858)..(2442)
<223> OTHER INFORMATION: E1 protein
<220> FEATURE:
<221> NAME/KEY: CDS
<222> LOCATION: (2443)..(3561)
<223> OTHER INFORMATION: E2 protein
<220> FEATURE:
<221> NAME/KEY: CDS
<222> LOCATION: (3562)..(3771)
<223> OTHER INFORMATION: p7 protein

<400> SEQUENCE: 13

```
gtatacggga gtagctcatg cccgtataca aaattggata ttccaaaact cgattgggtt      60

agggagccct cctagcgacg gccgaaccgt gttaaccata cacgtagtag gactagcaga     120

cgggaggact agccatcgtg gtgagatccc tgagcagtct aaatcctgag tacaggatag     180

tcgtcagtag ttcaacgcag gcacggttct gccttgagat gctacgtgga cgagggcatg     240

cccaagactt gctttaatct cggcgggggt cgccgaggtg aaaacaccta acggtgttgg     300

ggttacagcc tgatagggtg ctgcagaggc ccacgaatag gctagtataa aaatctctgc     360

tgtacatggc acatggagtt gaacaagttt gaacttttat acaaaacaag taaacaaaaa     420

ccagtggggg tgactgaacc tatctacgac tcagcgggta accccatata tggtgaaaga     480

agcacaatac acccgcagtc taccctgaaa ctaccacatg agagaggagt ggcagaagtc     540

gtaacgacac tgagagatct accaaagaaa ggtgactgca gaagtgggaa ccaccgaggt     600

ccagtaagtg gcatatatat caaaccagga ccagtcctct accaggatta caaggggcct     660

gtataccata gagcaccact ggaacttttt gttgagacgc aattctgtga agtcacaaag     720

aggataggga gagtgactgg tagtgacggc aggctttatc acttgtacat ttgctccgat     780
```

-continued

```
gggtgcatcc tattgaaaac agcaagtaag acaaggagtg cagtattaaa gtggacacgt    840

aatatccttg actgcccact gtgggtgaca agttgc tct gat gac aac aag agc      894
                                        Ser Asp Asp Asn Lys Ser
                                        1               5

gaa aag acg aat gag aaa aaa cca gat aga gtc agg cgg gga gcc atg      942
Glu Lys Thr Asn Glu Lys Lys Pro Asp Arg Val Arg Arg Gly Ala Met
            10                  15                  20

aag atc aca ccc aaa gag agt gag aag gat agt aga tct aag cca cct      990
Lys Ile Thr Pro Lys Glu Ser Glu Lys Asp Ser Arg Ser Lys Pro Pro
        25                  30                  35

gac gca act ata gta gta gaa ggc ata aaa tac cag gta aag aag aaa     1038
Asp Ala Thr Ile Val Val Glu Gly Ile Lys Tyr Gln Val Lys Lys Lys
    40                  45                  50

gga aag gtg aag ggc aag aac aca caa gat ggc tta tac cac aac aag     1086
Gly Lys Val Lys Gly Lys Asn Thr Gln Asp Gly Leu Tyr His Asn Lys
55                  60                  65                  70

aac aag cca cct gag tct aga aag aaa ttg gag aaa gcc cta ctg gct     1134
Asn Lys Pro Pro Glu Ser Arg Lys Lys Leu Glu Lys Ala Leu Leu Ala
                75                  80                  85

tgg gct ata ata gca atc ttc atg tgg gaa ccc gta gca cca gag aat     1182
Trp Ala Ile Ile Ala Ile Phe Met Trp Glu Pro Val Ala Pro Glu Asn
            90                  95                  100

gtg aca caa tgg aac cta agt gac aac ggg act acc ggc atc caa ctc     1230
Val Thr Gln Trp Asn Leu Ser Asp Asn Gly Thr Thr Gly Ile Gln Leu
        105                 110                 115

cta atg ttc caa aga ggt gtt aac aga agc ctg cac ggt att tgg cct     1278
Leu Met Phe Gln Arg Gly Val Asn Arg Ser Leu His Gly Ile Trp Pro
    120                 125                 130

gaa aag ata tgt aca gga gtg ccc acg cac ttg gca aca gat gca gag     1326
Glu Lys Ile Cys Thr Gly Val Pro Thr His Leu Ala Thr Asp Ala Glu
135                 140                 145                 150

ttg aaa gga att caa ggg atg atg gat gct agt gaa aag act aat tac     1374
Leu Lys Gly Ile Gln Gly Met Met Asp Ala Ser Glu Lys Thr Asn Tyr
                155                 160                 165

aca tgc tgc aga ctt cag aga cac gaa tgg aac aag tac ggg tgg tgc     1422
Thr Cys Cys Arg Leu Gln Arg His Glu Trp Asn Lys Tyr Gly Trp Cys
            170                 175                 180

aac tgg tac aac ata aat cca tgg ata tgg ttg atg aac aag aca caa     1470
Asn Trp Tyr Asn Ile Asn Pro Trp Ile Trp Leu Met Asn Lys Thr Gln
        185                 190                 195

gcc aat ctg acg gaa gga cct cca gaa aaa gaa tgc gct gtg acc tgt     1518
Ala Asn Leu Thr Glu Gly Pro Pro Glu Lys Glu Cys Ala Val Thr Cys
    200                 205                 210

agg ttc gat aag gaa gca gat ata aat ata gtg aca cag gct agg gac     1566
Arg Phe Asp Lys Glu Ala Asp Ile Asn Ile Val Thr Gln Ala Arg Asp
215                 220                 225                 230

agg cca aca act tta aca ggg tgt aag aaa gga aaa aaa ttt tca ttt     1614
Arg Pro Thr Thr Leu Thr Gly Cys Lys Lys Gly Lys Lys Phe Ser Phe
                235                 240                 245

gct ggc atg ata att gag ggc cct tgc aac ttc aat gta tca gtg gaa     1662
Ala Gly Met Ile Ile Glu Gly Pro Cys Asn Phe Asn Val Ser Val Glu
            250                 255                 260

gat ata tta ttc gga gac aat gag tgt agt agc tta ttc cag gac aca     1710
Asp Ile Leu Phe Gly Asp Asn Glu Cys Ser Ser Leu Phe Gln Asp Thr
        265                 270                 275

gct ctc tac gtg gta gat gga gta acc aac acc gta gaa aat gct agg     1758
Ala Leu Tyr Val Val Asp Gly Val Thr Asn Thr Val Glu Asn Ala Arg
    280                 285                 290

caa ggg gct gca aaa ttg aca tcc tgg cta ggg aag caa ttg ggt ata     1806
```

-continued

```
Gln Gly Ala Ala Lys Leu Thr Ser Trp Leu Gly Lys Gln Leu Gly Ile
295                 300                 305                 310

atg ggg aaa aaa tta gaa cac aag agt aaa acg tgg ttc gga gcc aat      1854
Met Gly Lys Lys Leu Glu His Lys Ser Lys Thr Trp Phe Gly Ala Asn
                315                 320                 325

gca caa tca cct tac tgt aat gta aca aga aaa ata ggg tac gtc tgg      1902
Ala Gln Ser Pro Tyr Cys Asn Val Thr Arg Lys Ile Gly Tyr Val Trp
            330                 335                 340

tac aca aac aat tgc acc cct gct tgc ctc cca aag aat aca aaa ata      1950
Tyr Thr Asn Asn Cys Thr Pro Ala Cys Leu Pro Lys Asn Thr Lys Ile
        345                 350                 355

ata ggt ccg ggg aaa ttt gac acc aat gcg gag gat gga aag atc ttg      1998
Ile Gly Pro Gly Lys Phe Asp Thr Asn Ala Glu Asp Gly Lys Ile Leu
    360                 365                 370

cat gag atg agg ggt cat ata tcg gaa ttc att cta cta tct ttg gta      2046
His Glu Met Arg Gly His Ile Ser Glu Phe Ile Leu Leu Ser Leu Val
375                 380                 385                 390

gtg cta tca gac ttc gca cct gaa aca gct agt act ctc tac ctg gtg      2094
Val Leu Ser Asp Phe Ala Pro Glu Thr Ala Ser Thr Leu Tyr Leu Val
                395                 400                 405

cta cat ttt gcc tta cct caa acc cac gaa gtt cct agt gta tgt gac      2142
Leu His Phe Ala Leu Pro Gln Thr His Glu Val Pro Ser Val Cys Asp
            410                 415                 420

acc aac caa cta aat ctt acg gtc agc ttg aga gtg gat gac gtg ata      2190
Thr Asn Gln Leu Asn Leu Thr Val Ser Leu Arg Val Asp Asp Val Ile
        425                 430                 435

cca tct tca gta tgg aac ctg gga aaa tat gtc tgt gtt aga cca gac      2238
Pro Ser Ser Val Trp Asn Leu Gly Lys Tyr Val Cys Val Arg Pro Asp
    440                 445                 450

tgg tgg ccc tat gaa aca acc atg gta ttg ttg ttt gaa gag gca gga      2286
Trp Trp Pro Tyr Glu Thr Thr Met Val Leu Leu Phe Glu Glu Ala Gly
455                 460                 465                 470

caa gta gtg aag ttg gta cta agg gcc ata agg gac ttg aca agg gtc      2334
Gln Val Val Lys Leu Val Leu Arg Ala Ile Arg Asp Leu Thr Arg Val
                475                 480                 485

tgg aac agt gca tca aca aca gcc ttt ctt ata tgc cta gtt aag gtg      2382
Trp Asn Ser Ala Ser Thr Thr Ala Phe Leu Ile Cys Leu Val Lys Val
            490                 495                 500

tta aga ggc cag gta gta cag gga cta gtg tgg cta tta ctg gta act      2430
Leu Arg Gly Gln Val Val Gln Gly Leu Val Trp Leu Leu Leu Val Thr
        505                 510                 515

ggt gca caa ggg cag ttt gct tgt aga gaa gac tac agg tat gct tta      2478
Gly Ala Gln Gly Gln Phe Ala Cys Arg Glu Asp Tyr Arg Tyr Ala Leu
    520                 525                 530

gca aga aca aag gaa ata ggg gcc ctg ggt gca gag agc ttg aca acg      2526
Ala Arg Thr Lys Glu Ile Gly Ala Leu Gly Ala Glu Ser Leu Thr Thr
535                 540                 545                 550

acc tgg act gac tac cga gga aac cta gaa ctg gac gat gga act gtg      2574
Thr Trp Thr Asp Tyr Arg Gly Asn Leu Glu Leu Asp Asp Gly Thr Val
                555                 560                 565

agg gcc aca tgt tcg aga ggt ttc ttt agg ttt aga gga cat tgc atg      2622
Arg Ala Thr Cys Ser Arg Gly Phe Phe Arg Phe Arg Gly His Cys Met
            570                 575                 580

ata ggg ccc agg tac ctg gct agc cta cac ctg agg gct cta ccc aca      2670
Ile Gly Pro Arg Tyr Leu Ala Ser Leu His Leu Arg Ala Leu Pro Thr
        585                 590                 595

tct gtc acc ttt gaa cta ata cca gga ggg tca gcg atg aca gaa gag      2718
Ser Val Thr Phe Glu Leu Ile Pro Gly Gly Ser Ala Met Thr Glu Glu
    600                 605                 610
```

-continued

```
gaa atg ggt gac gac ttt gaa ttc ggc ctg tgc cct tgt gat tct aga      2766
Glu Met Gly Asp Asp Phe Glu Phe Gly Leu Cys Pro Cys Asp Ser Arg
615                 620                 625                 630

ccc gtt gtt aag gga aaa tac aac acc act ctg ctc aac gga agt gcg      2814
Pro Val Val Lys Gly Lys Tyr Asn Thr Thr Leu Leu Asn Gly Ser Ala
                635                 640                 645

ttc caa cta ata tgc cct tac gga tgg gtc gga cgc gtg gag tgc act      2862
Phe Gln Leu Ile Cys Pro Tyr Gly Trp Val Gly Arg Val Glu Cys Thr
            650                 655                 660

act gta agc aag agc acc ctg gca aca gag gtg gta aag ata tac aaa      2910
Thr Val Ser Lys Ser Thr Leu Ala Thr Glu Val Val Lys Ile Tyr Lys
        665                 670                 675

aag aca aaa cca ttt cca cag cgg gtt ggt tgc gac cac acc acc gtc      2958
Lys Thr Lys Pro Phe Pro Gln Arg Val Gly Cys Asp His Thr Thr Val
    680                 685                 690

tac aaa caa gac ctg tac cat tgc cag atg gga ggt aac tgg acg tgc      3006
Tyr Lys Gln Asp Leu Tyr His Cys Gln Met Gly Gly Asn Trp Thr Cys
695                 700                 705                 710

atg aga ggt gaa gta gtc aaa tat gtg ggg ggt cca gta aag aag tgt      3054
Met Arg Gly Glu Val Val Lys Tyr Val Gly Gly Pro Val Lys Lys Cys
                715                 720                 725

gag tgg tgc ggc tac gtg ttt aag aag aga gag ggt ctc cca cac tat      3102
Glu Trp Cys Gly Tyr Val Phe Lys Lys Arg Glu Gly Leu Pro His Tyr
            730                 735                 740

cca att ggt agg tgt atg cta aga aac gag act ggt tac aga agc gtg      3150
Pro Ile Gly Arg Cys Met Leu Arg Asn Glu Thr Gly Tyr Arg Ser Val
        745                 750                 755

gat gac aca cca tgc gat aga ggt gga gtc gtg atc agc aaa acc ggt      3198
Asp Asp Thr Pro Cys Asp Arg Gly Gly Val Val Ile Ser Lys Thr Gly
    760                 765                 770

gag ctg gaa tgc tta ata ggt aag act aca gtg aaa gta ttt agc tcg      3246
Glu Leu Glu Cys Leu Ile Gly Lys Thr Thr Val Lys Val Phe Ser Ser
775                 780                 785                 790

gat aaa aaa ttg gga cct atg cca tgc aga cca aaa gaa gtc ata tcc      3294
Asp Lys Lys Leu Gly Pro Met Pro Cys Arg Pro Lys Glu Val Ile Ser
                795                 800                 805

agt gaa gga ccg gtc agc aag ata gct tgc aca ttc aac tac tca aaa      3342
Ser Glu Gly Pro Val Ser Lys Ile Ala Cys Thr Phe Asn Tyr Ser Lys
            810                 815                 820

acc ctg gaa aac aaa tac tat gag ccc aga gac agt tat ttc cag caa      3390
Thr Leu Glu Asn Lys Tyr Tyr Glu Pro Arg Asp Ser Tyr Phe Gln Gln
        825                 830                 835

tac atg ctc aag gga caa tac caa tac tgg ttc gat ctt gaa gca aca      3438
Tyr Met Leu Lys Gly Gln Tyr Gln Tyr Trp Phe Asp Leu Glu Ala Thr
    840                 845                 850

gat cac cac tca gat tac ttt gca gag ttc atc atg ttg gca gtg gta      3486
Asp His His Ser Asp Tyr Phe Ala Glu Phe Ile Met Leu Ala Val Val
855                 860                 865                 870

gcc ctg cta ggg ggg agg tat gtc tta tgg tta atg gtt gtc tac atg      3534
Ala Leu Leu Gly Gly Arg Tyr Val Leu Trp Leu Met Val Val Tyr Met
                875                 880                 885

atc ctg gca gat caa atg acc tca gca ata aac ctg ggc caa gga gag      3582
Ile Leu Ala Asp Gln Met Thr Ser Ala Ile Asn Leu Gly Gln Gly Glu
            890                 895                 900

gtg gtt ctg ata gga aat tta ata aca cat gag gac cat gag gtg gta      3630
Val Val Leu Ile Gly Asn Leu Ile Thr His Glu Asp His Glu Val Val
        905                 910                 915

gta tat ttc ctc ctg tta tac tta ata gtg aag gat gag cca gta aag      3678
Val Tyr Phe Leu Leu Leu Tyr Leu Ile Val Lys Asp Glu Pro Val Lys
    920                 925                 930
```

-continued

```
aag tgg ata ttg ttc ctc ttt cat gct atg acc aac aac cct gta aag     3726
Lys Trp Ile Leu Phe Leu Phe His Ala Met Thr Asn Asn Pro Val Lys
935                 940                 945                 950

aca ata tca gtt gga ctg cta atg tta agt ggg cta gtg aag ggg         3771
Thr Ile Ser Val Gly Leu Leu Met Leu Ser Gly Leu Val Lys Gly
                955                 960                 965

gaaggggcag gaatgaccta ctgggagggc ctcgacctgc agtttacctt gctggtaatg   3831

ataactgcat cactattagt ggcaagaagg gacgttacca catacccttt gataataaca   3891

gtgatagcat taaagaccac ctgggtgaat agtggcccgg ggattgatgc agcaatagca   3951

acaatcacga ctgggctatt gatgtggaca tttataagtg actactacaa atacaaacag   4011

tggacgcagt tcctgattag tatagtgtct ggtatattcc tcataaggac gctaaaatgg   4071

ataggcggtt tagagttgca cgcacctgaa ttgccatcct acaggcccct attcttcatc   4131

ttgacatacc taatttctgc tgcaatagta actagatgga atttagacat agctggcgtg   4191

cttctgcaat gtgtccccac tatactaatg gtcttaactt tgtgggcaga tctgttaacg   4251

ctaattctga tactacctac ttatgaacta gccaaactat attacctcaa gggggtgaag   4311

aatggaatgg aaaggaactg gctagggagg ataacttaca aaagagtgtc agatgtttat   4371

gagatagatg aatcccagga agccgtatat ctgttcccct ctaaacagaa ggaagggacg   4431

atcacagggg gtttgctacc actaataaag gccatactga tcagctgcat tagtagcaag   4491

tggcagtgct tctacctcct atatctggtg gtggaggtat catactacct ccataagaaa   4551

ataattgaag aagtagccgg ggaaccaat ctaatttcca gactggttgc agccctgttg   4611

gaggtaaact ggagatttga caatgaagag accaaggggt taaaaaaatt ctatctgata   4671

tcaggccaag ttaagaatct aataataaaa cataaggtga ggaatgaagt ggtagcccac   4731

tggttcaatg aggaagaggt ctatgggatg cccaagctag tgagtgtagt gaaagcagca   4791

acacttaacc ggagcaggca ttgtatactt tgcacagtct gtgaaagcag agactggaaa   4851

ggagagacct gtccgaagtg tgggagattt gggccttcac tgtcatgtgg gatgacattg   4911

tcagactttg aagagaggca ctataagaag atatttataa gagaagacca atcagacggg   4971

ccttttagag aagagtacaa aggatacctc caatacaaag ccagaggcca gcttttcttg   5031

aggaacctcc cgatattagc tacaaaagta aaactattgt tggtgggcaa tttgggatct   5091

gaggtagggg acttggaaca tcttggatgg atcctgagag gtccggcggt gtgcaagaag   5151

ataatagacc atgagaggtg ccatgtatca ataatggaca aattaacagc tttctttggg   5211

atcatgccaa gagggacgac accaagggcg ccgattagat ttccgacatc tctgctaaga   5271

atcaggagag gcctcgagac tggatgggcg tacacacacc aaggaggaat aagttcagtg   5331

gaccatgtga ctgccggaaa ggacttacta gtatgtgact ccatgggtag aacaagagtc   5391

gtatgccaaa gtaataatag gatgacagat gagactgaat atggagtgaa aacggactca   5451

ggttgcccag agggtgctag gtgctacgtg ttcaaccccg aggcagtgaa catatcgggg   5511

accaaaggag ccatggtaca tctacagaaa acaggtggtg aatttacttg cgtgaccgca   5571

tcaggcactc cagctttctt tgacctgaaa aatctgaagg gctggtcagg gctcccaata   5631

tttgaagcat ctagtgggag agtcgtcggt agagttaaag tagggaagaa tgaggagtca   5691

aagcctacaa aactgatgag tggaatacag acggtatcca agagtacaac tgacttaact   5751

gacatggtga aaaagataac aacaatgaat agaggggagt ttaagcagat cacactggcc   5811

acgggtgcag gaaagactac agaattacct agggcggtga tagaagaaat aggccggcac   5871
```

-continued

```
aaaagagtgt tggtcttgat accactcagg gcagcagcag agtcagtata tcaatacatg   5931
aggcagaaac accctagcat agctttcaat ctaaggatcg gggaaatgaa agagggggat   5991
atggccacag ggataacata tgcctcatat ggctattttt gtcagatgcc tcaacccaaa   6051
ctgagagctg ctatggttga atacagttac attttcctag atgaatacca ctgtgcaacg   6111
cctgaacaat tggccataat aggaaaaatt cacaggtttt cagaacagtt gcgagtcgtg   6171
gcaatgacgg caacgcccgc tgggacggtg accactacag ggcagaagca cccgatagag   6231
gaatttatag ctccagaagt gatgaagggt gaagatcttg gctctgagtt cctggagatt   6291
gcaggcctga aaatacccac tgaggaaatg aaaggtaaca tgctggtatt cgtgcccacc   6351
aggaatatgg cagtggagac agcaaagaaa ctgaaagcca aagggtataa ttctggttac   6411
tactacagtg gagaggaccc ggctaacttg agagtagtta catcacagtc gccctatgta   6471
gtagtggcaa ccaatgcaat agagtctgga gtcacattgc cagacctaga tgtagttgta   6531
gacaccgggc tgaaatgtga gaaaaggata cgactgtctt ctaaaatgcc cttcatagtc   6591
accgggttga aaaggatggc agtgactatt ggggaacagg cacagagaag ggggccgggta   6651
ggcagggtca agcccgggag atactatagg agccaagaga cagcagttgg ctccaaagac   6711
taccactatg atctcttaca agcacagaga tatggtatag aggacgggat aaacataaca   6771
aaatccttca gagagatgaa ttatgattgg agtctatacg aagaagatag cctgatgatc   6831
acgcaactag aaatcctaaa taacctattg atatctgaag aactaccagt tgctgtgaag   6891
aacattatgg ccagaacaga ccaccctgaa ccaattcaac tggcatacaa cagctatgaa   6951
gtccaagtac cagtgctgtt ccctaagatc aggaatggag aagtaacaga cagctatgac   7011
agctattcgt tcttgaatgc caggaaactg ggcgacgatg tgccagcata cgtctacgcc   7071
acggaagatg aagacttggc agtggagcta cttggtatgg actggcccga cccgggaaac   7131
caaggtacag ttgaaactgg aagagcatta aaacaagtaa cgggactttc cgctgctgag   7191
aacgccttgc tggtggcttt gtttggatat gtggggtacc aagccttatc aaaaagacat   7251
gtgcctatgg tcacggatat atactcaata gaagaccata ggttggaaga cacgacccat   7311
ctgcagtttg cacccaacgc aattagaacg gatggtaaag aaactgagct aaaagaactg   7371
gcacaaggag acatccagag gtgtgcagag gcaatggttg ggtacgcaca gcaaggggtg   7431
caattcatca aaacccaagc cctgaaggtg caagagaatc atgtattcaa agactcagca   7491
gacaccatag tggaatacgt agacaagttc atgaaagcaa ttgcagaaag taaagatgac   7551
atcctgaggt atggcctgtg gggggctcac acagctcttt ataaaagcat aggggctagg   7611
ctaggttatg aaacagcttt tgcaacactg gtgattaaat ggcttgcttt tgggggtgag   7671
tctataaacg accacgtgaa acaggctgca accgacttag ttgtatatta cataatcaac   7731
agaccccaat tcccgggaga cactgagaca caacaggagg gccggaaatt cgtggctagc   7791
ttactagtct cagccttggc tacatacacc tacaaaagct ggaactatag caatttatca   7851
aaagtggtag agcctgcact tgcttgtctg ccctacgctt cccaggcact caaattgttt   7911
gctccaacgc gcctggagag tgtagtcatc ctcagcacag ccatttacaa gacttacctg   7971
gcaatcaggc gtggtaggag tgatggtcta ctgggtacgg gagttagtgc tgccatggag   8031
atcatgtccc aaaaccctgt atctgttggg atagccgtga tgctgggtgt aggggccgta   8091
gcggcgcata atgccataga gtcaagtgag cagaagagaa cacttttgat gaaggtattt   8151
gtgaagaact tcttagatca agcagcaact gatgaactgg tcaaagagag cccagagaag   8211
atcataacgg ctttgtttga ggccgtgcaa acagtgggca accctcttag gttgatatat   8271
```

-continued

```
cacttatatg gggtattcta taaaggctgg gaagctaaag aagtagcaga gaaaacagct   8331
gggcggaact tgttcacctt aatcatgttt gaagccgtcg agttgcttgg cgtggacagc   8391
gagggaaaga tgaggaggct gtcgggtaat tacctgatag agctcctgca gaaactccat   8451
gacggcttca ggataagcat caaaaagttc gccttaggat gggcaccggg cccattcagc   8511
tgtaactgga ccccagcgga caataggatc aggctccccc acgagaacta ccttagagtc   8571
gtcaccaggt gcagatgtgg gtaccggacg aaggcagtaa aaaactgtgc aggtgagtta   8631
atactggagg aggaagaggg ctcattcttc tgcagaaaca aatttgggag gggagcaccc   8691
aactacaaag tcacaaaatt ttatgatggc aaccttgaag agatcagggc ccgtctaaag   8751
ctggagggcc aggttgagat gtattacaaa ggagccacca ttaagattga ttacagcaac   8811
aataaactta tcctagccac tgataaatgg gaagttgagc actcatacat caccagactc   8871
acgaaaagat acacaggggc tgggtacaaa ggtgccttcc taggggatga acccaaccac   8931
aaaagcctga tcgagaggac ctgcgcaacc gtgtgcaagg ataagatata cttttcaaag   8991
atgaagaaag gctgtgcctt cacgtatgat ctatctctaa gcaacttggt aagattggtc   9051
gacttggttc acaggaacaa gcttgaagag aaagatatcc cggaacgaac tgtaacaacg   9111
tggctggcgt atacattcgt caatgaagac gtgggtacca tcaagccagt cctgggggag   9171
aaggtcatac cggaagagag tgatgagata aatttgcaac caacagtaac agtgaatatg   9231
tctaagtgtc aggtaacagt ggtaggcgag gccaaaaata tgaccaccgg ggtggttcca   9291
ctcacagtga ccaaagaggc atgtaatggt caagaccggt cagttctaaa cattggaatg   9351
gaagaagggg aatacccggg ccctgctgta agcactgtca ctgtgggtga agctgttcaa   9411
agtaaagatg tgcgcccata tgtattggtg ataggttcca ataaggcaac atcaaacagg   9471
gcaaagacag ctaagaacgt taagttgtat aaaggaggag atgctgtcga agtcagagac   9531
ctaattaaga aaggggagat gctggtcgta gctttggccg atgtagaaca ggacttacta   9591
gaatatgtag attacaaagg cactttccta acaagagaga ccctggaagc acttagtctg   9651
ggtaagccaa aagccaaaaa tataaccaaa gctgatgctc acaggctact caacccagaa   9711
aaagagcaga ttggattacc tgactggttc acagctacgg aacctatatt cctggaagct   9771
atgataaaac aagaaaaata ccacataaca ggggatgtag caaccgtgaa agacaaagcc   9831
aaacaattag ggccaccgaa ttccacgaga atagttaagg aggtaggtgc cagggtgtac   9891
accatgaagc ttaatagctg ggctttgcaa gctgaaagag gggatgcaaa cctcaaaccc   9951
ttatttgaag aacttctgct acagtgccca cccgggagaa cagtcaaagg cggaaccatg  10011
gtgtcggcat accagcttgc acaggggaac tggacgccaa ctagctgtaa agtatacatg  10071
gggactataa cagcaaaaag agtaaaaata cacccatatg aagcatatat aaaattgaag  10131
gagcttatag aagagtacaa catgaaaagg gtgactggag atacaggtct aaagagacat  10191
aatgaatgga tcttaaagag aatcaaacac cacgggaacc tgaggactaa gaaaatactg  10251
aacccaggta aagtagcaga acaactcagc agagaaggtc ataaacacaa tgtgtacaac  10311
aagataatag gttcaactat ggcatcagtg ggaatcaagc tggagaagct accagtagtg  10371
agggctcaaa cggacacaac ctttttccat caagccatta gggataaaat agacaaagaa  10431
gagaacccgc agacaccaga cctgcataag gaattgaaag aagttttcaa tgccctaaaa  10491
ataccagaac tcgctgctac ttatgatgca gttgaatggg aggaactgga gacaggtatc  10551
aacaggaaag gagcagctgg ttttttgaa aggaaaaaca ttggtgaaat actggataca  10611
```

-continued

```
gagaaaaaca aggtagagga cataattaga gatttaaaat ctggaagacc tatcaagtat  10671
tacgaaactg caatcccgaa aaatgagaag agagatgtca atgatgattg ggagagcggc  10731
gattttgtag atgaaaagaa accgagagtg atacagtacc cagaggccaa agtcaggcta  10791
gctataacga aggtcatgta caagtgggtc aaacaaaaac cagtggtcat tcccgggtat  10851
gaaggtaaga caccattgtt tgagatattt gataaggtaa aaaaagaatg ggtagcttc  10911
gataatccag ttgcagtgag ctttgacact aaggcttggg acacacaagt taccagcaaa  10971
agcctagagc tgattaggga catacagaaa tactatttca agaaggagtg gcataaattc  11031
attgagacta taactgagca catggtagaa gtgccggtag tcacagctga tggggaggtg  11091
tacatcagcg agggccaaag aggtagtggt caaccggaca ctagtgctgg caatagtatg  11151
ttaaatgtct taaccatggt ttatgctttc tgccgagcca caggcgtgcc ctacaaaagt  11211
ttcaaaaggg ttgccaagat acatgtctgt ggagatgatg gctttttgat aacggagaaa  11271
agcctaggag agaaatttgc cagtaagggt atacaaatcc tacatgaagc aggaaaaccc  11331
cagaaaatta cagaggggga ccgcatgaaa gtagcttata agtttgagga catagaattt  11391
tgctctcaca cccctgtgcc tgtgaggtgg tcagacaaca ccactagcta tatgccaggt  11451
aggaacaccg cgactatcct ggctaagatg gccacaaggc tagattcaag tggagaaagg  11511
gggacaacag catatgagaa ggcagtggct tttagttttc tcctgatgta ctcatggaac  11571
cctctggtta gaaggatttg cctacttacg ctatcgagcg agttgggcac caaacctagt  11631
aaacggacca cctattacta cgaaggcgat ccaatatctg cctataggga ggtgattggc  11691
cacaacttac tagacctgaa gaggacaggc ttggagaaac tggcactatt aaacctgagt  11751
atgtctactc taggtatatg gacaaaacac atcagtaaaa ggttgctaca agactgcgtt  11811
gatgtaggca gcaaggatgg caattggctg gtaaacgcag ataggccgga gagcagaaaa  11871
acaggaaagg tctacttgca aagtggaggc cataccgtaa gagggaggca ttatgaagac  11931
ctgatattgc ctaggatggt gaaaccaaca tttcaaggag tagacagata caaattggga  11991
cccatagtca acgtaatatt cagaaggctg agggttatga tgatggccct ggttggtaga  12051
gggatgtgaa ccatagctga gcatttcatg acaacacgcc aagggccact aaattgtata  12111
tataactgtg taaatattta cctatttatt tactgttatt tatttaatag agacagtgat  12171
atttatttaa tagcttatct atttatttat ttgatgggat gtagatggca actaactacc  12231
tcataggacc acactacact catttttaaa actacagcac tttagctgga agggaaaagc  12291
ctgaagtcca gagttggatt aaggaaaaac cctaacagcc cc                    12333
```

```
<210> SEQ ID NO 14
<211> LENGTH: 100
<212> TYPE: PRT
<213> ORGANISM: Border disease virus

<400> SEQUENCE: 14

Ser Asp Asp Asn Lys Ser Glu Lys Thr Asn Glu Lys Lys Pro Asp Arg
1               5                   10                  15

Val Arg Arg Gly Ala Met Lys Ile Thr Pro Lys Glu Ser Glu Lys Asp
            20                  25                  30

Ser Arg Ser Lys Pro Pro Asp Ala Thr Ile Val Val Glu Gly Ile Lys
        35                  40                  45

Tyr Gln Val Lys Lys Lys Gly Lys Val Lys Gly Lys Asn Thr Gln Asp
    50                  55                  60

Gly Leu Tyr His Asn Lys Asn Lys Pro Pro Glu Ser Arg Lys Lys Leu
```

-continued

```
65                  70                  75                  80

Glu Lys Ala Leu Leu Ala Trp Ala Ile Ile Ala Ile Phe Met Trp Glu
                85                  90                  95

Pro Val Ala Pro
            100


<210> SEQ ID NO 15
<211> LENGTH: 227
<212> TYPE: PRT
<213> ORGANISM: Border disease virus

<400> SEQUENCE: 15

Glu Asn Val Thr Gln Trp Asn Leu Ser Asp Asn Gly Thr Thr Gly Ile
1               5                   10                  15

Gln Leu Leu Met Phe Gln Arg Gly Val Asn Arg Ser Leu His Gly Ile
            20                  25                  30

Trp Pro Glu Lys Ile Cys Thr Gly Val Pro Thr His Leu Ala Thr Asp
        35                  40                  45

Ala Glu Leu Lys Gly Ile Gln Gly Met Met Asp Ala Ser Glu Lys Thr
    50                  55                  60

Asn Tyr Thr Cys Cys Arg Leu Gln Arg His Glu Trp Asn Lys Tyr Gly
65                  70                  75                  80

Trp Cys Asn Trp Tyr Asn Ile Asn Pro Trp Ile Trp Leu Met Asn Lys
                85                  90                  95

Thr Gln Ala Asn Leu Thr Glu Gly Pro Pro Glu Lys Glu Cys Ala Val
            100                 105                 110

Thr Cys Arg Phe Asp Lys Glu Ala Asp Ile Asn Ile Val Thr Gln Ala
        115                 120                 125

Arg Asp Arg Pro Thr Thr Leu Thr Gly Cys Lys Lys Gly Lys Lys Phe
    130                 135                 140

Ser Phe Ala Gly Met Ile Ile Glu Gly Pro Cys Asn Phe Asn Val Ser
145                 150                 155                 160

Val Glu Asp Ile Leu Phe Gly Asp Asn Glu Cys Ser Ser Leu Phe Gln
                165                 170                 175

Asp Thr Ala Leu Tyr Val Val Asp Gly Val Thr Asn Thr Val Glu Asn
            180                 185                 190

Ala Arg Gln Gly Ala Ala Lys Leu Thr Ser Trp Leu Gly Lys Gln Leu
        195                 200                 205

Gly Ile Met Gly Lys Lys Leu Glu His Lys Ser Lys Thr Trp Phe Gly
    210                 215                 220

Ala Asn Ala
225


<210> SEQ ID NO 16
<211> LENGTH: 195
<212> TYPE: PRT
<213> ORGANISM: Border disease virus

<400> SEQUENCE: 16

Gln Ser Pro Tyr Cys Asn Val Thr Arg Lys Ile Gly Tyr Val Trp Tyr
1               5                   10                  15

Thr Asn Asn Cys Thr Pro Ala Cys Leu Pro Lys Asn Thr Lys Ile Ile
            20                  25                  30

Gly Pro Gly Lys Phe Asp Thr Asn Ala Glu Asp Gly Lys Ile Leu His
        35                  40                  45

Glu Met Arg Gly His Ile Ser Glu Phe Ile Leu Leu Ser Leu Val Val
```

-continued

```
    50                  55                  60

Leu Ser Asp Phe Ala Pro Glu Thr Ala Ser Thr Leu Tyr Leu Val Leu
65                  70                  75                  80

His Phe Ala Leu Pro Gln Thr His Glu Val Pro Ser Val Cys Asp Thr
                85                  90                  95

Asn Gln Leu Asn Leu Thr Val Ser Leu Arg Val Asp Asp Val Ile Pro
            100                 105                 110

Ser Ser Val Trp Asn Leu Gly Lys Tyr Val Cys Val Arg Pro Asp Trp
        115                 120                 125

Trp Pro Tyr Glu Thr Thr Met Val Leu Leu Phe Glu Glu Ala Gly Gln
    130                 135                 140

Val Val Lys Leu Val Leu Arg Ala Ile Arg Asp Leu Thr Arg Val Trp
145                 150                 155                 160

Asn Ser Ala Ser Thr Thr Ala Phe Leu Ile Cys Leu Val Lys Val Leu
                165                 170                 175

Arg Gly Gln Val Val Gln Gly Leu Val Trp Leu Leu Leu Val Thr Gly
            180                 185                 190

Ala Gln Gly
        195


<210> SEQ ID NO 17
<211> LENGTH: 373
<212> TYPE: PRT
<213> ORGANISM: Border disease virus

<400> SEQUENCE: 17

Gln Phe Ala Cys Arg Glu Asp Tyr Arg Tyr Ala Leu Ala Arg Thr Lys
1               5                   10                  15

Glu Ile Gly Ala Leu Gly Ala Glu Ser Leu Thr Thr Thr Trp Thr Asp
            20                  25                  30

Tyr Arg Gly Asn Leu Glu Leu Asp Asp Gly Thr Val Arg Ala Thr Cys
        35                  40                  45

Ser Arg Gly Phe Phe Arg Phe Arg Gly His Cys Met Ile Gly Pro Arg
    50                  55                  60

Tyr Leu Ala Ser Leu His Leu Arg Ala Leu Pro Thr Ser Val Thr Phe
65                  70                  75                  80

Glu Leu Ile Pro Gly Gly Ser Ala Met Thr Glu Glu Glu Met Gly Asp
                85                  90                  95

Asp Phe Glu Phe Gly Leu Cys Pro Cys Asp Ser Arg Pro Val Val Lys
            100                 105                 110

Gly Lys Tyr Asn Thr Thr Leu Leu Asn Gly Ser Ala Phe Gln Leu Ile
        115                 120                 125

Cys Pro Tyr Gly Trp Val Gly Arg Val Glu Cys Thr Thr Val Ser Lys
    130                 135                 140

Ser Thr Leu Ala Thr Glu Val Val Lys Ile Tyr Lys Lys Thr Lys Pro
145                 150                 155                 160

Phe Pro Gln Arg Val Gly Cys Asp His Thr Thr Val Tyr Lys Gln Asp
                165                 170                 175

Leu Tyr His Cys Gln Met Gly Gly Asn Trp Thr Cys Met Arg Gly Glu
            180                 185                 190

Val Val Lys Tyr Val Gly Gly Pro Val Lys Lys Cys Glu Trp Cys Gly
        195                 200                 205

Tyr Val Phe Lys Lys Arg Glu Gly Leu Pro His Tyr Pro Ile Gly Arg
    210                 215                 220
```

-continued

```
Cys Met Leu Arg Asn Glu Thr Gly Tyr Arg Ser Val Asp Asp Thr Pro
225                 230                 235                 240

Cys Asp Arg Gly Gly Val Val Ile Ser Lys Thr Gly Glu Leu Glu Cys
            245                 250                 255

Leu Ile Gly Lys Thr Thr Val Lys Val Phe Ser Ser Asp Lys Lys Leu
            260                 265                 270

Gly Pro Met Pro Cys Arg Pro Lys Glu Val Ile Ser Ser Glu Gly Pro
        275                 280                 285

Val Ser Lys Ile Ala Cys Thr Phe Asn Tyr Ser Lys Thr Leu Glu Asn
    290                 295                 300

Lys Tyr Tyr Glu Pro Arg Asp Ser Tyr Phe Gln Gln Tyr Met Leu Lys
305                 310                 315                 320

Gly Gln Tyr Gln Tyr Trp Phe Asp Leu Glu Ala Thr Asp His His Ser
                325                 330                 335

Asp Tyr Phe Ala Glu Phe Ile Met Leu Ala Val Val Ala Leu Leu Gly
            340                 345                 350

Gly Arg Tyr Val Leu Trp Leu Met Val Val Tyr Met Ile Leu Ala Asp
        355                 360                 365

Gln Met Thr Ser Ala
    370


<210> SEQ ID NO 18
<211> LENGTH: 70
<212> TYPE: PRT
<213> ORGANISM: Border disease virus

<400> SEQUENCE: 18

Ile Asn Leu Gly Gln Gly Glu Val Val Leu Ile Gly Asn Leu Ile Thr
1               5                   10                  15

His Glu Asp His Glu Val Val Val Tyr Phe Leu Leu Leu Tyr Leu Ile
            20                  25                  30

Val Lys Asp Glu Pro Val Lys Lys Trp Ile Leu Phe Leu Phe His Ala
        35                  40                  45

Met Thr Asn Asn Pro Val Lys Thr Ile Ser Val Gly Leu Leu Met Leu
    50                  55                  60

Ser Gly Leu Val Lys Gly
65                  70


<210> SEQ ID NO 19
<211> LENGTH: 2694
<212> TYPE: DNA
<213> ORGANISM: Bovine viral diarrhea virus : deltaCErnsE1E2p7

<400> SEQUENCE: 19

aaaaacaaac ctcaggaatc acgcaagaaa ctggaaaaag cattgttggc gtgggcaata     60

atagctatag ttttgtttca agttacaatg ggagaaaaca taacacagtg gaacctacaa    120

gataatggga cggaagggat acaacgggca atgttccaaa ggggtgtgaa tagaagttta    180

catggaatct ggccagagaa aatctgtact ggcgtccctt cccatctagc caccgatata    240

gaactaaaaa caattcatgg tatgatggat gcaagtgaga agaccaacta cacgtgttgc    300

agacttcaac gccatgagtg gaacaagcat ggttggtgca actggtacaa tattgaaccc    360

tggattctag tcatgaatag aacccaagcc aatctcactg agggacaacc accaagggag    420

tgcgcagtca cttgtaggta tgatagggct agtgacttaa acgtggtaac acaagctaga    480

gatagcccca cacccttaac aggttgcaag aaaggaaaga acttctcctt tgcaggcata    540
```

-continued

```
ttgatgcggg gcccctgcaa ctttgaaata gctgcaagtg atgtattatt caaagaacat    600

gaacgcatta gtatgttcca ggataccact ctttaccttg ttgacgggtt gaccaactcc    660

ttagaaggtg ccagacaagg aaccgctaaa ctgacaacct ggttaggcaa gcagctcggg    720

atactaggaa aaaagttgga aaacaagagt aagacgtggt ttggagcata cgctgcttcc    780

ccttactgtg atgtcgatcg caaaattggc tacatatggt atacaaaaaa ttgcacccct    840

gcctgcttac ccaagaacac aaaaattgtc ggccctggga aatttggcac caatgcagag    900

gacggcaaga tattacatga gatgggggt cacttgtcgg aggtactact actttcttta    960

gtggtgctgt ccgacttcgc accggaaaca gctagtgtaa tgtacctaat cctacatttt   1020

tccatcccac aaagtcacgt tgatgtaatg gattgtgata agacccagtt gaacctcaca   1080

gtggagctga caacagctga agtaatacca gggtcggtct ggaatctagg caaatatgta   1140

tgtataagac caaattggtg gccttatgag acaactgtag tgttggcatt tgaagaggtg   1200

agccaggtgg tgaagttagt gttgagggca ctcagagatt taacacgcat ttggaacgct   1260

gcaacaacta ctgctttttt agtatgcctt gttaagatag tcaggggcca gatggtacag   1320

ggcattctgt ggctactatt gataacaggg gtacaagggc acttggattg caaacctgaa   1380

ttctcgtatg ccatagcaaa ggacgaaaga attggtcaac tgggggctga aggccttacc   1440

accacttgga aggaatactc acctggaatg aagctggaag acacaatggt cattgcttgg   1500

tgcgaagatg ggaagttaat gtacctccaa agatgcacga gagaaaccag atatctcgca   1560

atcttgcata caagagcctt gccgaccagt gtggtattca aaaaactctt tgatgggcga   1620

aagcaagagg atgtagtcga aatgaacgac aactttgaat ttggactctg cccatgtgat   1680

gccaaaccca tagtaagagg gaagttcaat acaacgctgc tgaacggacc ggccttccag   1740

atggtatgcc ccataggatg gacagggact gtaagctgta cgtcattcaa tatggacacc   1800

ttagccacaa ctgtggtacg gacatataga aggtctaaac cattccctca taggcaaggc   1860

tgtatcaccc aaaagaatct gggggaggat ctccataact gcatccttgg aggaaattgg   1920

acttgtgtgc ctggagacca actactatac aaaggggggct ctattgaatc ttgcaagtgg   1980

tgtggctatc aatttaaaga gagtgaggga ctaccacact accccattgg caagtgtaaa   2040

ttggagaacg agactggtta caggctagta gacagtacct cttgcaatag agaaggtgtg   2100

gccatagtac cacaagggac attaaagtgc aagataggaa aaacaactgt acaggtcata   2160

gctatggata ccaaactcgg acctatgcct tgcagaccat atgaaatcat atcaagtgag   2220

gggcctgtag aaaagacagc gtgtactttc aactacacta agacattaaa aaataagtat   2280

tttgagccca gagacagcta ctttcagcaa tacatgctaa aaggagagta tcaatactgg   2340

tttgacctgg aggtgactga ccatcaccgg gattacttcg ctgagtccat attagtggtg   2400

gtagtagccc tcttgggtgg cagatatgta ctttggttac tggttacata catggtctta   2460

tcagaacaga aggccttagg gattcagtat ggatcagggg aagtggtgat gatgggcaac   2520

ttgctaaccc ataacaatat tgaagtggtg acatacttct tgctgctgta cctactgctg   2580

agggaggaga gcgtaaagaa gtgggtctta ctcttatacc acatcttagt ggtacaccca   2640

atcaaatctg taattgtgat cctactgatg attggggatg tggtaaaggc ctga         2694
```

<210> SEQ ID NO 20
<211> LENGTH: 900
<212> TYPE: PRT
<213> ORGANISM: Bovine viral diarrhea virus : deltaCErnsE1E2p7
<220> FEATURE:
<221> NAME/KEY: MISC_FEATURE -continued

```
<222> LOCATION: (1)..(34)
<223> OTHER INFORMATION: core protein
<220> FEATURE:
<221> NAME/KEY: MISC_FEATURE
<222> LOCATION: (35)..(261)
<223> OTHER INFORMATION: Erns
<220> FEATURE:
<221> NAME/KEY: MISC_FEATURE
<222> LOCATION: (262)..(456)
<223> OTHER INFORMATION: E1
<220> FEATURE:
<221> NAME/KEY: MISC_FEATURE
<222> LOCATION: (457)..(456)
<223> OTHER INFORMATION: E1
<220> FEATURE:
<221> NAME/KEY: MISC_FEATURE
<222> LOCATION: (457)..(830)
<223> OTHER INFORMATION: E2
<220> FEATURE:
<221> NAME/KEY: MISC_FEATURE
<222> LOCATION: (831)..(900)
<223> OTHER INFORMATION: p7

<400> SEQUENCE: 20

Met Asn Ser Lys Asn Lys Pro Gln Glu Ser Arg Lys Lys Leu Glu Lys
1               5                   10                  15

Ala Leu Leu Ala Trp Ala Ile Ile Ala Ile Val Leu Phe Gln Val Thr
            20                  25                  30

Met Gly Glu Asn Ile Thr Gln Trp Asn Leu Gln Asp Asn Gly Thr Glu
        35                  40                  45

Gly Ile Gln Arg Ala Met Phe Gln Arg Gly Val Asn Arg Ser Leu His
    50                  55                  60

Gly Ile Trp Pro Glu Lys Ile Cys Thr Gly Val Pro Ser His Leu Ala
65                  70                  75                  80

Thr Asp Ile Glu Leu Lys Thr Ile His Gly Met Met Asp Ala Ser Glu
                85                  90                  95

Lys Thr Asn Tyr Thr Cys Cys Arg Leu Gln Arg His Glu Trp Asn Lys
            100                 105                 110

His Gly Trp Cys Asn Trp Tyr Asn Ile Glu Pro Trp Ile Leu Val Met
        115                 120                 125

Asn Arg Thr Gln Ala Asn Leu Thr Glu Gly Gln Pro Pro Arg Glu Cys
    130                 135                 140

Ala Val Thr Cys Arg Tyr Asp Arg Ala Ser Asp Leu Asn Val Val Thr
145                 150                 155                 160

Gln Ala Arg Asp Ser Pro Thr Pro Leu Thr Gly Cys Lys Lys Gly Lys
                165                 170                 175

Asn Phe Ser Phe Ala Gly Ile Leu Met Arg Gly Pro Cys Asn Phe Glu
            180                 185                 190

Ile Ala Ala Ser Asp Val Leu Phe Lys Glu His Glu Arg Ile Ser Met
        195                 200                 205

Phe Gln Asp Thr Thr Leu Tyr Leu Val Asp Gly Leu Thr Asn Ser Leu
    210                 215                 220

Glu Gly Ala Arg Gln Gly Thr Ala Lys Leu Thr Thr Trp Leu Gly Lys
225                 230                 235                 240

Gln Leu Gly Ile Leu Gly Lys Lys Leu Glu Asn Lys Ser Lys Thr Trp
                245                 250                 255

Phe Gly Ala Tyr Ala Ala Ser Pro Tyr Cys Asp Val Asp Arg Lys Ile
            260                 265                 270

Gly Tyr Ile Trp Tyr Thr Lys Asn Cys Thr Pro Ala Cys Leu Pro Lys
        275                 280                 285
```

-continued

```
Asn Thr Lys Ile Val Gly Pro Gly Lys Phe Gly Thr Asn Ala Glu Asp
    290                 295                 300

Gly Lys Ile Leu His Glu Met Gly Gly His Leu Ser Glu Val Leu Leu
305                 310                 315                 320

Leu Ser Leu Val Val Leu Ser Asp Phe Ala Pro Glu Thr Ala Ser Val
                325                 330                 335

Met Tyr Leu Ile Leu His Phe Ser Ile Pro Gln Ser His Val Asp Val
            340                 345                 350

Met Asp Cys Asp Lys Thr Gln Leu Asn Leu Thr Val Glu Leu Thr Thr
        355                 360                 365

Ala Glu Val Ile Pro Gly Ser Val Trp Asn Leu Gly Lys Tyr Val Cys
    370                 375                 380

Ile Arg Pro Asn Trp Trp Pro Tyr Glu Thr Thr Val Val Leu Ala Phe
385                 390                 395                 400

Glu Glu Val Ser Gln Val Val Lys Leu Val Leu Arg Ala Leu Arg Asp
                405                 410                 415

Leu Thr Arg Ile Trp Asn Ala Ala Thr Thr Thr Ala Phe Leu Val Cys
            420                 425                 430

Leu Val Lys Ile Val Arg Gly Gln Met Val Gln Gly Ile Leu Trp Leu
        435                 440                 445

Leu Leu Ile Thr Gly Val Gln Gly His Leu Asp Cys Lys Pro Glu Phe
    450                 455                 460

Ser Tyr Ala Ile Ala Lys Asp Glu Arg Ile Gly Gln Leu Gly Ala Glu
465                 470                 475                 480

Gly Leu Thr Thr Thr Trp Lys Glu Tyr Ser Pro Gly Met Lys Leu Glu
                485                 490                 495

Asp Thr Met Val Ile Ala Trp Cys Glu Asp Gly Lys Leu Met Tyr Leu
            500                 505                 510

Gln Arg Cys Thr Arg Glu Thr Arg Tyr Leu Ala Ile Leu His Thr Arg
        515                 520                 525

Ala Leu Pro Thr Ser Val Val Phe Lys Lys Leu Phe Asp Gly Arg Lys
    530                 535                 540

Gln Glu Asp Val Val Glu Met Asn Asp Asn Phe Glu Phe Gly Leu Cys
545                 550                 555                 560

Pro Cys Asp Ala Lys Pro Ile Val Arg Gly Lys Phe Asn Thr Thr Leu
                565                 570                 575

Leu Asn Gly Pro Ala Phe Gln Met Val Cys Pro Ile Gly Trp Thr Gly
            580                 585                 590

Thr Val Ser Cys Thr Ser Phe Asn Met Asp Thr Leu Ala Thr Thr Val
        595                 600                 605

Val Arg Thr Tyr Arg Arg Ser Lys Pro Phe Pro His Arg Gln Gly Cys
    610                 615                 620

Ile Thr Gln Lys Asn Leu Gly Glu Asp Leu His Asn Cys Ile Leu Gly
625                 630                 635                 640

Gly Asn Trp Thr Cys Val Pro Gly Asp Gln Leu Leu Tyr Lys Gly Gly
                645                 650                 655

Ser Ile Glu Ser Cys Lys Trp Cys Gly Tyr Gln Phe Lys Glu Ser Glu
            660                 665                 670

Gly Leu Pro His Tyr Pro Ile Gly Lys Cys Lys Leu Glu Asn Glu Thr
        675                 680                 685

Gly Tyr Arg Leu Val Asp Ser Thr Ser Cys Asn Arg Glu Gly Val Ala
    690                 695                 700

Ile Val Pro Gln Gly Thr Leu Lys Cys Lys Ile Gly Lys Thr Thr Val
```

-continued

```
705                 710                 715                 720

Gln Val Ile Ala Met Asp Thr Lys Leu Gly Pro Met Pro Cys Arg Pro
                725                 730                 735

Tyr Glu Ile Ile Ser Ser Glu Gly Pro Val Glu Lys Thr Ala Cys Thr
            740                 745                 750

Phe Asn Tyr Thr Lys Thr Leu Lys Asn Lys Tyr Phe Glu Pro Arg Asp
        755                 760                 765

Ser Tyr Phe Gln Gln Tyr Met Leu Lys Gly Glu Tyr Gln Tyr Trp Phe
    770                 775                 780

Asp Leu Glu Val Thr Asp His His Arg Asp Tyr Phe Ala Glu Ser Ile
785                 790                 795                 800

Leu Val Val Val Val Ala Leu Leu Gly Gly Arg Tyr Val Leu Trp Leu
                805                 810                 815

Leu Val Thr Tyr Met Val Leu Ser Glu Gln Lys Ala Leu Gly Ile Gln
            820                 825                 830

Tyr Gly Ser Gly Glu Val Val Met Met Gly Asn Leu Leu Thr His Asn
        835                 840                 845

Asn Ile Glu Val Val Thr Tyr Phe Leu Leu Leu Tyr Leu Leu Leu Arg
    850                 855                 860

Glu Glu Ser Val Lys Lys Trp Val Leu Leu Leu Tyr His Ile Leu Val
865                 870                 875                 880

Val His Pro Ile Lys Ser Val Ile Val Ile Leu Leu Met Ile Gly Asp
                885                 890                 895

Val Val Lys Ala
            900


<210> SEQ ID NO 21
<211> LENGTH: 2484
<212> TYPE: DNA
<213> ORGANISM: Bovine viral diarrhea virus : delraCErnsE1E2

<400> SEQUENCE: 21

aaaaacaaac ctcaggaatc acgcaagaaa ctggaaaaag cattgttggc gtgggcaata     60

atagctatag ttttgtttca agttacaatg ggagaaaaca taacacagtg gaacctacaa    120

gataatggga cggaagggat acaacgggca atgttccaaa ggggtgtgaa tagaagttta    180

catggaatct ggccagagaa aatctgtact ggcgtccctt cccatctagc caccgatata    240

gaactaaaaa caattcatgg tatgatggat gcaagtgaga agaccaacta cacgtgttgc    300

agacttcaac gccatgagtg gaacaagcat ggttggtgca actggtacaa tattgaaccc    360

tggattctag tcatgaatag aacccaagcc aatctcactg agggacaacc accaagggag    420

tgcgcagtca cttgtaggta tgatagggct agtgacttaa acgtggtaac acaagctaga    480

gatagcccca cacccttaac aggttgcaag aaaggaaaga acttctcctt tgcaggcata    540

ttgatgcggg gcccctgcaa ctttgaaata gctgcaagtg atgtattatt caaagaacat    600

gaacgcatta gtatgttcca ggataccact ctttaccttg ttgacgggtt gaccaactcc    660

ttagaaggtg ccagacaagg aaccgctaaa ctgacaacct ggttaggcaa gcagctcggg    720

atactaggaa aaaagttgga aaacaagagt aagacgtggt ttggagcata cgctgcttcc    780

ccttactgtg atgtcgatcg caaaattggc tacatatggt atacaaaaaa ttgcacccct    840

gcctgcttac ccaagaacac aaaaattgtc ggccctggga aatttggcac caatgcagag    900

gacggcaaga tattacatga gatggggggt cacttgtcgg aggtactact actttcttta    960

gtggtgctgt ccgacttcgc accggaaaca gctagtgtaa tgtacctaat cctacatttt   1020
```

-continued

```
tccatcccac aaagtcacgt tgatgtaatg gattgtgata agacccagtt gaacctcaca   1080

gtggagctga caacagctga agtaatacca gggtcggtct ggaatctagg caaatatgta   1140

tgtataagac caaattggtg gccttatgag acaactgtag tgttggcatt tgaagaggtg   1200

agccaggtgg tgaagttagt gttgagggca ctcagagatt taacacgcat ttggaacgct   1260

gcaacaacta ctgctttttt agtatgcctt gttaagatag tcaggggcca gatggtacag   1320

ggcattctgt ggctactatt gataacaggg gtacaagggc acttggattg caaacctgaa   1380

ttctcgtatg ccatagcaaa ggacgaaaga attggtcaac tgggggctga aggccttacc   1440

accacttgga aggaatactc acctggaatg aagctggaag acacaatggt cattgcttgg   1500

tgcgaagatg ggaagttaat gtacctccaa agatgcacga gagaaaccag atatctcgca   1560

atcttgcata caagagcctt gccgaccagt gtggtattca aaaaactctt tgatgggcga   1620

aagcaagagg atgtagtcga aatgaacgac aactttgaat ttggactctg cccatgtgat   1680

gccaaaccca tagtaagagg gaagttcaat acaacgctgc tgaacggacc ggccttccag   1740

atggtatgcc ccataggatg gacagggact gtaagctgta cgtcattcaa tatggacacc   1800

ttagccacaa ctgtggtacg gacatataga aggtctaaac cattccctca taggcaaggc   1860

tgtatcaccc aaaagaatct gggggaggat ctccataact gcatccttgg aggaaattgg   1920

acttgtgtgc ctggagacca actactatac aaagggggct ctattgaatc ttgcaagtgg   1980

tgtggctatc aatttaaaga gagtgaggga ctaccacact accccattgg caagtgtaaa   2040

ttggagaacg agactggtta caggctagta gacagtacct cttgcaatag agaaggtgtg   2100

gccatagtac cacaagggac attaaagtgc aagataggaa aaacaactgt acaggtcata   2160

gctatggata ccaaactcgg acctatgcct tgcagaccat atgaaatcat atcaagtgag   2220

gggcctgtag aaaagacagc gtgtactttc aactacacta agacattaaa aaataagtat   2280

tttgagccca gagacagcta ctttcagcaa tacatgctaa aggagagtta tcaatactgg   2340

tttgacctgg aggtgactga ccatcaccgg gattacttcg ctgagtccat attagtggtg   2400

gtagtagccc tcttgggtgg cagatatgta ctttggttac tggttacata catggtctta   2460

tcagaacaga aggccttagg gtga                                           2484
```

```
<210> SEQ ID NO 22
<211> LENGTH: 827
<212> TYPE: PRT
<213> ORGANISM: Bovine viral diarrhea virus : deltaCErnsE1E2

<400> SEQUENCE: 22

Lys Asn Lys Pro Gln Glu Ser Arg Lys Lys Leu Glu Lys Ala Leu Leu
1               5                   10                  15

Ala Trp Ala Ile Ile Ala Ile Val Leu Phe Gln Val Thr Met Gly Glu
            20                  25                  30

Asn Ile Thr Gln Trp Asn Leu Gln Asp Asn Gly Thr Glu Gly Ile Gln
        35                  40                  45

Arg Ala Met Phe Gln Arg Gly Val Asn Arg Ser Leu His Gly Ile Trp
    50                  55                  60

Pro Glu Lys Ile Cys Thr Gly Val Pro Ser His Leu Ala Thr Asp Ile
65                  70                  75                  80

Glu Leu Lys Thr Ile His Gly Met Met Asp Ala Ser Glu Lys Thr Asn
                85                  90                  95

Tyr Thr Cys Cys Arg Leu Gln Arg His Glu Trp Asn Lys His Gly Trp
            100                 105                 110
```

-continued

```
Cys Asn Trp Tyr Asn Ile Glu Pro Trp Ile Leu Val Met Asn Arg Thr
        115                 120                 125

Gln Ala Asn Leu Thr Glu Gly Gln Pro Pro Arg Glu Cys Ala Val Thr
    130                 135                 140

Cys Arg Tyr Asp Arg Ala Ser Asp Leu Asn Val Val Thr Gln Ala Arg
145                 150                 155                 160

Asp Ser Pro Thr Pro Leu Thr Gly Cys Lys Lys Gly Lys Asn Phe Ser
                165                 170                 175

Phe Ala Gly Ile Leu Met Arg Gly Pro Cys Asn Phe Glu Ile Ala Ala
            180                 185                 190

Ser Asp Val Leu Phe Lys Glu His Glu Arg Ile Ser Met Phe Gln Asp
        195                 200                 205

Thr Thr Leu Tyr Leu Val Asp Gly Leu Thr Asn Ser Leu Glu Gly Ala
    210                 215                 220

Arg Gln Gly Thr Ala Lys Leu Thr Thr Trp Leu Gly Lys Gln Leu Gly
225                 230                 235                 240

Ile Leu Gly Lys Lys Leu Glu Asn Lys Ser Lys Thr Trp Phe Gly Ala
                245                 250                 255

Tyr Ala Ala Ser Pro Tyr Cys Asp Val Asp Arg Lys Ile Gly Tyr Ile
            260                 265                 270

Trp Tyr Thr Lys Asn Cys Thr Pro Ala Cys Leu Pro Lys Asn Thr Lys
        275                 280                 285

Ile Val Gly Pro Gly Lys Phe Gly Thr Asn Ala Glu Asp Gly Lys Ile
    290                 295                 300

Leu His Glu Met Gly Gly His Leu Ser Glu Val Leu Leu Leu Ser Leu
305                 310                 315                 320

Val Val Leu Ser Asp Phe Ala Pro Glu Thr Ala Ser Val Met Tyr Leu
                325                 330                 335

Ile Leu His Phe Ser Ile Pro Gln Ser His Val Asp Val Met Asp Cys
            340                 345                 350

Asp Lys Thr Gln Leu Asn Leu Thr Val Glu Leu Thr Thr Ala Glu Val
        355                 360                 365

Ile Pro Gly Ser Val Trp Asn Leu Gly Lys Tyr Val Cys Ile Arg Pro
    370                 375                 380

Asn Trp Trp Pro Tyr Glu Thr Thr Val Val Leu Ala Phe Glu Glu Val
385                 390                 395                 400

Ser Gln Val Val Lys Leu Val Leu Arg Ala Leu Arg Asp Leu Thr Arg
                405                 410                 415

Ile Trp Asn Ala Ala Thr Thr Thr Ala Phe Leu Val Cys Leu Val Lys
            420                 425                 430

Ile Val Arg Gly Gln Met Val Gln Gly Ile Leu Trp Leu Leu Leu Ile
        435                 440                 445

Thr Gly Val Gln Gly His Leu Asp Cys Lys Pro Glu Phe Ser Tyr Ala
    450                 455                 460

Ile Ala Lys Asp Glu Arg Ile Gly Gln Leu Gly Ala Glu Gly Leu Thr
465                 470                 475                 480

Thr Thr Trp Lys Glu Tyr Ser Pro Gly Met Lys Leu Glu Asp Thr Met
                485                 490                 495

Val Ile Ala Trp Cys Glu Asp Gly Lys Leu Met Tyr Leu Gln Arg Cys
            500                 505                 510

Thr Arg Glu Thr Arg Tyr Leu Ala Ile Leu His Thr Arg Ala Leu Pro
        515                 520                 525
```

-continued

```
Thr Ser Val Val Phe Lys Lys Leu Phe Asp Gly Arg Lys Gln Glu Asp
    530                 535                 540

Val Val Glu Met Asn Asp Asn Phe Glu Phe Gly Leu Cys Pro Cys Asp
545                 550                 555                 560

Ala Lys Pro Ile Val Arg Gly Lys Phe Asn Thr Thr Leu Leu Asn Gly
                565                 570                 575

Pro Ala Phe Gln Met Val Cys Pro Ile Gly Trp Thr Gly Thr Val Ser
            580                 585                 590

Cys Thr Ser Phe Asn Met Asp Thr Leu Ala Thr Thr Val Val Arg Thr
        595                 600                 605

Tyr Arg Arg Ser Lys Pro Phe Pro His Arg Gln Gly Cys Ile Thr Gln
    610                 615                 620

Lys Asn Leu Gly Glu Asp Leu His Asn Cys Ile Leu Gly Gly Asn Trp
625                 630                 635                 640

Thr Cys Val Pro Gly Asp Gln Leu Leu Tyr Lys Gly Gly Ser Ile Glu
                645                 650                 655

Ser Cys Lys Trp Cys Gly Tyr Gln Phe Lys Glu Ser Glu Gly Leu Pro
            660                 665                 670

His Tyr Pro Ile Gly Lys Cys Lys Leu Glu Asn Glu Thr Gly Tyr Arg
        675                 680                 685

Leu Val Asp Ser Thr Ser Cys Asn Arg Glu Gly Val Ala Ile Val Pro
    690                 695                 700

Gln Gly Thr Leu Lys Cys Lys Ile Gly Lys Thr Thr Val Gln Val Ile
705                 710                 715                 720

Ala Met Asp Thr Lys Leu Gly Pro Met Pro Cys Arg Pro Tyr Glu Ile
                725                 730                 735

Ile Ser Ser Glu Gly Pro Val Glu Lys Thr Ala Cys Thr Phe Asn Tyr
            740                 745                 750

Thr Lys Thr Leu Lys Asn Lys Tyr Phe Glu Pro Arg Asp Ser Tyr Phe
        755                 760                 765

Gln Gln Tyr Met Leu Lys Gly Glu Tyr Gln Tyr Trp Phe Asp Leu Glu
    770                 775                 780

Val Thr Asp His His Arg Asp Tyr Phe Ala Glu Ser Ile Leu Val Val
785                 790                 795                 800

Val Val Ala Leu Leu Gly Gly Arg Tyr Val Leu Trp Leu Leu Val Thr
                805                 810                 815

Tyr Met Val Leu Ser Glu Gln Lys Ala Leu Gly
            820                 825


<210> SEQ ID NO 23
<211> LENGTH: 2013
<212> TYPE: DNA
<213> ORGANISM: Bovine viral diarrhea virus : deltaCE1E2p7

<400> SEQUENCE: 23

aaaaacaaac ctcaggaatc acgcaagaaa ctggaaaaag cattgttggc gtgggcaata     60

atagctatag ttttgtttca agttacaatg ggagcttccc cttactgtga tgtcgatcgc    120

aaaattggct acatatggta tacaaaaaat tgcacccctg cctgcttacc caagaacaca    180

aaaattgtcg gccctgggaa atttggcacc aatgcagagg acggcaagat attacatgag    240

atgggggggtc acttgtcgga ggtactacta ctttctttag tggtgctgtc cgacttcgca    300

ccggaaacag ctagtgtaat gtacctaatc ctacattttt ccatcccaca aagtcacgtt    360

gatgtaatgg attgtgataa gacccagttg aacctcacag tggagctgac aacagctgaa    420
```

-continued

```
gtaataccag ggtcggtctg gaatctaggc aaatatgtat gtataagacc aaattggtgg    480

ccttatgaga caactgtagt gttggcattt gaagaggtga gccaggtggt gaagttagtg    540

ttgagggcac tcagagattt aacacgcatt tggaacgctg caacaactac tgctttttta    600

gtatgccttg ttaagatagt caggggccag atggtacagg gcattctgtg gctactattg    660

ataacagggg tacaagggca cttggattgc aaacctgaat tctcgtatgc catagcaaag    720

gacgaaagaa ttggtcaact gggggctgaa ggccttacca ccacttggaa ggaatactca    780

cctggaatga agctggaaga cacaatggtc attgcttggt gcgaagatgg gaagttaatg    840

tacctccaaa gatgcacgag agaaaccaga tatctcgcaa tcttgcatac aagagccttg    900

ccgaccagtg tggtattcaa aaaactcttt gatgggcgaa agcaagagga tgtagtcgaa    960

atgaacgaca actttgaatt tggactctgc ccatgtgatg ccaaacccat agtaagaggg   1020

aagttcaata caacgctgct gaacggaccg gccttccaga tggtatgccc cataggatgg   1080

acagggactg taagctgtac gtcattcaat atggacacct tagccacaac tgtggtacgg   1140

acatatagaa ggtctaaacc attccctcat aggcaaggct gtatcaccca aaagaatctg   1200

ggggaggatc tccataactg catccttgga ggaaattgga cttgtgtgcc tggagaccaa   1260

ctactataca aagggggctc tattgaatct tgcaagtggt gtggctatca atttaaagag   1320

agtgagggac taccacacta ccccattggc aagtgtaaat tggagaacga gactggttac   1380

aggctagtag acagtacctc ttgcaataga gaaggtgtgg ccatagtacc acaagggaca   1440

ttaaagtgca agataggaaa aacaactgta caggtcatag ctatggatac caaactcgga   1500

cctatgcctt gcagaccata tgaaatcata tcaagtgagg ggcctgtaga aaagacagcg   1560

tgtactttca actacactaa gacattaaaa aataagtatt ttgagcccag agacagctac   1620

tttcagcaat acatgctaaa aggagagtat caatactggt ttgacctgga ggtgactgac   1680

catcaccggg attacttcgc tgagtccata ttagtggtgg tagtagccct cttgggtggc   1740

agatatgtac tttggttact ggttacatac atggtcttat cagaacagaa ggccttaggg   1800

attcagtatg gatcagggga agtggtgatg atgggcaact tgctaaccca taacaatatt   1860

gaagtggtga catacttctt gctgctgtac ctactgctga gggaggagag cgtaaagaag   1920

tgggtcttac tcttatacca catcttagtg gtacacccaa tcaaatctgt aattgtgatc   1980

ctactgatga ttggggatgt ggtaaaggcc tga                                2013
```

```
<210> SEQ ID NO 24
<211> LENGTH: 670
<212> TYPE: PRT
<213> ORGANISM: Bovine viral diarrhea virus : deltaCE1E2p7

<400> SEQUENCE: 24

Lys Asn Lys Pro Gln Glu Ser Arg Lys Lys Leu Glu Lys Ala Leu Leu
1               5                   10                  15

Ala Trp Ala Ile Ile Ala Ile Val Leu Phe Gln Val Thr Met Gly Ala
            20                  25                  30

Ser Pro Tyr Cys Asp Val Asp Arg Lys Ile Gly Tyr Ile Trp Tyr Thr
        35                  40                  45

Lys Asn Cys Thr Pro Ala Cys Leu Pro Lys Asn Thr Lys Ile Val Gly
    50                  55                  60

Pro Gly Lys Phe Gly Thr Asn Ala Glu Asp Gly Lys Ile Leu His Glu
65                  70                  75                  80

Met Gly Gly His Leu Ser Glu Val Leu Leu Leu Ser Leu Val Val Leu
                85                  90                  95
```

-continued

```
Ser Asp Phe Ala Pro Glu Thr Ala Ser Val Met Tyr Leu Ile Leu His
            100                 105                 110

Phe Ser Ile Pro Gln Ser His Val Asp Val Met Asp Cys Asp Lys Thr
        115                 120                 125

Gln Leu Asn Leu Thr Val Glu Leu Thr Thr Ala Glu Val Ile Pro Gly
    130                 135                 140

Ser Val Trp Asn Leu Gly Lys Tyr Val Cys Ile Arg Pro Asn Trp Trp
145                 150                 155                 160

Pro Tyr Glu Thr Thr Val Val Leu Ala Phe Glu Glu Val Ser Gln Val
                165                 170                 175

Val Lys Leu Val Leu Arg Ala Leu Arg Asp Leu Thr Arg Ile Trp Asn
            180                 185                 190

Ala Ala Thr Thr Thr Ala Phe Leu Val Cys Leu Val Lys Ile Val Arg
        195                 200                 205

Gly Gln Met Val Gln Gly Ile Leu Trp Leu Leu Leu Ile Thr Gly Val
    210                 215                 220

Gln Gly His Leu Asp Cys Lys Pro Glu Phe Ser Tyr Ala Ile Ala Lys
225                 230                 235                 240

Asp Glu Arg Ile Gly Gln Leu Gly Ala Glu Gly Leu Thr Thr Thr Trp
                245                 250                 255

Lys Glu Tyr Ser Pro Gly Met Lys Leu Glu Asp Thr Met Val Ile Ala
            260                 265                 270

Trp Cys Glu Asp Gly Lys Leu Met Tyr Leu Gln Arg Cys Thr Arg Glu
        275                 280                 285

Thr Arg Tyr Leu Ala Ile Leu His Thr Arg Ala Leu Pro Thr Ser Val
    290                 295                 300

Val Phe Lys Lys Leu Phe Asp Gly Arg Lys Gln Glu Asp Val Val Glu
305                 310                 315                 320

Met Asn Asp Asn Phe Glu Phe Gly Leu Cys Pro Cys Asp Ala Lys Pro
                325                 330                 335

Ile Val Arg Gly Lys Phe Asn Thr Thr Leu Leu Asn Gly Pro Ala Phe
            340                 345                 350

Gln Met Val Cys Pro Ile Gly Trp Thr Gly Thr Val Ser Cys Thr Ser
        355                 360                 365

Phe Asn Met Asp Thr Leu Ala Thr Thr Val Val Arg Thr Tyr Arg Arg
    370                 375                 380

Ser Lys Pro Phe Pro His Arg Gln Gly Cys Ile Thr Gln Lys Asn Leu
385                 390                 395                 400

Gly Glu Asp Leu His Asn Cys Ile Leu Gly Gly Asn Trp Thr Cys Val
                405                 410                 415

Pro Gly Asp Gln Leu Leu Tyr Lys Gly Gly Ser Ile Glu Ser Cys Lys
            420                 425                 430

Trp Cys Gly Tyr Gln Phe Lys Glu Ser Glu Gly Leu Pro His Tyr Pro
        435                 440                 445

Ile Gly Lys Cys Lys Leu Glu Asn Glu Thr Gly Tyr Arg Leu Val Asp
    450                 455                 460

Ser Thr Ser Cys Asn Arg Glu Gly Val Ala Ile Val Pro Gln Gly Thr
465                 470                 475                 480

Leu Lys Cys Lys Ile Gly Lys Thr Thr Val Gln Val Ile Ala Met Asp
                485                 490                 495

Thr Lys Leu Gly Pro Met Pro Cys Arg Pro Tyr Glu Ile Ile Ser Ser
            500                 505                 510
```

-continued

Glu Gly Pro Val Glu Lys Thr Ala Cys Thr Phe Asn Tyr Thr Lys Thr
        515                 520                 525

Leu Lys Asn Lys Tyr Phe Glu Pro Arg Asp Ser Tyr Phe Gln Gln Tyr
    530                 535                 540

Met Leu Lys Gly Glu Tyr Gln Tyr Trp Phe Asp Leu Glu Val Thr Asp
545                 550                 555                 560

His His Arg Asp Tyr Phe Ala Glu Ser Ile Leu Val Val Val Val Ala
                565                 570                 575

Leu Leu Gly Gly Arg Tyr Val Leu Trp Leu Leu Val Thr Tyr Met Val
            580                 585                 590

Leu Ser Glu Gln Lys Ala Leu Gly Ile Gln Tyr Gly Ser Gly Glu Val
        595                 600                 605

Val Met Met Gly Asn Leu Leu Thr His Asn Asn Ile Glu Val Val Thr
    610                 615                 620

Tyr Phe Leu Leu Leu Tyr Leu Leu Leu Arg Glu Glu Ser Val Lys Lys
625                 630                 635                 640

Trp Val Leu Leu Leu Tyr His Ile Leu Val Val His Pro Ile Lys Ser
                645                 650                 655

Val Ile Val Ile Leu Leu Met Ile Gly Asp Val Val Lys Ala
            660                 665                 670

<210> SEQ ID NO 25
<211> LENGTH: 1803
<212> TYPE: DNA
<213> ORGANISM: Bovine viral diarrhea virus : deltaCE1E2

<400> SEQUENCE: 25
aaaaacaaac ctcaggaatc acgcaagaaa ctggaaaaag cattgttggc gtgggcaata 60
atagctatag ttttgtttca agttacaatg ggagcttccc cttactgtga tgtcgatcgc 120
aaaattggct acatatggta tacaaaaaat tgcacccctg cctgcttacc caagaacaca 180
aaaattgtcg gccctgggaa atttggcacc aatgcagagg acggcaagat attacatgag 240 atgggggggtc acttgtcgga ggtactacta ctttctttag tggtgctgtc cgacttcgca 300
ccggaaacag ctagtgtaat gtacctaatc ctacattttt ccatcccaca aagtcacgtt 360
gatgtaatgg attgtgataa gacccagttg aacctcacag tggagctgac aacagctgaa 420
gtaataccag ggtcggtctg gaatctaggc aaatatgtat gtataagacc aaattggtgg 480
ccttatgaga caactgtagt gttggcattt gaagaggtga gccaggtggt gaagttagtg 540
ttgagggcac tcagagattt aacacgcatt tggaacgctg caacaactac tgctttttta 600
gtatgccttg ttaagatagt caggggccag atggtacagg gcattctgtg gctactattg 660
ataacagggg tacaagggca cttggattgc aaacctgaat tctcgtatgc catagcaaag 720
gacgaaagaa ttggtcaact gggggctgaa ggccttacca ccacttggaa ggaatactca 780
cctggaatga agctggaaga cacaatggtc attgcttggt gcgaagatgg gaagttaatg 840
tacctccaaa gatgcacgag agaaaccaga tatctcgcaa tcttgcatac aagagccttg 900
ccgaccagtg tggtattcaa aaaactcttt gatgggcgaa agcaagagga tgtagtcgaa 960
atgaacgaca actttgaatt tggactctgc ccatgtgatg ccaaacccat agtaagaggg 1020
aagttcaata caacgctgct gaacggaccg gccttccaga tggtatgccc cataggatgg 1080
acagggactg taagctgtac gtcattcaat atggacacct tagccacaac tgtggtacgg 1140
acatatagaa ggtctaaacc attccctcat aggcaaggct gtatcaccca aaagaatctg 1200
ggggaggatc tccataactg catccttgga ggaaattgga cttgtgtgcc tggagaccaa 1260

-continued

```
ctactataca aagggggctc tattgaatct tgcaagtggt gtggctatca atttaaagag   1320

agtgagggac taccacacta ccccattggc aagtgtaaat tggagaacga gactggttac   1380

aggctagtag acagtacctc ttgcaataga gaaggtgtgg ccatagtacc acaagggaca   1440

ttaaagtgca agataggaaa aacaactgta caggtcatag ctatggatac caaactcgga   1500

cctatgcctt gcagaccata tgaaatcata tcaagtgagg ggcctgtaga aaagacagcg   1560

tgtactttca actacactaa gacattaaaa aataagtatt ttgagcccag agacagctac   1620

tttcagcaat acatgctaaa aggagagtat caatactggt ttgacctgga ggtgactgac   1680

catcaccggg attacttcgc tgagtccata ttagtggtgg tagtagccct cttgggtggc   1740

agatatgtac tttggttact ggttacatac atggtcttat cagaacagaa ggccttaggg   1800

tga                                                                 1803
```

```
<210> SEQ ID NO 26
<211> LENGTH: 600
<212> TYPE: PRT
<213> ORGANISM: Bovine viral diarrhea virus : deltaCE1E2

<400> SEQUENCE: 26

Lys Asn Lys Pro Gln Glu Ser Arg Lys Lys Leu Glu Lys Ala Leu Leu
1               5                   10                  15

Ala Trp Ala Ile Ile Ala Ile Val Leu Phe Gln Val Thr Met Gly Ala
            20                  25                  30

Ser Pro Tyr Cys Asp Val Asp Arg Lys Ile Gly Tyr Ile Trp Tyr Thr
        35                  40                  45

Lys Asn Cys Thr Pro Ala Cys Leu Pro Lys Asn Thr Lys Ile Val Gly
    50                  55                  60

Pro Gly Lys Phe Gly Thr Asn Ala Glu Asp Gly Lys Ile Leu His Glu
65                  70                  75                  80

Met Gly Gly His Leu Ser Glu Val Leu Leu Leu Ser Leu Val Val Leu
                85                  90                  95

Ser Asp Phe Ala Pro Glu Thr Ala Ser Val Met Tyr Leu Ile Leu His
            100                 105                 110

Phe Ser Ile Pro Gln Ser His Val Asp Val Met Asp Cys Asp Lys Thr
        115                 120                 125

Gln Leu Asn Leu Thr Val Glu Leu Thr Thr Ala Glu Val Ile Pro Gly
    130                 135                 140

Ser Val Trp Asn Leu Gly Lys Tyr Val Cys Ile Arg Pro Asn Trp Trp
145                 150                 155                 160

Pro Tyr Glu Thr Thr Val Val Leu Ala Phe Glu Glu Val Ser Gln Val
                165                 170                 175

Val Lys Leu Val Leu Arg Ala Leu Arg Asp Leu Thr Arg Ile Trp Asn
            180                 185                 190

Ala Ala Thr Thr Thr Ala Phe Leu Val Cys Leu Val Lys Ile Val Arg
        195                 200                 205

Gly Gln Met Val Gln Gly Ile Leu Trp Leu Leu Leu Ile Thr Gly Val
    210                 215                 220

Gln Gly His Leu Asp Cys Lys Pro Glu Phe Ser Tyr Ala Ile Ala Lys
225                 230                 235                 240

Asp Glu Arg Ile Gly Gln Leu Gly Ala Glu Gly Leu Thr Thr Thr Trp
                245                 250                 255

Lys Glu Tyr Ser Pro Gly Met Lys Leu Glu Asp Thr Met Val Ile Ala
            260                 265                 270
```

-continued

```
Trp Cys Glu Asp Gly Lys Leu Met Tyr Leu Gln Arg Cys Thr Arg Glu
        275                 280                 285

Thr Arg Tyr Leu Ala Ile Leu His Thr Arg Ala Leu Pro Thr Ser Val
    290                 295                 300

Val Phe Lys Lys Leu Phe Asp Gly Arg Lys Gln Glu Asp Val Val Glu
305                 310                 315                 320

Met Asn Asp Asn Phe Glu Phe Gly Leu Cys Pro Cys Asp Ala Lys Pro
                325                 330                 335

Ile Val Arg Gly Lys Phe Asn Thr Thr Leu Leu Asn Gly Pro Ala Phe
            340                 345                 350

Gln Met Val Cys Pro Ile Gly Trp Thr Gly Thr Val Ser Cys Thr Ser
        355                 360                 365

Phe Asn Met Asp Thr Leu Ala Thr Thr Val Val Arg Thr Tyr Arg Arg
    370                 375                 380

Ser Lys Pro Phe Pro His Arg Gln Gly Cys Ile Thr Gln Lys Asn Leu
385                 390                 395                 400

Gly Glu Asp Leu His Asn Cys Ile Leu Gly Gly Asn Trp Thr Cys Val
                405                 410                 415

Pro Gly Asp Gln Leu Leu Tyr Lys Gly Gly Ser Ile Glu Ser Cys Lys
            420                 425                 430

Trp Cys Gly Tyr Gln Phe Lys Glu Ser Glu Gly Leu Pro His Tyr Pro
        435                 440                 445

Ile Gly Lys Cys Lys Leu Glu Asn Glu Thr Gly Tyr Arg Leu Val Asp
    450                 455                 460

Ser Thr Ser Cys Asn Arg Glu Gly Val Ala Ile Val Pro Gln Gly Thr
465                 470                 475                 480

Leu Lys Cys Lys Ile Gly Lys Thr Thr Val Gln Val Ile Ala Met Asp
                485                 490                 495

Thr Lys Leu Gly Pro Met Pro Cys Arg Pro Tyr Glu Ile Ile Ser Ser
            500                 505                 510

Glu Gly Pro Val Glu Lys Thr Ala Cys Thr Phe Asn Tyr Thr Lys Thr
        515                 520                 525

Leu Lys Asn Lys Tyr Phe Glu Pro Arg Asp Ser Tyr Phe Gln Gln Tyr
    530                 535                 540

Met Leu Lys Gly Glu Tyr Gln Tyr Trp Phe Asp Leu Glu Val Thr Asp
545                 550                 555                 560

His His Arg Asp Tyr Phe Ala Glu Ser Ile Leu Val Val Val Val Ala
                565                 570                 575

Leu Leu Gly Gly Arg Tyr Val Leu Trp Leu Leu Val Thr Tyr Met Val
            580                 585                 590

Leu Ser Glu Gln Lys Ala Leu Gly
        595                 600
```

INFECTIOUS PESTIVIRUS PSEUDO-PARTICLES CONTAINING FUNCTIONAL ERNS, E1, E2 ENVELOPE PROTEINS

The invention relates to the generation and the use of pestivirus pseudo-particles containing native functional E1, E2 envelope glycoproteins assembled onto retroviral core particles. These particles are highly infectious and constitute a valid model of pestivirus virion.

Pestivirus are single-stranded RNA (ssRNA) enveloped spherical viruses that constitute a genus within the family Flaviviridae, which also includes the genera flavivirus and hepacivirus (human hepatitis C viruses). Several pestiviruses are important mammalian pathogens, especially cattle-pathogens, such as the bovine viral diarrhea, the swine fever and the border disease viruses. Pestivirus can cause mucosal diseases (diarrhea), respiratory disease, suppression of an animal's immune system, and severe bleeding disorders.

Pestivirus structural proteins and non structural proteins are expressed from a single polyprotein precursor and individually released in their respective cell compartments upon cleavage by cellular and viral proteases. By analogy with other members of the Flaviviridae, pestivirus genomic organization suggests a virus consisting of a nucleocapsid comprising a viral genome and core protein (C) coated by a lipid envelop containing the two envelope glycoproteins E1 and E2.

The majority of acute bovine viral diarrhea virus (BVDV) infections are caused by noncytopathic viruses. Cattle acutely or persistently infected with BVDV are the primary source of virus. Infected animals shed virus in nasal and oral secretions, feces and urine. The primary virus entrance route is probably oral nasally. Other less important routes of entry may include infected semen, biting insects, and contaminated instruments. Following entry and contact with the mucosal lining of the mouth or nose, initial replication occurs in epithelial cells with a predilection for the palatine tonsils. From here, the virus is able to spread systemically through the blood stream. Spread can occur through both free virus in the serum and virus infected leucocytes, particularly lymphocytes and monocytes. Isolation of virus from serum or leucocytes is generally possible between 3 and 10 days post infection. During systemic spread, the virus is able to gain entry to most tissues with a preference for lymphoid tissues. BVDV broadly infects cattle, sheep, goats, and pigs.

Classical swine fever disease (SVF, previously called hog cholera virus) is another member of the family Flaviviridae, genus Pestivirus. SFV is an economically important contagious disease of swine world-wide. The disease occurs in much of Asia, Central and South America, and parts of Europe and Africa. Several countries have eradication programs in force, based on rapid diagnosis and stamping out of infected herds, supplemented by other control measures. Despite these efforts, SFV has still not been eliminated in many countries. Although SFV can replicate in non-porcine cells, porcine kidney cells are used most frequently for virus growth. Virus replication is restricted to the cytoplasm of the cell and does not result in a cytopathic effect. The first progeny virus is released from the cells at 5–6 hours post-infection. Virion assembly occurs on membranes of the endoplasmic reticulum, but performed capsids and budding are not seen. Instead, fully formed virions appear within the cisternae of the endoplasmic reticulum and are released via exocytosis or cell lysis. Pigs and wild boar are the natural hosts of SFV.

Border disease (BD) is a congenital disease of sheep that was first reported in the bordering countries of England and Wales. A similar, but rare condition also occurs in goats. The causative agent of BD, the border disease virus (BDV), is found worldwide in sheep. Five to fifty percent of sheep tested have antibodies against BD virus; meaning that these ewes have either been exposed to, or are carrying the disease. Transmission of the virus occurs via oral and/or intranasal routes in sheep. Persistently infected sheep are the primary virus reservoir. These ewes will shed virus in all excretions and secretions. Lambs of persistently infected ewes are at risk of becoming persistently infected with the BDV, and thereby perpetuating the disease cycle.

The invention describes the formation and use of infectious pestivirus pseudo-particles harboring unmodified E1 and E2 glycoproteins

Definitions

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence that initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme.

The term "transfection" means the introduction of a foreign nucleic acid (DNA, cDNA or RNA) into a cell so that the host cell will express the introduced gene or sequence to produce a desired substance, typically a protein coded by the introduced gene or sequence. The introduced gene may include regulatory or control sequences, such as start, stop, promoter, signal, secretion, or other sequences used by a cell's genetic machinery. A host cell that receives and expresses introduced DNA or RNA has been "transformed".

The term "host cell" means any cell of any organism that is selected, modified, transformed, grown, or used or manipulated in any way, for the production of a substance by the cell, for example the expression by the cell of a gene, a DNA sequence, a protein, a virion. In the context of the invention, the host cell is a mammalian cell, preferably a cell from cattle, rabbit, pig, goat, swine. Suitable host cells include for instance epithelial cells, leucocytes, lymphocytes, macrophages, monocytes, primary kidney cells from cattle or pig, and BT cells (ATCC CRL-1390).

As used herein, the term "permissive cell" is meant for a cell that is permissive for a pestivirus infection.

"Pestiviruses" are members of the Flaviviridae family. Pestivirus genome encodes a single polyprotein $NH_2$C-Erns-E1-E2-p7-NS2-NS3-NS4a-NS4b-NS5a-NS5b-COOH that is processed co and post-translationally into both structural (N-terminal nucleocapsid protein termed "core" (C), and proteins Erns, E1 and E2) and non-structural (NS) proteins. The amino-terminal part of the polyprotein is cleaved by host cell proteases and its products, core and envelope (Erns, E1 and E2) proteins, are believed to be the major constituents of pestivirus particles (virions). However, the ectodomain Erns-E1 is thought to be processed upon synthesis, thus releasing the non anchored Erns protein.

Although most cleavages in the polyprotein precursor proceed to completion during or immediately after translation, processing between E2 and p7, a hydrophobic domain found at the carboxy terminus of E2, is incomplete and results in the production of fully processed E2 and uncleaved E2-p7.

In the context of the invention, said pestivitus may be of any specie, genotype, subtype, or variant of perstivirus strains. Preferably, the pestivirus according to the invention is selected from the group consisting of bovine viral diarrhea virus (BVDV), Type I or Type II, swine fever virus (SFV) and border disease virus (BDV). The complete genome sequence of BVDV (Genebank: NC_001461), SVF (Genbank: NC_002657) and BDV (Genbank: NC_003679) is shown in SEQ ID No 1, 7 and 13, respectively.

The term "variant" refers to the homologous polynucleotide sequences and corresponding amino acid sequences found in the different pestivirus strains owing to pestivirus hypervariability.

The term "pestivirus-like particles" as used herein refers to non naturally occurring viral particles that comprise an envelope protein of an pestivirus.

The pestivirus pseudo-particles of the invention are infectious for a target cell. The particles of the invention more particularly comprise retroviral core proteins. Such particles may be readily produced by one skilled in genetic engineering techniques. One can for instance refer to EP 1 201 750 that describes production of synthetic retroviral particles expressing an antigen for modulating an immune response.

In the context of the invention, the term "infectious" is used to describe the capacity of the particles of the invention to complete the initial steps of viral cycle that lead to cell entry. However, upon interaction with the host cell, pestivirus-like particles may or may not produce progeny viruses.

The term "an envelope protein of a pestivirus" denotes the native Erns, E1 or E2 glycoprotein: of a pestivirus, or a mutant thereof.

By an "Erns glycoprotein" or "Erns protein" is meant a Erns from any specie, genotype, subtype, or variant of perstivirus strains. The amino acid sequence of BVDV, SFV and BDV Erns protein is shown in SEQ ID No 3, 9, and 15, respectively.

By an "E1 glycoprotein" or "E1 protein" is meant a envelope 1 protein (E1) from any specie, genotype, subtype, or variant of perstivirus strains. The amino acid sequence of BVDV, SFV and BDV E1 protein is shown in SEQ ID No 4, 10, and 16, respectively.

By an "E2 glycoprotein" or "E2 protein" is meant a envelope 2 protein (E2) from any specie, genotype, subtype, or variant of perstivirus strains. The amino acid sequence of BVDV, SFV and BDV E2 protein is shown in SEQ ID No 5, 11, and 17, respectively.

By a "p7 protein" is meant a native pestivirus p7 protein, or a mutant thereof, from any specie, genotype, subtype, or variant of perstivirus strains. The amino acid sequence of BVDV, SFV and BDV p7 protein is shown in SEQ ID No 6, 12, and 18, respectively.

Preferably, Erns, E1, E2, and p7 glycoproteins are derived from a same pestivirus strain. Preferably said Erns and/or E1 and/or E2 and/or p7 proteins are native pestivirus proteins.

The term "mutant" or "mutation" is meant for alteration of the DNA sequence that result in a modification of the amino acid sequence of native Erns, E1. E2, or p7 proteins. Such a modification can be for instance the substitution and/or deletion of one or more amino acids. Mutants notably include fragments of native Erns, E1, E2 and p7 proteins. Variants are particular examples of naturally occurring mutants. Mutants are more particularly contemplated as useful for identifying the structural elements of Erns and/or E1 and/or E2 proteins, and optionally p7 protein, necessary for maintaining cell infectivity or for increasing Erns and/or E1 and/or E2 antigenicity for vaccination purposes. In a preferred embodiment, the mutants encompass E2 glycoproteins wherein hypervariable region I has been deleted, while the particles produced therefrom remain infectious.

The term "pestivirus core" is meant for a native core protein of a pestivirus strains, a fragment thereof, or a variant thereof from any specie, genotype, subtype, or variant of perstivirus strains. According to an embodiment, the core protein is a N-terminally truncated form of pestivirus core (ΔC) that comprises the core signal peptide. The amino acid sequence of BVDV, SFV and BDV core protein is shown in SEQ ID No 2, 8, and 14, respectively.

Upon completion of its addressing function, the core protein is processed by a cellular protease and thereby cleaved from the pestivirus polyprotein. Accordingly, the pestivirus core protein is not found in the pseudo-particles according to the invention.

The term "polyprotein" as used herein is used to describe a protein construct made up of individual proteins that are joined together in a sequence whereby they retain their original relevant biological activities.

The term "a polyprotein comprising a pestivirus core protein linked to pestivirus Erns and/or a pestivirus E1 protein and/or pestivirus E2 protein" , or "a polyprotein comprising successively a pestivirus core protein, and a pestivirus Erns and/or a pestivirus E1 protein and/or pestivirus E2 protein" , includes the CErnsE1E2, CE2ErnsE1, CErnsE1, CE1E2, CE2E1, CE1, CE2, ΔCErnsE1E2, ΔCE2ErnsE1, ΔCErnsE1, ΔCE1 E2, ΔCE2E1, ΔCE1, and ΔCE2 polyproteins.

Optionally, said polyprotein further contain the p7 protein. The polyprotein comprising a pestivirus core protein linked to pestivirus Erns and/or E1 protein and/or pestivirus E2 protein thus additionally includes the CErnsE1E2p7, CE2ErnsE1p7, CE2p7ErnsE1, CErnsE1p7, CE1E2p7, CE2p7E1, CE2E1p7, CE1p7, CE2p7, ΔCErnsE1E2p7, ΔCE2ErnsE1p7, ΔCE2p7ErnsE1, ΔCErnsE1p7, ΔCE1E2p7, ΔCE2E1p7, ΔCE2p7E1, ΔCE1p7, and ΔCE2p7 polyproteins.

"CErnsE1E2" denotes a polyprotein comprising successively a pestivirus core protein, a pestivirus Erns protein, a pestivirus E1 protein and a pestivirus E2 protein. "CE2ErnsE1" denotes a polyprotein comprising successively a pestivirus core protein, a pestivirus E2 protein, a pestivirus Erns protein and a pestivirus E1 protein. "CErnsE1" denotes a polyprotein comprising successively a pestivirus core protein, a pestivirus Erns protein, and a pestivirus E1 protein. "CE1E2" denotes a polyprotein comprising successively a pestivirus core protein, a pestivirus E1 protein and a pestivirus E2 protein. "CE2E1" denotes a polyprotein comprising successively a pestivirus core protein, a pestivirus E2 protein and a pestivirus E1 protein. "CE1E2" denotes a polyprotein comprising successively a pestivirus core protein, a pestivirus E1 protein and a pestivirus E2 protein. "CE1" denotes a polyprotein comprising a pestivirus core protein linked to a pestivirus E1 protein. "CE2" denotes a polyprotein comprising a pestivirus core protein linked to a pestivirus E2 protein.

"ΔCErnsE1E2" denotes a polyprotein comprising successively a carboxy terminus of pestivirus core protein, a pestivirus Erns protein, a pestivirus E1 protein and a pestivirus E2 protein. "ΔCE2ErnsE1" denotes a polyprotein comprising successively a carboxy terminus of pestivirus core protein, a pestivirus E2 protein, a pestivirus Erns protein and a pestivirus E1 protein. "ΔCErnsE1" denotes a polyprotein comprising successively a carboxy terminus of pestivirus core protein, a pestivirus Erns protein, and a pestivirus E1 protein. "ΔCE1E2" denotes a polyprotein comprising successively a carboxy terminus of pestivirus core protein, and pestivirus E1 and pestivirus E2 proteins. "CE1" denotes a polyprotein comprising successively a carboxy terminus of pestivirus core protein, and pestivirus E2 and pestivirus E1 proteins. "CE1" denotes a polyprotein comprising a carboxy terminus of pestivirus core protein linked to a pestivirus E1 protein. "ΔCE2" denotes a polyprotein comprising a carboxy terminus of pestivirus core protein linked to a pestivirus E2 protein. ΔCErnsE1E2, ΔCE1E2, as well as ΔCE2, have been built by inserting a stop codon at the end of E 2, whereas ΔCE2ErnsE1, ΔCErnsE1, ΔCE1 ΔCE2E1 have been built by inserting a stop codon at the end of E1.

"CErnsE1E2p7" denotes a polyprotein comprising successively a pestivirus core protein, a pestivirus Erns protein, a pestivirus E1 protein, a pestivirus E2 protein, and a pestivirus p7 protein. "CE2ErnsE1p7" denotes a polyprotein comprising successively a pestivirus core protein, a pestivirus E2 protein, a pestivirus protein, a pestivirus E1 protein, and a pestivirus p7 protein. "CE2p7ErnsE1" denotes a polyprotein comprising successively a pestivirus core protein, a pestivirus E2 protein, a pestivirus p7 protein, a pestivirus Erns protein, and a pestivirus E1 protein. "CErnsE1p7" denotes a polyprotein comprising successively a pestivirus core protein, a pestivirus Erns protein, a pestivirus E1 protein, and a pestivirus p7 protein. "CE1E2p7" denotes a polyprotein comprising successively a pestivirus core protein, a pestivirus E1 protein, a pestivirus E2 protein, and a pestivirus p7 protein. "CE2p7E1" denotes a polyprotein comprising successively a pestivirus core protein, a pestivirus E2 protein, a pestivirus p7 protein, and a pestivirus E2 protein. "CE2E1p7 denotes a polyprotein comprising successively a pestivirus core protein, a pestivirus E2 protein, a pestivirus E2 protein, and a pestivirus p7 protein. "CE1p7" denotes a polyprotein comprising successively a pestivirus core protein, a pestivirus E1 protein, and a pestivirus p7 protein. "CE2p7" denotes a polyprotein comprising successively a pestivirus core protein, a pestivirus E2 protein, and a pestivirus p7 protein.

"ΔCErnsE1E2p7" denotes a polyprotein comprising successively a carboxy terminus of pestivirus core protein, a pestivirus Erns protein, a pestivirus E1 protein a pestivirus E2 protein, and a pestivirus p7 protein. "CE2ErnsE1p7" denotes a polyprotein comprising successively a carboxy terminus of pestivirus core protein, a pestivirus E2 protein, a pestivirus Erns protein, a pestivirus E1 protein, and a pestivirus p7 protein. ΔCE2p7ErnsE1" denotes a polyprotein comprising successively a carboxy terminus of pestivirus core protein, a pestivirus E2 protein, a pestivirus p7 protein, a pestivirus Erns protein, and a pestivirus E1 protein. "ΔCErnsE1p7" denotes a polyprotein comprising successively a carboxy terminus of pestivirus core protein, a pestivirus Erns protein, a pestivirus E1 protein, and a pestivirus p7 protein. "ΔCE1E2p7" denotes a polyprotein comprising a carboxy terminus of pestivirus core protein, a pestivirus E1 protein, a pestivirus E2 protein, and a pestivirus p7 protein. "ΔCE2E1p7" denotes a polyprotein comprising successively a carboxy terminus of pestivirus core protein, a pestivirus E2 protein, a pestivirus E1 protein, and a pestivirus p7 protein. "ΔCE2p7E1" denotes a polyprotein comprising successively a carboxy terminus of pestivirus core protein, a pestivirus E2 protein, a pestivirus p7 protein, and a pestivirus E1 protein. "ΔCE1p7" denotes a polyprotein comprising successively a carboxy terminus of pestivirus core protein, a pestivirus E1 protein, and a p7 protein. "ΔCE2p7" denotes a polyprotein comprising successively a carboxy terminus of pestivirus core protein, a pestivirus E2 protein, and a p7 protein. ΔCErnsE1E2p7, ΔCE2ErnsE1p7, ΔCErnsE1p7, ΔCE1E2p7, ΔCE2E1p7, ΔCE1p7 as well as ΔCE2p7, have been built by inserting a stop codon at the end of p7 whereas ΔCE2p7ErnsE1, and ΔCE2p7E1 have been built by inserting a stop codon at the end of E1.

By "retrovirus" is meant a virus whose genome consists of a RNA molecule and that comprises a reverse-transcriptase, i.e. a member of the Retroviridae family. Retroviruses are divided into Oncovirus, Lentivirus and Spumavirus. Preferably said retrovirus is an oncovirus, e.g. MLV, ALV, RSV, or MPMV, a lentivirus, e.g. HIV-1, HIV-2, SIV, EIAV, or CAEV, or a spumavirus such as HFV. Genomes of these retroviruses are readily available in databanks.

In the context of the invention "a nucleic sequence comprising a packaging competent retrovirus-derived genome" is intended for a sequence that comprises the retroviral nucleic acid sequences known as "cis-acting" sequences. These include the Long Terminal Repeats (LTRs) for the control of transcription and integration, the psi sequence necessary for encapsidation, and the Primer Binding site (PBS) and polypurine track (PPT) sequences necessary for reverse transcription of the retroviral genome. Advantageously, said nucleic acid sequence comprising a packaging competent retrovirus-derived genome further comprises a transgene.

Said retroviral genome may be replication-defective or replication-competent, in the absence of any trans-complementing function. A replication-competent genome would further comprise the gag, pol, and env retroviral genes. In a replication-defective genome, the viral genes gag, pol, and env are deleted. However, assembly of viral pseudo-particles may be achieved by providing another vector that comprises gag, pol and env but that is defective for the "cis" sequences. Their expression allows the encapsidation of the transgene, excluding the genes necessary for the multiplication of the viral genome and for the formation of complete viral particles.

As used herein, the term "transgene" designates the gene that is expressed in the target cell upon infection by the particles of the invention.

Examples of transgenes include a gene encoding a molecule of therapeutic interest, a marker gene, a gene coding for an immune modulator, an antigen, or a suicide gene.

A "marker gene" denotes a gene whose expression is detectable. For instance marker gene expression can generate a detectable signal, such as a fluorescence emission, a chromogenic reaction, or confer a growth advantage to the cells wherein it is expressed (antibiotic resistance genes).

An "immune modulator" refers to the product of a gene that modifies the activity of the immune system of a subject in vivo. Examples of immune modulators include cytokines, (e.g. interleukins, interferons, or haematopoietic colony stimulating factors), chemokines, and the like. Expression of an immune modulator by transformed cells may change the cellular environment and alter differentiation of immune cells and thus modify the type and the strength of immune response elicited against a given antigen.

An "antigen" refers to a molecule, such as a peptide, a polypeptide or a protein, against which an immune response is sought. Said antigen may be for instance a tumor, a bacterial, a pathogenic, a proteic, or a viral antigen.

A "suicide gene" is meant for a gene whose expression in cells induces programmed-cell death (apoptosis) such as the conditional Herpes Simplex virus type I thymidine kinase gene.

The "core protein from a retrovirus" refers to proteins encoded by the gag and pol genes. The gag gene encodes a polyprotein which is further processed by the retroviral protease into structural proteins that comprise the core. The pol gene encodes the retroviral protease, reverse-transcriptase, and integrase.

A "pharmaceutically acceptable came" refers to any vehicle wherein the vaccine composition according to the invention may be formulated. It includes a saline solution such as phosphate buffer saline. In general, a diluent or carrier is selected on the basis of the mode and route of administration, and standard pharmaceutical practice.

In the context of the present application, "vaccination" is intended for prophylactic or therapeutical vaccination. "Therapeutical vaccination" is meant for vaccination of a patient with a pestivirus infection.

According to the invention, the term "subject" or "patient" is meant for any mammal likely to be infected with pestivirus. Cattle, sheep, pigs and goats are examples of hosts for pestiviruses,

Production of Pestivirus Pseudo-Particles

The inventors have generated infectious pseudo-particles that contain functional, and more particularly unmodified, pestivirus glycoproteins assembled onto retroviral core particles. Pestivirus ErnsE1E2, and optionally p7, are expressed from a polyprotein containing the core (C) protein or a fragment thereof, in particular the carboxy-terminus of the C protein, which served as signal peptide for Erns and/or E1 and/or E2 glycoproteins.

The invention thus provides a method for producing pestivirus-like particles ex vivo comprising the steps of:

providing a first nucleic acid sequence comprising a packaging competent retrovirus-derived genome;

providing a second nucleic acid sequence comprising a cDNA encoding the core proteins from said retrovirus;

providing a third nucleic acid sequence comprising a cDNA encoding a polyprotein comprising successively a pestivirus core protein, and a pestivirus Erns and/or a pestivirus E1 protein and/or a pestivirus E2 protein;

transfecting host cells with said nucleic acid sequences and maintaining the transfected cells in culture for sufficient time to allow expression of the cDNAs to produce structural proteins from pestivirus and retrovirus; and allowing the structural proteins to form virus-like particles.

The invention further provides a method for producing pestivirus-like particles in vivo, which method comprises the steps of:

providing a first nucleic acid sequence comprising a packaging competent retrovirus-derived genome;

providing a second nucleic acid sequence comprising a cDNA encoding the core proteins from said retrovirus;

providing a third nucleic acid sequence comprising a cDNA encoding a polyprotein comprising successively a pestivirus core protein, and a pestivirus Erns and/or a pestivirus E1 protein and/or a pestivirus E2 protein;

transfecting cells of a subject in vivo with said nucleic acid sequences, to allow expression of the cDNAs to produce structural proteins from pestivirus and retrovirus; and to allow the structural proteins to form virus-like particles.

Another aspect of the invention is the use of three nucleic acid sequences for the preparation of a medicament useful as a vaccine against an pestivirus infection wherein the nucleic acid sequences are:

a first nucleic acid sequence comprising a packaging competent retroviral-derived genome;

a second nucleic acid sequence comprising a cDNA encoding core proteins from said retrovirus;

a third nucleic acid sequence comprising a cDNA encoding a polyprotein comprising successively a pestivirus core protein, and a pestivirus Erns and/or a pestivirus E1 protein and/or a pestivirus E2 protein;

and, when transferred into cells of a subject, the nucleic acid sequences allow the production of structural proteins from pestivirus and retrovirus, wherein the structural proteins form virus-like particles that are immunogenic.

For the purpose of transfection, said first, second and third nucleic acid sequences may be carried on a same vector, or on two or three separated vectors.

In particular, plasmoviruses, adenoretroviruses and replicating pseudo-viruses are examples of vectors suitable for carrying the above-mentioned sequences. A plasmovirus vaccine consists in such a plasmid DNA preparation, that allow expression of pestivirus pseudo-particles after administration in an patient in order to elicit a immune response against said pestivirus. Administration of such a plasmovirus vaccine being achieved for preventive vaccination into people at risk for pestivirus-induced disease or for therapeutic vaccination into pestivirus-infected patients. Adenoretroviruses consist in an alternative way to provide the above-mentioned nucleic acid sequences encoding pestivirus pseudo-particles. In this case, it is possible to design three independent adenoretroviruses, i.e. recombinant adenoviruses, that encode the three nucleic acid sequences mentioned above (retroviral core and genome and pestivirus glycoproteins), or, alternatively, it is also possible to design a single adenoretrovirus, derived from "guttless" recombinant adenoviruses, that contains the different nucleic acid sequences. Such adenoretroviruses can be administered to patient as for plasmoviruses, in order to elicit an anti-pestivirus immune response. Replicating pseudo-retroviruses are another alternative possibility to express all the above-mentioned nucleic acid sequences encoding the pestivirus pseudo-particles. Such structures are in fact pestivirus-pseudo-particles whose genome is engineered to allow, following infection, its propagation into cells of an inoculated patient, thereby inducing the production of further replicating pestivirus pseudo-particles. In this case the genome of a retrovirus is modified so as to express the pestivirus E1E2 glycoproteins in place of the retroviral Env gene (encoding the retroviral glycoproteins). The genes encoding the retroviral core proteins are left unchanged. Furthermore an additional gene, encoding a marker gene or an immunomodulator, for example, can be expressed from this genome.

According to a specific embodiment, said packaging competent retroviral genome and core proteins are derived from a retrovirus selected from the group consisting of MLV, ALV, RSV, MPMV, HIV-1, HIV-2, SIV, EIAV. CAEV, and HFV.

Advantageously, the packaging competent retroviral genome further comprises a marker gene or an immune modulator.

In the method of the invention, said polyprotein may comprise CErnsE1E2, CE2ErnsE1, CErnsE1, CE1E2, CE2E1, CE1, CE2, ACErnsE1E2, ACE2ErnsE1, ΔCErnsE1, ΔCE1E2, ΔCE2, ΔCE1, or ΔCE2 polyproteins.

Preferably, said third nucleic acid sequence comprises a cDNA encoding a polyprotein that further comprises a pestivirus p7 protein. Thus, preferably said polyprotein comprises successively a pestivirus core protein, and a pestivirus Erns protein and/or a pestivirus E1 protein and/or a pestivirus E2 protein, and optionally a pestivirus p7 protein. The polyprotein comprising a pestivirus core protein linked to pestivirus Erns and/or E1 protein and/or pestivirus E2 protein thus additionally comprises the CErnsE1E2p7, CE2ErnsE1p7, CE2p7ErnsE1, CErnsE1p7, CE1E2p7, CE2E1p7, CE2p7E1, CE1p7, CE2p7, ΔCErnsE1E2p7, ACE2ErnsE1p7, ΔCE2p7ErnsE1, CErnsE1p7, ΔCE1E2p7, CE2E1p7, CE2p7E1, ΔCE1p7, and ΔCE2p7 polyproteins.

According to an embodiment, Erns and/or E1 and/or E2, and optionally p7 protein, are native proteins. According to another embodiment, Erns and/or E1 and/or E2 proteins, and optionally p7 protein, are mutated to obtain particles that are useful for characterizing the glycoprotein determinants for pestivirus infectivity.

Preferably, said Erns, E1, E2, and optionally p7proteins are derived from a same pestivirus strain.

According to another embodiment said pestivirus core protein is a carboxy terminus form (ΔC) of pestivirus core protein that comprises the core protein signal peptide.

Preferably said pestivirus is selected from the group consisting of bovine viral diarrhea virus (BVDV), swine fever virus (SFV), and Border disease virus (BDV).

In accordance with the present invention there may be employed conventional molecular biology, microbiology, and recombinant DNA techniques within the skill of the art. Such techniques are explained fully in the literature. See, e.g., Sambrook et al., 1989: DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins, eds. (1984)]; Animal Cell Culture [R. I. Freshney, ed. (1986)]; Immobilized Cells and Enzymes [IRL Press, (1986)]; B. Perbal, A Practical Guide To Molecular Cloning (1984); F. M. Ausubel et al., 1994.

In particular, the vectors of the invention may be introduced into the target cell by means of any technique known for the delivery of nucleic acids to the nucleus of cells, either in culture, ex vivo, or in vivo.

Introduction of the nucleic acid sequences may be performed by any standard method well known by one skilled in the art, e.g. transfection, electroporation, microinjection, transduction, cell fusion, DEAE dextran, calcium phosphate precipitation, or use of a gene gun (see for instance Wu et al., 1992; Wu et al, 1988).

The donor nucleic acid targeting system can also be introduced by lipofection. In certain embodiments, the use of liposomes and/or nanoparticles is contemplated for the introduction of the donor nucleic acid targeting system into host cells. Nanocapsules can generally entrap compounds in a stable and reproducible way. Ultrafine particles (sized around 0.1 μm) that can be designed using biodegradable polyalkyl-cyanoacrylate polymers are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The use of cationic lipids may promote encapsulation of negatively charged nucleic acids, and also promote fusion with negatively charged cell membranes (Feigner et al., 1989).

In vivo targeted gene delivery is described in international patent publication WO 95/28 494. Alternatively, the vector can be introduced in vivo by lipofection, using liposomes or nanoparticles as above described. It is also possible to introduce the vector in vivo using techniques that are similar to the techniques that are employed in vitro (e.g. transfection, electroporation . . . ).

Transformed Cells

The invention further relates to a transformed host cell that contains:

a first nucleic acid sequence comprising a packaging competent retrovirus-derived genome;

a second nucleic acid sequence comprising a cDNA encoding the core proteins from said retrovirus; and a third nucleic acid sequence comprising a cDNA encoding a polyprotein comprising successively a pestivirus, core protein, and a pestivirus Erns protein and/or a pestivirus E1 protein and/or a pestivirus E2 protein.

Preferably, said third nucleic acid sequence comprises a cDNA encoding a polyprotein that further comprises a pestivirus p7 protein. Thus, preferably said polyprotein comprises successively a pestivirus core protein, a pestivirus Erns protein and/or a pestivirus E1 protein and/or a pestivirus E2 protein, and optionally a pestivirus p7 protein.

Such a transformed host cell is obtainable as described in a method above.

In another aspect, the invention relates to the use of a transformed host cell as defined above, for the identification of molecules capable of interfering with pestivirus entry in cells. The invention provides in particular a method of ex vivo screening or identification of molecules capable of interfering with pestivirus entry in cells comprising comparison of the level of transformed host cell fusion to a target host cell, in the presence or the absence of a candidate molecule. Said method preferably comprises the steps consisting of:

co-culturing a transformed host cell with a target host cell, in the absence or presence of a candidate molecule, under conditions that allow syncytia formation, i.e. cell—cell fusion, and pestivirus-like particle entry in target host cell in the absence of any candidate molecule;

assessing syncytia formation in the absence and in the presence of said candidate molecule;

comparing syncytia formation measured in presence of said candidate molecule with syncytia formation measured in absence of any candidate molecule;

identifying as a molecule capable of interfering with pestivirus entry the candidate molecule for which syncytia formation, as measured in the presence of said molecule, is decreased as compared to syncytia formation measured in the absence of any candidate molecule.

Contacting a transformed host cell with a target host cell, and a candidate molecule can be carried out by contacting simultaneously said transformed host cell, target host cell and candidate molecule. Otherwise, two of these three elements can be contacted under conditions sufficient to allow their interaction before addition of the third missing element.

Preferably said target host cell is not transformed, i.e. said target host cell does not contains at least one of the first, second, and third nucleic acid sequence as defined above.

Syncytia formation can be readily assessed by one skilled in the art. Briefly, the coculture is submitted to a acidic pH drop by incubation for 5 min at pH-5 and incubated in a normal medium for an additional 12 hrs. Cultures are then stained by adding the May-Grunwald and Giemsa solutions (MERCK) according to the manufacturer recommendations. Cells containing two or more nuclei can be defined as syncytia. A fusion index is then defined as the percentage of (N−S)/T where N is the number of nuclei in the syncytia, S is the number of syncytia and T is the total number of nuclei counted.

Pestivirus-Like Particles

In the method described above no structural modifications of the E1E2 glycoproteins are required for their correct assembly on retroviral cores. The method of the invention thus makes it possible to generate high titre infectious pestivirus pseudo-particles with functional E1E2 proteins As demonstrated herein, these particles constitute a valid model of pestivirus virions as regards to early steps of viral infection cycle.

The invention further relates to an infectious pestivirus-like particle, comprising the core proteins from a retrovirus, and Erns and/or E1 and/or E2 pestivirus glycoprotein(s), and optionally p7 protein. Such a particle is obtainable by a method as described above.

According to an embodiment, the infectious particle of the invention may comprise native pestivirus E1 protein, or native pestivirus E2 protein, or native pestivirus Erns protein and native pestivirus E1 protein, or native pestivirus E1 protein and native pestivirus E2 protein, or native pestivirus Erns protein and native pestivirus E1 protein and native pestivirus E2 protein. Preferably said Erns and E1, or E1 and E2, or Erns, E1 and E2 proteins are derived from a same pestivirus strain. According to another embodiment, Erns and/or E1 and/or E2 glycoproteins are mutated.

Preferably the above described infectious particle of the invention further comprise a native pestivirus p7 protein. Preferably, said E1 and E2 glycoproteins, and p7 protein are derived from a same pestivirus strain. Still preferably said Erns, E1 and E2 glycoproteins, and p7 protein are derived from a same pestivirus strain According to another embodiment, Erns and/or E1 and/or E2 glycoproteins and/or p7 protein are mutated.

Preferably said pestivirus is selected from the group consisting of bovine viral diarrhea virus (BVDV), swine fever virus (SFV), and Border disease virus (BDV).

Said retrovirus may be selected from the group consisting of MLV, ALV, RSV, MPMV, HIV-1 HIV-2, SIV, EIAV, CAEV, and HFV.

Advantageously, said infectious particles further carry a transgene. For instance said transgene may be a marker gene which make it possible to follow-up cell infection by the infectious particles of the invention and can find application for instance in the identification of a cell receptor involved in pestivirus entry. Said transgene can also be a gene encoding a molecule of therapeutic interest and/or a suicide gene.

Use of the Infectious Pestivirus-Like Particles of the Invention

High infectivity of these particles makes it possible for the investigation of the role of pestivirus Erns, E1 and E2 glycoproteins and their potential receptors in cell entry, pestivirus host-range and neutralisation by antibodies from pestivirus patient sera.

The invention therefore concerns the use of a pestivirus-like infectious particle as described above, for ex vivo identification of a cell receptor for pestivirus Erns and/or E1 and/or E2 glycoprotein.

According to an embodiment, the invention provides a method for ex vivo identification of a receptor for pestivirus Erns and/or E1 and/or E2 glycoprotein comprising detection of the binding of said particle to a cell receptor. More specifically, the method may comprise the steps consisting of:

contacting a cell susceptible to pestivirus infection with an infectious pestivirus-like particle of the invention, under conditions sufficient to allow specific binding of said particle to a receptor expressed at the surface of said cell;

detecting binding of said particle to a receptor; and identifying said receptor.

A cell susceptible to a pestivirus infection, may be for instance a kidney primary cell, or cell line, form cattle, pig, or sheep.

Detection of particle binding to a receptor can be achieved according to classical procedures well known by one skilled in the art. For instance, this could involve radioactive, enzyme or fluorescent labelling of the particles of the invention, and subsequent detection with an appropriate method. A number of fluorescent materials are known and can be utilized as labels. These include, for example, fluorescein, rhodamine, auramine, Texas Red. Enzyme labels consist in conjugation of an enzyme to a molecule of interest, e.g. a polypeptide, and can be detected by any of colorimetric, spectrophotometric, or fluorospectrophotometric techniques. Flow cytometry analysis (FACS) together with labelled antibodies directed against E1 or E2 proteins harboured by the pseudo-particles of the invention is also appropriate.

According to another embodiment, the invention provides a method for ex vivo identifying a cell receptor for a pestivirus comprising the step consisting of:

transfecting a cell which is not permissive for pestivirus infection with a nucleic acid sequence encoding a protein likely to be a receptor for pestivirus;

contacting said transformed cell with a pestivirus-like particle of the invention;

determining whether said transformed cell has become permissive or not for pestivirus infection; and identifying as a cell receptor for a pestivirus said protein expressed by the transformed cell that has become permissive.

Determination of whether the transformed cell has become permissive for pestivirus infection can be readily achieved using the pestivirus-like particles of the invention. In particular, where said particles carry a marker gene, such as GFP, permissivity (i.e. the capacity of cells to be infected with a pestivirus, or with a pestivirus-like particle) can be assessed by FACS analysis of the transformed cells. Where the marker gene is an antibiotic resistance gene, identification of cells infected by the pestivirus-like particle is readily achieved through exposure to said antibiotic.

Where one does not suspect a given protein to be a receptor for pestivirus entry, in cells, the above method can advantageously be adapted for the screening and the identification of a cell receptor for a pestivirus. In particular, an expression cDNA library can be prepared, for instance from a cDNA library obtained by reverse transcription of cellular mRNAs from a cell permissive for pestivirus infection. Expression of such a cDNA library would be driven by a constitutive promoter whose nucleic acid sequence has been fused to the cDNA library in suitable vectors. Such a library would contain a vector encoding a cell receptor for a pestivirus. Non permissive cells can then be transfected with this expression library and further screened for the identification of a cell receptor for a pestivirus.

To this end, the invention proposes a method for ex vivo identifying a cell receptor for pestivirus comprising the step consisting of:

providing an expression cDNA library obtained from a cell permissive for pestivirus infection;

transfecting cells that are not permissive for pestivirus infection with said expression cDNA library;

contacting said transformed cells with pestivirus-like particles of the invention;

identifying and isolating those transformed cells that have become permissive for pestivirus infection;

isolating the expression vector transfected in cells that have become permissive; and identifying as a receptor for pestivirus the proteins encoded by the cDNA sequence of said isolated expression vectors.

Advantageously, the expression cDNA library is expressed from retroviral vectors that comprise glycoproteins that allow infection of the pestivirus non permissive cells. Such glycoproteins can be the VSV-G glycoprotein derived from vesicular stomatitis virus (VSV) whose receptor is expressed in most cell types ex vivo. Such viral particles can be assembled using a packaging competent retrovirus-derived genome that comprises the expression cDNA library, and optionally a marker gene. According to this embodiment the method for isolating the expression vector expressed in cells that have become permissive to infection by the pestivirus-like particles of the invention is greatly facilitated. Indeed this latter embodiment is particularly advantageous in that the process of cell infection with retroviral vectors has greater efficacy, as compared to cell transfection. Furthermore, cell infection leads to stable integration of viral genome in the cellular genome. Accordingly, transgenes, i.e. cDNA and marker gene that are carried by the pseudo-particles of the invention, are found to be stably expressed by infected cells. This in contrast with classical vectors used for transfection that do not integrate into cellular genome and for which expression may be transient.

In another aspect, the invention relates to the use of an infectious particle as defined above, for the identification of molecules capable of interfering with pestivirus entry in cells.

In particular, herein is provided a method of ex vivo screening or identification of molecules capable of interfering with pestivirus entry in cells comprising comparison of the level of cell infection by the particles of the invention in the presence or the absence of a candidate molecule. Said method preferably comprises the steps consisting of:

contacting a cell susceptible to pestivirus infection with an infectious pestivirus-like particle, in the absence or presence of a candidate molecule, under conditions that allow cell infection with pestivirus-like particle in the absence of any candidate molecule;

assessing cell infectivity in the absence and in the presence of said candidate molecule;

comparing cell infectivity measured in presence of said candidate molecule with cell infectivity measured in absence of any candidate molecule;

identifying as a molecule capable of interfering with pestivirus entry the candidate molecule for which cell infectivity, as measured in the presence of said molecule, is decreased as compared to cell infectivity measured in the absence of any candidate molecule.

Contacting a cell susceptible to pestivirus infection with an infectious pestivirus-like particle, and a candidate molecule can be carried out by contacting simultaneously said cell, pestivirus-like particle and candidate molecule. Otherwise, two of these three elements can be contacted under conditions sufficient to allow their interaction before addition of the third missing element.

Cell infectivity can be readily assessed by one skilled in the art. One can take advantage of the embodiment wherein the infectious pestivirus-like particle carries a detectable marker gene to detect cell infection. In a preferred embodiment, the marker gene is a fluorescent marker gene, such as GFP, and the infection is detected by means of fluorescence measurement, for instance by flow cytometry analysis of cells contacted with said infectious particles.

A cell suitable to be used in the method of identification of molecules interfering with pestivirus cell entry may be for instance a kidney primary cell, or cell line, from cattle, pig or sheep.

Such molecules capable of interfering with pestivirus entry in cells may constitute new antiviral drugs.

The infectious particles of the invention are further useful for diagnosis of pestivirus infection and follow-up of pestivirus infection, for instance to assess efficacy of a therapy in a patient.

The invention thus concerns the use of an infectious pestivirus-like particle for the in vitro detection of antibodies directed against pestivirus in a biological sample from a subject susceptible to be infected with pestivirus. Said biological sample may be a biological fluid, such as blood or serum, or a tissue biopsy. In a specific embodiment, said antibodies are directed against Erns and/or E1 and/or E2 pestivirus proteins.

Accordingly, the invention provides a method of in vitro diagnosis of a pestivirus infection in a patient comprising detecting immune complexes formed by interaction of anti-pestivirus antibodies likely to be present in a biological sample of the patient, with pestivirus-like particle of the invention. Said method may in particular comprise the steps consisting of:

contacting a biological sample with an infectious pestivirus-like particle of the invention under conditions sufficient to allow formation of complexes by binding of said infectious particle to antibodies directed against pestivirus present in the biological sample;

detecting said complexes, which presence is indicative of a pestivirus infection.

The presence of antibodies reactive with pestivirus-like particles can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the pestivirus-like particle and the antibody or antibodies reacted therewith.

In another embodiment, said method of in vitro diagnosis of a pestivirus infection in a patient comprises detecting an inhibitory effect of anti-pestivirus antibodies likely to be present in a biological sample of the patient, on the infection of a permissive cell by a pestivirus-like particle of the invention. Said method may in particular comprise the steps consisting of:

contacting a cell permissive for pestivirus infection with a pestivirus-like particle and a biological sample;

comparing cell infectivity measured in presence of said biological sample with cell infectivity measured in absence of said biological sample;

detecting the inhibition of pestivirus-like particle infection of a permissive cell as a decrease in cell infectivity measured in presence of said biological sample compared with cell infectivity measured in absence of said biological sample, said inhibition being indicative of a pestivirus infection.

This embodiment is advantageous in that the method relies on the detection of the specific antibodies that are neutralizing for cell infection, that is those patient's antibodies that are effective against viraemia.

In a further embodiment of this invention, commercial diagnostic kits may be useful to carry out the above diagnosis methods, by detecting the presence or absence of immune complexes formed by pestivirus particles and antibodies directed against pestivirus in a biological sample from a subject susceptible to be infected with pestivirus, or by detecting an inhibition of pestivirus-like particle infection of a permissive cell by anti-pestivirus neutralizing antibodies likely to be present in a biological sample of the patient. Such kits may comprise at least a pestivirus-like particle of the present invention. Where the method involves detection of immune complexes, the kits may further comprise appropriate means of detection of said immune complexes. Preferably the kit of the invention further comprises directions, and protocols, depending upon the method selected, e.g., "competitive" , "sandwich", and the like. The kits may also contain peripheral reagents such as buffers, stabilizers, etc. . . .

In another aspect of the invention, the infectious pestivirus-like particles may be used for vaccination purposes.

According to an embodiment, the invention thus proposes a method of vaccination, notably against pestivirus infection, that comprises administration of a pestivirus-like particle to a subject in need thereof. The invention also relates to a vaccine composition comprising a pestivirus-like particle and a pharmaceutically acceptable carrier. The invention further provides an immunogenic composition comprising in a pharmaceutical acceptable carrier, a pestivirus-like particle disclosed herein.

The vaccine and immunogenic compositions of the invention may be drawn to confer immunity, or elicit an immune response against pestivirus.

However, where the pestivirus-like particles of the invention further carry an additional gene encoding another antigen, different from pestivirus antigens, the invention provides a recombinant viral vaccine useful to raise an immune response against said antigen. Actually, the use of pseudo-particles described herein makes it possible to improve the elicited immune response through combining several presentation and processing pathways of an antigen. For instance, a vaccine composition of the invention, when administered, results in the pestivirus-like particles infecting cells of the host. The transgene encoding the antigen is then integrated in the cellular genome, and subsequently expressed by the cell, such that there is both a cellular and a humoral immune response elicited by the vaccine composition.

Advantageously, the pestivirus-like particles may further carry a transgene encoding an immune modulator, which allows for enhancement of the raised immune reaction.

The vaccination or immunogenic composition of the present invention may additionally contain an adjuvant. A number of adjuvants are known to those skilled in the art. Examples of suitable adjuvants include, for example, include aluminum hydroxide; Saponin; detergents such as Tween 80; animal, mineral or vegetable oils, Corynebacterium or Propionibacterium-derived adjuvants; Mycobacterium bovis (Bacillus Calmette and Guerinn, or BCG); cytokines; acrylic acid polymers such as carbomer; EMA; or combinations thereof.

The route of administration is any conventional route used in the vaccine field. As general guidance, a vaccine composition of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected.

In still another embodiment the particles of the invention may be used as vectors for gene transfer and/or gene therapy. Gene therapy is defined as the introduction of genetic material into a cell in order to either change its phenotype or genotype. Furthermore, such a delivery system is amenable to scale up for reproducibly producing large titers of infectious, replication-defective pestivirus-like particles particles.

Accordingly, the invention relates to a method for in vivo or in vitro transferring a transgene of interest in a cell, which method comprises infecting a cell with a pestivirus-like particle of the invention, wherein the particle carries a transgene of interest.

The invention further relates to the use of a pestivirus-like particle of the invention, that carries a transgene of interest, for the preparation of a medicament for the prevention or treatment of a disease in a patient, wherein the pestivirus-like particle allows the transfer of the transgene of interest into a cell of the patient, and encodes a product that has a prophylactic or therapeutic effect against the disease.

In the above described uses of the particles of the invention the pestivirus may preferably be selected from the group consisting of bovine viral diarrhea virus (BVDV), swine fever virus (SFV), and Border disease virus (BDV).

The invention will be further understood in view of the following examples.

EXAMPLE 1

Generation of Pestivirus Pseudo-Particles

Pestivirus pseudo-particles are generated by assembling full-length, unmodified Erns. E1 and E2 glycoproteins onto retroviral core proteins derived from murine leukemia virus (MLV). To investigate further whether functional pestivirus pseudo-particles are also produced with Erns, E1 and E2 expressed in trans with only one or two of the glycoproteins, expression vectors that encode Erns. E1, E2, Erns and E1, Erns and E2, or Erns and E1 and E2 glycoproteins are designed.

Construction of Expression Vectors Encoding the Viral Components

Plasmids expressing wild type ErnsE1E2 polyproteins are constructed by standard methods (Sambrook et al., 1989).

The specific polynucleotide and polypeptide constructs of BVDV deltaCErnsE1E2p7, deltaCErbsE1E2, deltaCE1E2p7 and deltaCE1E2 are shown in SEQ ID No 19 to 26, respectively.

Generation of Pestivirus Pseudo-Particles

Retroviruses were chosen as platforms for assembly of pestivirus-pp because their cores can incorporate a variety of different cellular and viral glycoproteins and because they can easily package and integrate genetic markers into host cell DNA.

REFERENCES

Ausubel F. M. et al. (eds.), Current Protocols in Molecular Biology, John Wiley & Sons, Inc. (1994).

Felgner et al. Science 337, 387–388. (1989).

Sambrook, J., Fritsch, E. F., and Maniatis, T. *Molecular Cloning: A Laboratory Manual,* 2nd Ed., Cold Spring Harbor Laboratory, Cold Spring Harbor, N.Y. (1989).

Wu et al., (1988) J. Biol. Chem. 263:14621–14624.

Wu et al., (1992) J. Biol. Chem. 267:963–967.

The invention claimed is:

1. A method for producing pestivirus-like particles ex vivo comprising the steps of:

providing a first nucleic acid sequence comprising a packaging competent genome from a retrovirus;

providing a second nucleic acid sequence comprising a cDNA encoding core proteins from said retrovirus;

providing a third nucleic acid sequence comprising a cDNA encoding a polyprotein comprising successively a pestivirus core protein, and a Erns protein and/or pestivirus E1 protein and/or a pestivirus E2 protein, and optionally a pestivirus p7 protein;

transfecting host cells with said nucleic acid sequences and maintaining the transfected cells in culture for sufficient time to allow expression of the cDNAs to produce structural proteins from pestivirus and retrovirus; and allowing the structural proteins to form virus-like particles which do not include the pestivirus core protein.

2. The method according to claim 1, wherein said packaging competent genome from a retrovirus and core proteins are from a retrovirus selected from the group consisting of murine leukemia virus (MLV), avian leukosis virus (ALV), respiratory syncytial virus (RSV), Mason-Pfizer monkey virus (MPMV), human immunodeficiency virus 1 (HIV-1), human immunodeficiency virus 2 (HIV-2), simian immunodeficiency virus (SIV), equine infectious anemia virus (EIAV), caprine arthritis encephalitis virus (CAEV), and human foamy virus (HFV).

3. The method according to claim 1, wherein core, Erns, E1 and E2 pestivirus proteins, and optionally p7 pestivirus protein, are from the same pestivirus.

4. The method according to claim 1, wherein said pestivirus is selected from the group consisting of bovine viral diarrhea virus, swine fever virus, and border disease virus.

* * * * *